(12) United States Patent
Stranix et al.

(10) Patent No.: US 8,742,123 B2
(45) Date of Patent: Jun. 3, 2014

(54) HIV INTEGRASE INHIBITORS FROM PYRIDOXINE

(75) Inventors: Brent Stranix, Pointe-Claire (CA); Francis Beaulieu, Laprairie (CA); Jean-Emmanuel Bouchard, Montréal (CA); Guy Milot, Longueuil (CA); Wang Zhigang, Lachine (CA); Réjean Ruel, St. Lambert (CA)

(73) Assignee: TaiMed Biologics, Inc., Taipei (TW)

( * ) Notice: Subject to any disclaimer, the term of this patent is extended or adjusted under 35 U.S.C. 154(b) by 224 days.

(21) Appl. No.: 12/995,890

(22) PCT Filed: Jun. 4, 2009

(86) PCT No.: PCT/CA2009/000787
§ 371 (c)(1),
(2), (4) Date: Apr. 7, 2011

(87) PCT Pub. No.: WO2009/146555
PCT Pub. Date: Dec. 10, 2009

(65) Prior Publication Data
US 2011/0178120 A1 Jul. 21, 2011

Related U.S. Application Data

(60) Provisional application No. 61/130,874, filed on Jun. 4, 2008.

(51) Int. Cl.
*A61K 31/44* (2006.01)
*C07D 213/81* (2006.01)
(52) U.S. Cl.
CPC .................................. *C07D 213/81* (2013.01)
USPC .......................................... 546/323; 514/302
(58) Field of Classification Search
None
See application file for complete search history.

(56) References Cited

FOREIGN PATENT DOCUMENTS

| EP | 1 004 578 | 5/2000 |
|---|---|---|
| EP | 1867636 A1 * | 12/2007 |
| WO | WO 99/32451 | 7/1999 |
| WO | WO 2004/039803 | 5/2004 |
| WO | WO 2005/019174 | 3/2005 |
| WO | WO 2005/103003 | 11/2005 |

OTHER PUBLICATIONS

International Search Report for PCT/CA2009/000787, mailed Sep. 3, 2009 (5 pages).
International Preliminary Report on Patentability and Written Opinion for PCT/CA2009/000787, mailed Dec. 6, 2010 (8 pages).
Communication enclosing Extended European Search Report and European Search Opinion for EP 09 757 017.0, dated Feb. 6, 2012 (8 pages).

* cited by examiner

*Primary Examiner* — Heidi Reese
(74) *Attorney, Agent, or Firm* — Clark & Elbing LLP

(57) ABSTRACT

The present invention relates to pyridoxine (vitamin $B_6$) derived compounds of formula (I), pharmaceutically acceptable salts, or solvates thereof, wherein $R_1$, $R_2$, $R_4$, A, L $B_1$ and $B_2$ are as defined in the specification, and pharmaceutical compositions comprising the compounds. Compounds of formula (I) inhibit Human Immunodeficiency Virus (HIV)-integrase enzyme and are useful for preventing and treating HIV infection and AIDS.

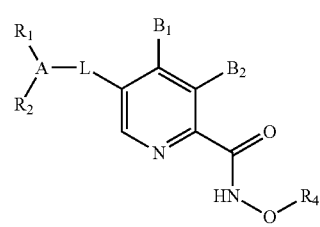

28 Claims, 1 Drawing Sheet

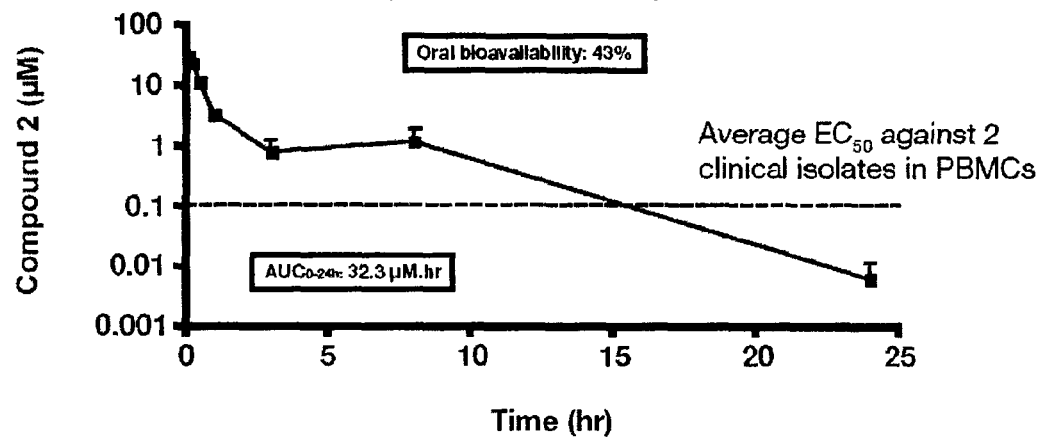

HIV INTEGRASE INHIBITORS FROM PYRIDOXINE

CROSS-REFERENCE TO RELATED APPLICATIONS

This application is a U.S. National Stage Application of International Patent Application No. PCT/CA2009/000787, filed Jun. 4, 2009, which claims priority to U.S. Provisional Application No. 61/130,874, filed Jun. 4, 2008, each of which is herein incorporated by reference in its entirety.

FIELD OF THE INVENTION

The present invention is directed to pyridoxine (vitamin $B_6$) derived compounds of Formula I, pharmaceutically acceptable salts or solvates thereof, pharmaceutical formulations comprising one or more compounds of Formula I, their synthesis, and use as modulators or inhibitors of human immunodeficiency virus (HIV) integrase enzyme. Compounds of the present invention are useful for prophylaxis, treatment, delay in the onset or delay in the progression of human immuno-deficiency virus (HIV) infection, acquired immune deficiency syndrome AIDS, AIDS-related complex (ARC), and other diseases and conditions caused or mediated by HIV infection.

BACKGROUND OF THE INVENTION

Retroviruses designated as human immunodeficiency virus (HIV), particularly strains known as HIV-1 and HIV-2, are the etiological agent of AIDS, ARC, and other diseases or conditions caused or mediated by HIV. HIV infection and AIDS are difficult to treat due to the ability of retroviruses to rapidly replicate, mutate and acquire drug resistance. To date, the treatment of AIDS and HIV infection and the development of new drugs for AIDS and HIV infection have focused primarily on the inhibition of HIV replication by targeting key steps in retroviral replication, such as conversion of viral RNA to viral DNA (reverse transcription) and insertion (integration) of viral DNA into the host genome. These steps rely on the activity of HIV enzymes including reverse transcriptase, protease and integrase. Various synthetic antiviral agents that block various stages of the HIV replication cycle have been developed and marketed including compounds that: interfere with viral binding to CD4 (−) T-lymphocytes (for example, soluble CD4), block viral reverse transcriptase (for example, didanosine and zidovudine (AZT)), block viral aspartyl protease (for example Ritonavir and Indinavir) and inhibit viron budding (for example interferon). Some of these agents have proved ineffective in clinical tests and others, primarily those that target the early stages of viral replication, have no effect on the production of infectious virions in chronically infected cells. Furthermore, administration of therapeutic doses of these agents has commonly led to cell-toxicity, unwanted side effects, such as anemia, neurotoxicity and bone marrow suppression, and rapid emergence of drug resistance which limits safe and effective treatment of AIDS, HIV infection and other HIV-caused diseases.

The use of combination therapy has suppressed the emergence of resistance relative to monotherapy, however even with combination therapy there is a loss of efficacy in 30-50% of patients due to the development of viral resistance. Considering the shortcomings of reverse transcriptase and protease inhibitors, even when used as part of a drug cocktail (combination therapy), there is a need for new antiviral drugs and in particular drugs that do not lead to cross-resistance with the current standard of care.

SUMMARY OF THE INVENTION

The compounds of the present invention are useful for inhibiting or modulating HIV integrase enzyme activity and, in particular, for inhibiting HIV replication and for treating HIV infection, AIDS, and HIV-mediated diseases and conditions. The present invention relates to a series of integrase inhibitors derived from pyridoxine and pharmaceutically acceptable derivatives thereof (e.g., salts and solvates).

In one aspect the present invention are compounds of formula I,

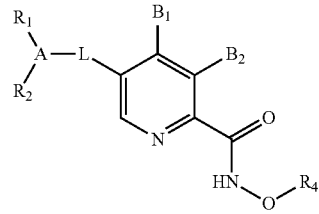

wherein:

A is a six membered carbocyclic or heterocyclic ring system;

$R_1$ is H, $C_{1-6}$ alkyl, $C_{1-6}$ branched alkyl, $C_{2-6}$ alkenyl, halogen (F, Cl, Br, I), OH, O—($C_{1-6}$ alkyl), (O—$C_{1-6}$ branched alkyl), $CO(R_9)$, $COO(R_9)$, $CON(R_9)(R_{9a})$, or $SO_2N(R_9)(R_{9a})$, wherein said $R_9$ and $R_{9a}$ are selected independently from the group consisting of H, $C_{1-6}$ alkyl, $C_{1-6}$ fluoro-alkyl, benzyl, phenyl and heterocycle; $R_2$ is H, $C_{1-6}$ alkyl, $C_{1-6}$ branched alkyl, $C_{2-6}$ alkenyl, halogen (F, Cl, Br, I), OH, O—($C_{1-6}$ alkyl), (O—$C_{1-6}$ branched alkyl), $CO(R_{10})$, $COO(R_{10})$, or $CON(R_{10})(R_{10a})$, wherein said $R_{10}$ and $R_{10a}$ are selected independently from the group consisting of H, $C_{1-6}$ alkyl, $C_{1-6}$ fluoro-alkyl, benzyl, phenyl and heterocycle; or $R_1$ and $R_2$ are ortho substituents that together form a carbocyclic or heterocyclic ring system;

L is —N(R')C(O)—; —C(O)N(R')—; —OC(O)—; —C(O)O—; —OC(O)N(R')—; —N(R')C(O)O—; —N(R')C(O)N(R')—; —C($R^{a1}$)($R^{a2}$)C($R_{b1}$)($R_{b2}$)C($R^{c1}$)($R^{c2}$)—; —C($R_{a1}$)($R_{a2}$)C($R_{b1}$)($R_{b2}$)—; —C($R_{a1}$)($R_{a2}$)C($R_{b1}$)($R_{b2}$)C($R_{c1}$)($R_{c2}$)—Z—C($R_{a1}$)($R_{a2}$)C($R_{b2}$)($R_{b2}$)C($R_{c1}$)($R_{c2}$)—; —C($R_{a1}$)($R_{a2}$)C($R_{b1}$)($R_{b2}$)C($R_{c1}$)($R_{c2}$)—Z—C($R_{a1}$)($R_{a2}$)C($R_{b1}$)($R_{b2}$)—; —C($R_{a1}$)($R_{a2}$)C($R_{b1}$)($R_{b2}$)C($R_{c1}$)($R_{c2}$)—Z—C($R_{a1}$)($R_{a2}$)—; —C($R_{a1}$)($R_{a2}$)C($R_{b1}$)($R_{b2}$)C($R_{c1}$)($R_{c2}$)—Z—; —C($R_{a1}$)($R_{a2}$)C($R_{b1}$)($R_{b2}$)—Z—C($R_{a1}$)($R_{a2}$)C($R_{b1}$)($R_{b2}$)C($R_{c1}$)($R_{c2}$)—; —C($R_{a1}$)($R_{a2}$)—Z—C($R_{a1}$)($R_{a2}$)C($R_{b1}$)($R_{b2}$)C($R_{c1}$)($R_{c2}$)—; —Z—C($R_{a1}$)($R_{a2}$)C($R_{b1}$)($R_{b2}$)C($R_{c1}$)($R_{c2}$)—; —C($R_{a1}$)($R_{a2}$)C($R_{b1}$)($R_{b2}$)—Z—C($R_{a1}$)($R_{a2}$)C($R_{b1}$)($R_{b2}$)—; —C($R_{a1}$)($R_{a2}$)C($R_{b1}$)($R_{b2}$)—Z—C($R_{a1}$)($R_{a2}$)—; —C($R_{a1}$)($R_{a2}$)C($R_{b1}$)($R_{b2}$)—Z—; —C($R_{a1}$)($R_{a2}$)—Z—C($R_{a1}$)($R_{a2}$)C($R_b$)($R_{b2}$)—; —Z—C($R_a$)($R_{a2}$)C($R_{b1}$)($R_{b2}$)—; —C($R_{a1}$)($R_{a2}$)—Z—C($R_a$)($R_{a2}$)—; —C($R_a$)($R_{a2}$)—Z—; or —Z—C($R_{a1}$)($R_{a2}$)—; wherein each $R_{a1}$, $R_{a2}$, $R_{b1}$, $R_{b2}$, $R_{c1}$, and $R_{c2}$ is, independently, selected from selected from H, $C_{1-6}$ alkyl, $C_{1-6}$ fluoro-alkyl, hydroxy-alkyl, benzyl, phenyl and heterocycle, or, alternatively, one or more of $R_{a1}$ and $R_{a2}$; $R_{b1}$ and $R_{b2}$; and $R_d$ and $R_{c2}$ combine to form a carbocyclic ring, and wherein Z is selected from —N(R')C(O)—; —C(O)N(R')—; —OC(O)—; —C(O)O—; —OC(O)N(R')—; —N(R')C(O)O—; —N(R')C(O)N(R')—;

—N(R')—; —SO$_2$—; and —O—; wherein R' is selected from H, C$_{1-6}$ alkyl, benzyl, SO$_2$R", and C(O)R", C(O)OR", and R" is selected from C$_{1-6}$ alkyl, C$_{1-6}$ fluoro-alkyl, heteroalkyl, carbocyclic group, benzyl, phenyl and heterocycle;

B$_1$ is —R$_3$, CH$_2$OR$_3$, CH$_2$N(R$_8$)(R$_{8a}$), C(O)OR$_3$ or C(O)N(R$_8$)(R$_{8a}$), wherein each of R$_8$ and R$_{8a}$ is, independently, selected from the group consisting of H, C$_{1-6}$ alkyl, C$_{1-6}$ fluoro-alkyl, benzyl, phenyl and heterocycle;

B$_2$ is H or OR$_5$;

R$_3$ is H, C$_{1-6}$ alkyl, C$_{1-6}$ fluoroalkyl, benzyl, phenyl, or heterocycle; and R$_5$ is C$_{1-6}$ alkyl, C$_{1-6}$ fluoroalkyl, benzyl, phenyl, or heterocycle; or, alternatively, R$_3$ and R$_5$ combine to form a heterocyclic ring system; and R$_4$ is H, C$_{1-6}$ alkyl, C$_{1-6}$ fluoroalkyl, benzyl, phenyl, or heterocycle; and pharmaceutically acceptable salts and solvates thereof.

In certain embodiments of the compounds of formula I, A is a phenyl ring, a pyridine ring, or a cyclohexyl ring.

In still other embodiments of the compounds of formula I, B$_1$ is H, CH$_3$, CH$_2$OH, or CH$_2$OCH$_3$.

In particular embodiments of the compounds of formula I, L is —CH$_2$OCH$_2$—, —CH$_2$CH$_2$OCH$_2$—, —OCH$_2$—, —CH$_2$NHCH$_2$—, —C(cyclo-C$_2$H$_4$)NHCH$_2$—, —NHCH$_2$—, —CH$_2$CH$_2$NHCH$_2$—, —CH$_2$NHC(O)—, —CH$_2$N(CH$_3$)C(O)—, —CH(CH$_2$OH)NHC(O)—, —C(cyclo-C$_2$H$_4$)NHC(O)—, —CH$_2$CH$_2$NHC(O)—, —C(O)NH—, —CH$_2$OC(O)NH—, —NHC(O)NH—, —CH$_2$CH$_2$CH$_2$—, —CH$_2$CH$_2$—, —SO$_2$CH$_2$—, or —CH$_2$SO$_2$CH$_2$—.

In certain embodiments of the compounds of formula I, R$_1$ is selected from a halogen, —OH or —OCH$_3$, R$_2$ is selected from —OH, —H, and a halogen, or R$_1$ and R$_2$ combine to form a cyclic acetal or cyclic ketal, R$_4$ is —H or benzyl, B$_2$ is OR$_5$, and R$_5$ is —H or benzyl.

In certain embodiments, the compounds of formula I are further described by formula Ia:

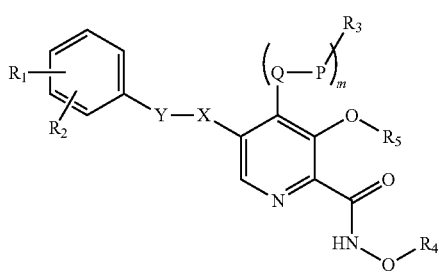

wherein:

Y—X is —C(R$_7$)(R$_{7a}$)N(R')C(O)—; —C(R$_7$)(R$_{7a}$)OC(O)—; —C(R$_7$)(R$_{7a}$)N(R')C(R$_6$)(R$_{6a}$)—; or —C(R$_7$)(R$_{7a}$)OC(R$_6$)(R$_{6a}$)—, wherein each of R$_6$, R$_{6a}$, R$_7$, and R$_{7a}$, is, independently, selected from H, C$_{1-6}$ alkyl, C$_{1-6}$ fluoro-alkyl, benzyl, phenyl and heterocycle, R' is selected from H, C$_{1-6}$ alkyl, benzyl, SO$_2$R", and C(O)R", and R" is selected from C$_{1-6}$ alkyl, C$_{1-6}$ fluoro-alkyl, benzyl, phenyl and heterocycle;

Q is H, CH$_2$, CH$_3$, or CO;

P is H, O, N(R$_8$)(R$_{8a}$), or is absent, wherein said R$_8$ and R$_{8a}$ are selected independently from the group consisting of H, C$_{1-6}$ alkyl, C$_{1-6}$ fluoro-alkyl, benzyl, phenyl and heterocycle;

R$_1$ is H, C$_{1-6}$ alkyl, C$_{1-6}$ branched alkyl, C$_{2-6}$ alkenyl, halogen (F, Cl, Br, I), OH, O—(C$_{1-6}$ alkyl), (O—C$_{1-6}$ branched alkyl), CO(R$_9$), COO(R$_9$), CON(R$_9$)(R$_{9a}$), or SO$_2$N(R$_9$) (R$_{9a}$), wherein said R$_9$ and R$_{9a}$ are selected independently from the group consisting of H, C$_{1-6}$ alkyl, C$_{1-6}$ fluoro-alkyl, benzyl, phenyl and heterocycle; R$_2$ is H, C$_{1-6}$ alkyl, C$_{1-6}$ branched alkyl, C$_{2-6}$ alkenyl, halogen (F, Cl, Br, I), OH, O—(C$_{1-6}$ alkyl), (O—C$_{1-6}$ branched alkyl), CO(R$_{10}$), COO(R$_{10}$), or CON(R$_{10}$)(R$_{10a}$), wherein said R$_{10}$ and R$_{10a}$ are selected independently from the group consisting of H, C$_{1-6}$ alkyl, C$_{1-6}$ fluoro-alkyl, benzyl, phenyl and heterocycle; or R$_1$ and R$_2$ are ortho substituents that together form a carbocyclic or heterocyclic ring system;

R$_3$ is H, C$_{1-6}$ alkyl, C$_{1-6}$ fluoroalkyl, benzyl, phenyl, heterocycle, or is absent; and R$_5$ is H, C$_{1-6}$ alkyl, C$_{1-6}$ fluoroalkyl, benzyl, phenyl, or heterocycle; or R$_3$ and R$_5$ combine to form a heterocyclic ring system;

R$_4$ is H, C$_{1-6}$ alkyl, C$_{1-6}$ fluoroalkyl, benzyl, phenyl, or heterocycle; and m is 0 or 1; or pharmaceutically acceptable salts or solvates thereof.

Further provided herein are compounds of formula Ia, wherein: Q is CH$_2$, P is O, R$_3$ is H, Y—X is CH$_2$NHCH$_2$ or CH$_2$NHCO, R$_1$ is selected from a halogen, —OH or —OCH$_3$, R$_2$ is selected from —OH, or R$_1$ and R$_2$ combine to form a cyclic acetal or cyclic ketal, —H, and a halogen, R$_4$ is —H or benzyl, and R$_5$ is —H or benzyl, or pharmaceutically acceptable salts or solvates thereof.

Further provided herein are compounds of formula Ia, Q is CH$_2$, P is O, R$_3$ is CH3, Y—X is CH$_2$OCH$_2$, R$_1$ is selected from a halogen, —O or —OCH$_3$, R$_2$ is selected from —O, —H, and a halogen, or R$_1$ and R$_2$ combine to form a cyclic acetal or cyclic ketal, R$_4$ is —H or benzyl and R$_5$ is —H or benzyl or pharmaceutically acceptable salts or solvates thereof.

Further provided herein are compounds of formula I selected from N5-(4-fluorobenzyl)-N2,3-dihydroxy-4-(hydroxymethyl)pyridine-2,5-dicarboxamide, N5-(3-chloro-4-fluorobenzyl)-N2,3-dihydroxy-4-(hydroxymethyl)pyridine-2,5-dicarboxamide, N5-(3,4-dichlorobenzyl)-N2,3-dihydroxy-4-(hydroxymethyl)pyridine-2,5-dicarboxamide, and 5-(benzyloxymethyl)-N2,3-dihydroxy-4-(hydroxymethyl)picolinamide.

Further provided herein are compounds of formula I selected from N$^2$,3-bis(benzyloxy)-N$^5$-(4-fluorobenzyl)-4-(hydroxymethyl)pyridine-2,5-dicarboxamide, N$^5$-(4-fluorobenzyl)-N$^2$,3-dihydroxy-4-(hydroxymethyl)pyridine-2,5-dicarboxamide, N$^5$-(benzo[d][1,3]dioxol-5-ylmethyl)-N2,3-bis(benzyloxy)-4-(hydroxymethyl)pyridine-2,5-dicarboxamide, N$^5$-(benzo[d][1,3]dioxol-5-ylmethyl)-N2,3-dihydroxy-4-(hydroxymethyl)pyridine-2,5-dicarboxamide, N$^2$,3-bis(benzyloxy)-4-(hydroxymethyl)-N$^5$-(4-methoxybenzyl)pyridine-2,5-dicarboxamide, N$^2$,3-dihydroxy-4-(hydroxymethyl)-N$^5$-(4-methoxybenzyl)pyridine-2,5-dicarboxamide, N$^2$,3-bis(benzyloxy)-N$^5$-(3,5-difluorobenzyl)-4-(hydroxymethyl)pyridine-2,5-dicarboxamide, N$^5$-(3,5-difluorobenzyl)-N$^2$,3-dihydroxy-4-(hydroxymethyl)pyridine-2,5-dicarboxamide, 5-((4-fluorobenzylamino)methyl)-N,3-dihydroxy-4-(methoxymethyl)picolinamide), 5-((3,5-difluorobenzylamino)methyl)-N, 3-dihydroxy-4-(hydroxymethyl)picolinamide, 5-((benzo[d][1,3]dioxol-5-ylmethylamino)methyl)-N,3-dihydroxy-4-(hydroxymethyl)picolinamide, N5-(4-fluorobenzyl)-N$^2$,3-dihydroxy-4-(methoxymethyl)-N$^5$-methylpyridine-2,5-dicarboxamide, N$^2$,3-bis(benzyloxy)-N$^5$-(3-chloro-4-fluorobenzyl)-4-(hydroxymethyl)pyridine-2,5-dicarboxamide, N$^5$-(3-chloro-4-fluorobenzyl)-N2,3-dihydroxy-4-(hydroxymethyl)pyridine-2,5-dicarboxamide, N$^2$, 3-bis(benzyloxy)-N$^5$-(3,4-dichlorobenzyl)-4-(hydroxymethyl)pyridine-2,5-dicarboxamide, N$^5$-(3,4-dichlorobenzyl)-N$^2$,3-dihydroxy-4-

(hydroxymethyl)pyridine-2,5-dicarboxamide, N,3-dihydroxy-4-(hydroxymethyl)-5-((4-methoxybenzyloxy)methyl)-picolinamide, 5-(benzyloxymethyl)-N,3-dihydroxy-4-(hydroxymethyl)picolinamide, N-hydroxy-5-((4-methoxybenzyloxy)methyl)-2,2-dimethyl-4H-[1,3]dioxino[4,5-c]pyridine-8-carboxamide, and $N^5$-(3,4-difluorobenzyl)-N2,3-dihydroxy-4-(hydroxymethyl)pyridine-2,5-dicarboxamide.

Further provided herein are compounds of formula I selected from N,9-bis(benzyloxy)-3,3-dimethyl-1,5-dihydro-[1,3]dioxepino[5,6-c]pyridine-8-carboxamide, N,3-bis(benzyloxy)-4,5-bis(hydroxymethyl)picolinamide, N,7-bis(benzyloxy)-3-oxo-1,3-dihydrofuro[3,4-c]pyridine-6-carboxamide, $N^2$,3-bis(benzyloxy)-$N^5$-(4-fluorobenzyl)-4-(hydroxymethyl)pyridine-2,5-dicarboxamide, N,3-bis(benzyloxy)-5-(4-fluorobenzylamino)methyl)-4-(hydroxymethyl)picolinamide, 5-((3,5-difluorobenzylamino)methyl)-N,3-dihydroxy-4-(hydroxymethyl)picolinamide, 5-((benzo[d][1,3]dioxol-5-ylmethylamino)methyl)-N,3-bis(benzyloxy)-4-(hydroxymethyl)picolinamide, 5-(benzyloxy)-N-(4-fluorobenzyl)-4-(hydroxymethyl)-6-methylnicotinamide, 5-(benzyloxy)-N-(4-fluorobenzyl)-4-(methoxymethyl)-N,6-dimethylnicotinamide, 3-(benzyloxy)-5-((4-fluorobenzyl)(methyl)carbamoyl)-4-(methoxymethyl)-2-methylpyridine 1-oxide, 5-(benzyloxy)-N-(4-fluorobenzyl)-6-(hydroxymethyl)-4-(methoxymethyl)-N-methylnicotinamide, 5-(benzyloxy)-N-(4-fluorobenzyl)-6-formyl-4-(methoxymethyl)-N-methylnicotinamide, methyl 3-(benzyloxy)-5-((4-fluorobenzyl)(methyl)carbamoyl)-4-(methoxymethyl)picolinate, $N^2$,3-bis(benzyloxy)-$N^5$-(4-fluorobenzyl)-4-(methoxymethyl)-$N^5$-methylpyridine-2,5-dicarboxamide, $N^5$-(4-fluorobenzyl)-N2,3-dihydroxy-4-(methoxymethyl)-$N^5$-methylpyridine-2,5-dicarboxamide, 5-((4-methoxybenzyloxy)methyl)-2,2,8-trimethyl-4H-[1,3]dioxino[4,5-c]pyridine, 5-((4-methoxybenzyloxy)methyl)-2,2,8-trimethyl-4H-[1,3]dioxino[4,5-c]pyridine 7-oxide, (5-((4-methoxybenzyloxy)methyl)-2,2-dimethyl-4H-[1,3]dioxino[4,5-c]pyridin-8-yl)methanol, 5-((4-methoxybenzyloxy)methyl)-2,2-dimethyl-4H-[1,3]dioxino[4,5-c]pyridine-8-carbaldehyde, ethyl 5-((4-methoxybenzyloxy)methyl)-2,2-dimethyl-4H-[1,3]dioxino[4,5-c]pyridine-8-carboxylate, ethyl 3-hydroxy-4-(hydroxymethyl)-5-((4-methoxybenzyloxy)methyl)picolinate, N,3-dihydroxy-4-(hydroxymethyl)-5-(4-methoxybenzyloxy)methyl)picolinamide, 5-((4-methoxybenzyloxy)methyl)-2,2-dimethyl-4H-[1,3]dioxino[4,5-c]pyridine-8-carboxylic acid, N-(benzyloxy)-5-(4-methoxybenzyloxy)methyl)-2,2-dimethyl-4H-[1,3]dioxino[4,5-c]pyridine-8-carboxamide, N-(benzyloxy)-3-hydroxy-4-(hydroxymethyl)-5-((4-methoxybenzyloxy)methyl)picolinamide, N-hydroxy-5-((4-methoxybenzyloxy)methyl)-2,2-dimethyl-4H-[1,3]dioxino[4,5-c]pyridine-8-carboxamide.

Further provided herein are pharmaceutical compositions, and pharmaceutically acceptable formulations, comprising a therapeutically effective amount of at least one compound of the present invention, and pharmaceutically acceptable salts or solvates thereof.

The compounds of the present invention inhibit HIV integrase including both HIV-1 and HIV-2 and may be used as antiviral agent against HIV, including HIV-1 and HIV-2 strains.

The compounds of the present invention are useful for prophylaxis, treatment or delay in the onset or progression of HIV infection, or of a disease or condition caused or mediated by HIV infection, including HIV-1 and HIV-2 infection.

In one aspect, the present invention features a method of inhibiting HIV replication, in a mammal, that includes administering to the mammal a replication-inhibiting amount of at least one compound of the present invention, or a pharmaceutically acceptable salt or solvate thereof.

Further provided are methods of inhibiting HIV replication in a cell, comprising contacting the cell with an inhibiting amount of at least one compound of the present invention, or a pharmaceutically acceptable salt, solvate or formulation thereof.

Further provided are methods of inhibiting HIV integrase enzyme activity, that include contacting the integrase enzyme with an integrase-inhibiting amount of at least one compound of the present invention, or a pharmaceutically acceptable salt, solvate or formulation thereof. The method includes contacting a cell directly or administering the compound of the invention to a mammal suffering from an HIV infection.

Another aspect of the present invention includes methods of treating HIV infection in a mammal, comprising administering to the mammal at least one compound of the present invention, or a pharmaceutically acceptable salt, solvate or formulation thereof.

Further provided are methods of treating AIDS in a mammal, comprising administering to the mammal at least one compound of the present invention, or a pharmaceutically acceptable salt, solvate or formulation thereof.

Further provided are methods of treating AIDS in a mammal, comprising administering to the mammal at least one compound of the present invention, or a pharmaceutically acceptable salt, solvate or formulation thereof in combination with one or more additional HIV-inhibiting agent.

Further provided are methods of treating a disease or condition caused or mediated by HIV infection in a mammal, comprising administering to the mammal at least one compound of the present invention, or a pharmaceutically acceptable salt, solvate or formulation thereof.

Further provided are methods of prophylaxis or prevention of HIV infection in a mammal, comprising administering to the mammal at least one compound of the present invention, or a pharmaceutically acceptable salt, solvate or formulation thereof.

Further provided are methods of inhibiting HIV replication in a mammal comprising administering to the mammal at least one compound of the present invention or a pharmaceutically acceptable salt, solvate or formulation thereof.

Further provided are methods of inhibiting HIV replication in a mammal comprising administering to the mammal at least one compound of the present invention, or a pharmaceutically acceptable salt, solvate or formulation thereof and at least one other HIV-inhibiting agent.

Further provided are methods of inhibiting HIV replication in a mammal wherein the HIV is resistant to at least one HIV protease inhibitor, the method comprising administering to the mammal at least one compound of the present invention, or a pharmaceutically acceptable salt, solvate or formulation thereof.

Further provided are methods of inhibiting HIV replication in a mammal, having an HIV infection, wherein the HIV is resistant to at least one HIV reverse transcriptase inhibitor, the method comprising administering to the mammal at least one compound of the present invention, or a pharmaceutically acceptable salt, solvate or formulation thereof.

Further provided are methods of reducing HIV viral load in a mammal infected with HIV, comprising administering to the mammal at least one compound of the present invention, or a pharmaceutically acceptable salt, solvate or formulation thereof.

Further provided are methods of reducing HIV viral load in a mammal infected with HIV, comprising administering to the mammal at least one compound of the present invention, or a pharmaceutically acceptable salt, solvate or formulation thereof in combination with one or more additional HIV-inhibiting agents.

Further provided is the use of at least one compound of the present invention for the manufacture of a pharmaceutical composition for treatment of HIV infection.

Further provided is the use of at least one compound of the present invention for the manufacture of a pharmaceutical composition for treatment of AIDS or ARC.

Further provided is the use of at least one compound of the present invention for the manufacture of a pharmaceutical composition for prevention or prophylaxis of AIDS or ARC.

Further provided is the use of at least one compound of the present invention for the manufacture of a pharmaceutical composition for prevention or prophylaxis of HIV infection.

For any of the above aspects of the invention, the mammal (e.g., human) may have or be suspected of having an HIV infection or an AIDS or HIV mediated disease or condition. The mammal (e.g., human) may or may not have been previously treated with anti-viral or other therapeutic compounds for the HIV infection or AIDS or HIV mediated disease or condition.

BRIEF DESCRIPTION OF THE DRAWING

FIG. 1 is a graph showing the adsorption of compound 2 over time.

DEFINITIONS

The terms "human immunodeficiency virus," "HIV," "HIV-1," or "HIV-2" as used herein refer to a retrovirus that is the causative agent for acquired immunodeficiency Syndrome (AIDS) and diseases, conditions or opportunistic infections associated with AIDS. Previous names for HIV include human T-lymphotropic virus-III (HTLV-III), lymphadenopathy-associated virus (LAV), and AIDS-associated retrovirus (ARV).

The terms "HIV reverse transcriptase," "reverse transcriptase," or "RT" as used herein refer to an enzyme, encoded by a retroviral genome, which catalyzes or mediates the conversion (reverse transcription) of viral RNA to DNA or generation of a provirus (Haseltine W. A. FASEB J. vol. 5, p. 2349-2360 (1991)).

The terms "reverse transcriptase inhibitor" or "HIV reverse transcriptase inhibitor," as used herein, refer to compounds or combinations of compounds that interfere with the proper functioning of the HIV reverse transcriptase enzyme that is responsible for converting single-stranded HIV viral RNA into HIV viral DNA.

The terms "HIV integrase" or "integrase" as used herein refer to an enzyme, encoded by a retroviral genome, that catalyzes or mediates integration of provirus DNA (retroviral double stranded DNA) into the host genomic DNA. The integrase enzyme can serve as a template for viral gene expression by the host transcription system, leading to viral replication (Roth et al., Cell, 1989 Jul. 14; 58(1):47-54.: Bukrinsky M. I., Proc. Natn. Acad. Sci. USA 1992, vol. 89 p. 6580-6584; Gallay et al., Cell. 1995 Nov. 17; 83(4):569-76).

The terms "integrase inhibitor" or "HIV integrase inhibitor," as used herein, refer to a compound or combination of compounds that interfere with the proper functioning of the HIV integrase enzyme that is responsible for inserting the genes of HIV into the DNA of a host cell.

The term "integration" as used herein refers to insertion of viral DNA, retroviral DNA, provirus, or provirus DNA into the host genome mediated by integrase enzyme. Integration generally occurs following association of integrase and viral DNA with the pre-integration complex (PIC) at the host nucleus and transport of the viral DNA into the host nucleus as a component of the pre-integration complex (Goldgur Y et al Proc Natl Acad Sci USA. 1999 Nov. 9; 96(23):13040-3; Sayasith K, Sauvé G and Yelle J. Expert Opin Ther Targets. 2001 August; 5(4):443-464; Debyser Z et al Methods Mol. Biol. 2001; 160:139-55).

The terms "protease inhibitor" or "HIV protease inhibitor" as used herein mean compounds or combinations of compounds that interfere with the proper functioning of the HIV protease enzyme that is responsible for cleaving long strands of viral protein into the separate proteins making up the viral core.

The terms "fusion inhibitor" or "HIV fusion inhibitor," as used herein, refer to compounds or combinations of compounds that bind to the gp41 envelope protein on the surface of CD4 cells and block the structural changes necessary for the virus to fuse with the cell.

The terms "viral load" and "HIV viral load," as used herein, mean the amount of HIV in the circulating blood of a mammal, such as a human. The amount of HIV virus in the blood of mammal can be determined by measuring the quantity of HIV RNA in the blood using methods known to those of ordinary skill in the art.

The term "retrovirus" as used herein refers to a virus belonging to the viral family Retroviridae, which includes viruses that possess an RNA genome, and that replicate via a DNA intermediate.

The term "Vitamin $B_6$" as used herein refers to one or more of three compounds that are commonly referred to as vitamin $B_6$ namely pyridoxal, pyridoxamine and pyridoxine. Pyridoxine differs from pyridoxamine by the substituent at the '4 position. Pyridoxine based on a pyridine ring, with hydroxyl, methyl, and hydroxymethyl substituents and is converted in vivo to pyridoxal 5-phosphate, the biologically active form of pyridoxine.

The terms "comprising" and "including" are used in their open, non-limiting sense.

The term "$C_{1-6}$ alkyl" as used herein means saturated monovalent hydrocarbon radicals having straight or branched moieties and containing from 1 to 6 carbon atoms. The $C_{1-6}$ alkyl group may be substituted or unsubstituted. Examples of such groups include, but are not limited to, methyl, ethyl, propyl, iso-propyl, n-butyl, iso-butyl, and tert-butyl. The term "$C_{1-6}$ fluoro-alkyl" refers to a $C_{1-6}$ alkyl substituted with one or more fluorine atoms. Exemplary $C_{1-6}$ fluoro-alkyl groups include, without limitation, fluoromethyl, trifluoromethyl, and pentafluoroethyl. The term "$C_{1-6}$ branched alkyl" refers to alkyl group that include one or more tertiary or quaternary carbon atoms.

By "$C_{2-6}$ alkenyl" is meant a branched or unbranched hydrocarbon group containing one or more double bonds and having from 2 to 6 carbon atoms. A $C_2$ alkenyl may optionally include monocyclic or polycyclic rings, in which each ring desirably has from three to six members. The $C_{2-4}$ alkenyl group may be substituted or unsubstituted.

By "carbocyclic group" or "carbocyclic ring" is meant a monocyclic or polycyclic ring system which is saturated, partially unsaturated, or unsaturated (aromatic), and which consists of 3 to 8 carbon atoms (unless otherwise specified). Carbocyclic groups include alkyl groups substituted with such a monocyclic or polycyclic ring system. Exemplary cyclic groups include phenyl, benzyl, cyclopropyl, cyclobutyl, cyclopentyl, 2-phenylcyclopropane, and cyclohexyl. The carbocyclic group may be substituted or unsubstituted.

By "heteroalkyl" is meant a branched or unbranched alkyl or alkenyl group having from 1 to 10 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, urethanes, phosphodiesters, phosphoramidates, sulfonamides, and disulfides. A heteroalkyl may optionally include monocyclic, bicyclic, or tricyclic rings (either aromatic or non-aromatic ring systems), in which each ring desirably has three to six members. The heteroalkyl group may be substituted or unsubstituted. Examples of $C_{1-7}$ heteroalkyls include, without limitation, methoxymethyl, benzyloxyethyl, and ethoxyethyl.

The term "heterocycle" and "heterocyclic ring" as used herein means aromatic or non-aromatic, monocyclic, bicyclic, tricyclic, tetracyclic, or spirocyclic group having a total of from 3 to 10 atoms in its ring system, and containing from 2 to 9 carbon atoms and from one to four heteroatoms each independently selected from O, S and N and with the proviso that the ring of said group does not contain two adjacent O atoms or two adjacent S atoms. Furthermore, such heterocycle groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocycle group contains a sulfur atom, said sulfur atom may be oxidized with one or two oxygen atoms to afford either a sulfoxide or sulfone. An example of a 4 membered heterocyclic group is azetidinyl (derived from azetidine). An example of a 5 membered heterocyclic group is thiazolyl and an example of a 10 membered heterocyclic group is quinolinyl. Further examples of such heterocycle groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3 azabicyclo[3.1.0]hexanyl, 3-azabicyclo[4.1.0]heptanyl, 3H-indolyl and quinolizinyl. The heterocycle group may be substituted or unsubstituted.

As used herein, the terms "benzyl" and "phenyl" refer to both substituted and unsubstitued benzyl and phenyl groups, respectively.

As used herein, the term "substituted" refers to a group (e.g., a "$C_{1-6}$ alkyl", "$C_{2-6}$ alkenyl", "$C_{1-6}$ fluoroalkyl", "benzyl", "phenyl", "heterocycle", or "carbocyclic group") in which one or more hydrogen atoms in the group are, independently, replaced with a substituent selected from methyl, ethyl, n-propyl, isopropyl, hydroxy, methoxy, ethoxy, fluorine, chlorine, bromine, iodine, cyano, nitro, amino, alkylamino, dialkylamino, carboxy, chloromethyl, trichloromethyl, trifluoromethyl, methoxyethyl, —$CH_2C(O)NH_2$, —$C(O)CH_2N(CH_3)_2$, —$CH_2CH_2OH$, —$CH_2OC(O)NH_2$, —$CH_2CH_2NH_2$, —$CH_2CH_2CH_2NEt_2$, —$CH_2OCH_3$, —$C(O)NH_2$, —$C(=NH)NH_2$, —$C(=NH)OEt$, —$C(O)NH$-cyclopropyl, —$C(O)NHCH_2CH_2OCH_3$, —$C(O)CH_2CH_2NHCH_3$, —$CH_2CH_2F$, or —$CH_2C(O)NHCH_3$.

The term "inhibiting HIV replication" means reducing or preventing (e.g., by at least 10%, 20% 30%, 40%, 50%, 60%, 70%, 80%, 90% or more) human immunodeficiency virus (HIV) replication in a cell. Such a cell may be present in vitro, or it may be present in vivo, such as in a mammal, such as a human. Such inhibition may be accomplished by administering a compound of the present invention, or a pharmaceutically acceptable salt or solvate thereof, directly to the cell, or to a mammal, in an amount sufficient to inhibit HIV replication. The inhibition of HIV replication in a cell, such as in a mammal, can be measured or monitored using methods known to those of ordinary skill in the art. For example, an amount of a compound of the invention may be administered to a mammal, either alone or as part of a pharmaceutically acceptable formulation. Blood samples may then be withdrawn from the mammal and the amount of HIV virus in the sample may be quantified using methods known to those of ordinary skill in the art. A reduction in the amount of HIV virus in the sample compared to the amount found in the blood before administration of a compound of the invention would represent inhibition of the replication of HIV virus in the mammal. In another example, a reduction in the amount of HIV virus in the sample compared to the amount found in a positive reference sample (e.g., the blood from a subject having HIV but not treated with a compound of the invention) would represent inhibition of the replication of HIV virus in the mammal. The administration of a compound of the invention to the cell, such as in a mammal, may be in the form of single dose or a series of doses. In the case of more than one dose, the doses may be administered in one day or they may be administered over more than one day.

"HIV-inhibiting agent," "HIV antiviral agent," or "anti-HIV agent" as used herein means a compound, including but not limited to the compounds of the present invention, or a pharmaceutically acceptable salt thereof which is capable of inhibiting the replication of HIV in a cell, such as a cell in a mammal. Such compounds may inhibit HIV replication through any mechanism known to those of ordinary skill in the art. Non-limiting examples of HIV-inhibiting agents include an entry inhibitor, a protease inhibitor, a reverse transcriptase inhibitor, a fusion inhibitor, and an integrase inhibitor.

The terms "human immunodeficiency virus-inhibiting amount" or "HIV-inhibiting amount," as used herein, refer to the amount of an HIV-inhibiting agent, or a pharmaceutically acceptable salt of solvate thereof, required to inhibit replication of the human immunodeficiency virus (HIV) in vivo, such as in a mammal, or in vitro. The amount of such compounds required to cause such inhibition can be determined without undue experimentation using methods described herein and those known to those of ordinary skill in the art.

The term "inhibiting HIV integrase enzyme activity," as used herein, means decreasing (e.g., by at least 10%, 20% 30%, 40%, 50%, 60%, 70%, 80%, 90% or more) the activity or functioning of the HIV integrase enzyme either in vitro or in vivo, such as in a mammal, such as a human.

The term "HIV integrase enzyme-inhibiting amount," as used herein, refers to the amount of an HIV-inhibiting agent or a pharmaceutically acceptable salt or solvate thereof, required to decrease the activity of the HIV integrase enzyme either in vivo, such as in a mammal, or in vitro, such as in a cultured cell line. In one example, such inhibition may take place by the compound of the present invention binding directly to the HIV integrase enzyme. In addition, the activity of the HIV integrase enzyme may be decreased in the presence of a compound of the present invention when such direct binding between the enzyme and the compound does not take place. Furthermore, such inhibition may be competitive, non-competitive, or uncompetitive. Inhibition of HIV integrase may be determined using in vitro or in vivo systems, or a combination of both, using methods known to those of ordinary skill in the art.

The term "solvate," as used herein, means a pharmaceutically acceptable solvate form of a compound of the present invention that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof. In one embodiment of the present invention, one solvent molecule is associated with one molecule of the compounds of the present invention, such as a hydrate. In another embodiment of the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention include solvates of compounds of the present invention that retain the biological effectiveness of the non-hydrate form of the compounds.

A "pharmaceutically acceptable salt" as used herein means a salt that retains the biological effectiveness of the free acids and bases of the specified derivative, containing pharmacologically acceptable anions or cations, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, y-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mutate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, valerate salts, and cations, such as sodium, potassium, calcium, magnesium, ammonium, and tetraalkylammonium, among others.

The term "pharmaceutically acceptable formulation," as used herein, means a combination of a compound of the invention, or a pharmaceutically acceptable salt or solvate thereof, and a carrier, diluent, and/or excipients that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar agar, calcium carbonate, and sodium bicarbonate; agents for retarding dissollution such as paraffin; resorption accelerators such as quaternary ammonium compounds; surfaceactive agents such as cetyl alcohol, glycerol monostearate; adsorptive carriers such as keolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional anti-HIV agents. A pharmaceutically acceptable formulation may also include but is not limited to compounds, other than the compounds of formula 1, having a structure such that, upon administration to a recipient or patient, a compound of this invention, active metabolite or residue thereof is directly or indirectly provided.

By "reduce" or "inhibit" is meant the ability to cause an overall decrease of 10%, 20% 30%, 40%, 50%, 60%, 70%, 80%, 90% or more.

The term "therapeutically effective amount," as used herein, means an amount of a compound of the present invention, or a pharmaceutically acceptable salt thereof, that, when administered to a mammal in need of such treatment, is sufficient to effect treatment, as defined herein. Thus, a therapeutically effective amount of a compound of the present invention, or a pharmaceutically acceptable salt thereof, is a quantity sufficient to modulate or inhibit the activity of the HIV integrase enzyme such that a disease condition that is mediated by activity of the HIV integrase enzyme is reduced or alleviated.

The terms "treat," "treating," or "treatment" refers to both therapeutic treatment and prophylactic or preventative measures for an HIV infection or an HIV or AIDS mediated disease or condition. To "treat disease" or use for "therapeutic treatment" refers to administering treatment to a subject already suffering from a disease to improve the subject's condition. Treatment can include modulating or inhibiting the disease or condition, (e.g., arresting its development); relieving the disease or condition, (e.g., causing regression of the disease or condition); reduction in viral load; or relieving and/or alleviating the disease or condition or the symptoms resulting from the disease or condition with or without addressing the underlying disease or condition. To "prevent disease" refers to prophylactic treatment of a subject who is not yet ill, but who is susceptible to, or otherwise at risk of, developing a particular disease. Prophylactic treatment can also include the prevention of one or more symptoms associated with HIV or AIDS. Thus, in the claims and embodiments, treating includes the administration to a mammal either for therapeutic or prophylactic purposes.

By "subject" is meant a mammal, including, but not limited to, a human or non-human mammal, such as a simian, bovine, canine, equine or feline.

The terms "resistant," "resistance," and "resistant HIV," as used herein, refer to HIV virus demonstrating a reduction in sensitivity to a particular drug. A mammal infected with HIV that is resistant to a particular anti-HIV agent or combination of agents usually manifests an increase in HIV viral load despite continued administration of the agent or agents. Resistance may be either genotypic, meaning that a mutation in the HIV genetic make-up has occurred, or phenotypic, meaning that resistance is discovered by successfully growing laboratory cultures of HIV virus in the presence of an anti-HIV agent or a combination of such agents.

The terms "co-administration," "co-administering," "co-administer," "co-administered," or "combination therapy" as used herein, refer to the administration of a combination of at least a first agent and a second agent and can include two or more agents. Such co-administration can be performed such that two or multiple agents are part of the same composition or part of the same unitary dosage form, or in separate compositions or dosage forms. Co-administration also includes administering a first agent and a second agent, or more than two agents separately and as part of the same therapeutic regimen. The agents, if administered separately, need not necessarily be administered at essentially the same time, although they can be if so desired. Thus, co-administration includes, for example, administering a first agent and a second agent as separate dosages or dosage forms, but at the same time. Co-administration also includes separate administration at different times (e.g., sequentially or alternating one agent with the other) and in any order.

The term "compound of the present invention" refers to compounds of formulas I and Ia, as well as those in the Examples that follow, and includes pharmaceutically acceptable salts of these compounds.

The abbreviations used herein refer to the following:

| Abbreviation | Meaning |
| --- | --- |
| AcOH | Acetic acid |
| Ar | Argon |
| AIDS | Acquired Immunodeficiency Syndrome |
| AZT | 3-Azido-3-deoxythymine (Zidovudine) |
| BSA | Bovine serum albumin |
| DMF | Dimethylformamide |
| DNA | Deoxyribonucleic acid |
| EtOH | Ethyl alcohol |
| g | gram |
| HPLC | High pressure liquid chromatography |
| HIV-1, -2 | Human immunodeficiency virus type 1, type 2 |
| HTLV-I, -II | Human T-cell lymphotropic virus type I, type II |
| M | Molar |
| MeOH | Methyl alcohol |
| mg | Milligram |
| mp | Melting point |
| min | Minute |
| mL | Milliliter |
| mmol | Millimole |
| nM | Nanomolar |
| RNA | Ribonucleic acid |
| THF | Tetrahydrofuran |

DETAILED DESCRIPTION

Pharmaceutical compositions contemplated herein comprise at least one compound of the present invention, including pharmaceutically acceptable salts, solvate or formulations thereof, with a pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol, liposomes and lanolin.

It is understood by those skilled in the art that the compounds of the present invention, salts, or solvates thereof may exist in different crystal or polymorphic forms that are within the scope of the present invention and specified formulas.

Compounds of the present invention that are basic may be prepared as a salt using suitable methods known in the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

Basic compounds of the present invention can form a variety of salts with various inorganic and organic acids. Although such salts must be pharmaceutically acceptable for administration to animals, it is common practice to first isolate the compound of the present invention as a pharmaceutically unacceptable salt and then convert to a free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol.

Compounds of the present invention that are acidic may be prepared as a salt using suitable methods known in the art, including treatment of the free acid with an inorganic or organic base, such as an amine (primary, secondary, or tertiary); an alkali metal or alkaline earth metal hydroxide; or the like. Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

Acidic compounds of the present invention can form base salts with various pharmacologically acceptable cations. Examples of such salts include the alkali metal or alkaline-earth metal salts and particularly, the sodium and potassium salts, which can be prepared using conventional techniques. The chemical bases suitable as reagents in preparing the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same mariner as before. In either case, stoichiometric quantities of reagents are preferably employed in order to ensure completeness of reaction and maximum yields of the desired final product.

To treat or prevent diseases or conditions caused or mediated by HIV, a pharmaceutical composition, comprising at least one of the compounds of the present invention, is administered in a pharmaceutically acceptable formulation prepared by combining a therapeutically effective amount of the compound with one or more pharmaceutically suitable carriers including diluents, excipients and auxiliaries that facilitate processing of the active compounds into a pharmaceutically acceptable formulation. Carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such: as Labrasol®, Gelucire® or the like, or formulator, such as CHIC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0-60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Pharmaceutical preparations for oral use can be obtained using a solid excipient in an admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

The pharmaceutical compositions, comprising the compounds of the present invention may also contain suitable solid- or gel-phase carriers or excipients. These carriers and excipients may provide marked improvement in the bioavailability of poorly soluble drugs. Examples of such carriers or excipients include calcium carbonate, calcium, phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used. Further, the pharmaceutical composition may be incorporated into a skin patch for delivery of the drug directly onto the skin. Methods of prophylaxis and treatment, their dosage levels and requirements may be selected by those of ordinary skill in the art from available methods and techniques.

The compounds of this invention may be modified by appending appropriate functionalities to enhance selective biological properties. Such modifications are known in the art and include those which increase biological penetration into a given biological system (e.g., blood, lymphatic system, central nervous system), increase oral bioavailability, increase solubility to allow administration by injection, alter metabolism or alter rate of excretion (*Pharmacokinetic Optimization in Drug Research*, Testa, B. et al, 2001, Wiley-VCH, VCHA).

The pharmaceutical compositions of this invention may be administered orally, intravenously, parenterally, by inhalation spray, topically, rectally, nasally, buccally, vaginally, or via an implanted reservoir and are preferably administered orally or parenterally. The pharmaceutical compositions of this invention may contain any conventional non-toxic pharmaceutically acceptable carriers, adjuvants or vehicles. The term "parenteral" or "parenterally" as used herein includes sub-cutaneous, intra-cutaneous, intra-venous, intra-muscular, intra-articular, intra-synovial, intra-sternal, intra-thecal, intra-lesional and intracranial injection or infusion techniques.

For intravenous administration, pharmaceutical compositions of the invention may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solutions. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. Pharmaceutical compositions of the invention may be orally administered in any orally acceptable dosage form including, but not limited to, capsules, tablets, and aqueous suspension and solutions. In the case of tablets for oral and carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or coloring agents may be added.

Pharmaceutical compositions of the invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols. The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

It will be appreciated that the actual dosages of the agents of this invention will vary according to the particular agent being used, the particular composition formulated, the mode of administration, and the particular site, host, and disease being treated. Those skilled in the art using: conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals, preferably between 0.01 and about 25 mg/kg body weight per day, and more preferably between about 0.5 and about 25 mg/kg body weight per day of the active ingredient compound useful in the prevention and treatment of viral infection, including HIV infection.

Furthermore, the pharmaceutically acceptable formulations of the present invention may contain a compound of the present invention, or a pharmaceutically acceptable salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Additionally, the pharmaceutically acceptable formulations of the present invention may contain a compound of the present invention, or a pharmaceutically acceptable salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The pharmaceutical compositions of this invention may be administered as a continuous infusion, once per day, multiple times per day (e.g., from about 1 to about 5 times per day), once per week, twice per week, three times per week, every other day, every other week or as determined by the practicing clinician. Such administration can be used as a chronic or acute therapy. The amount of active ingredient that may be combined with the carrier materials to produce a single dosage form will vary depending upon the patient treated and the particular mode of administration. A typical preparation will contain from about 5% to about 75% active compound (w/w). Preferably, such preparations contain from about 20% to about 50% active compound.

Upon improvement of a patient's condition, a maintenance dose of a compound, composition or combination of this invention may be administered if necessary or desired. Subsequently, the dosage or frequency of administration, or both, may be reduced, as a function of the symptoms, to a level at which the improved condition is retained or maintained. When the symptoms have been alleviated to the desired level, treatment should cease, at least in principle. Patients may, however, require intermittent treatment on a long-term basis, upon any recurrence of disease symptoms, especially for AIDS.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

With respect to the compounds of the present invention, the particular pharmaceutical formulation, the dosage, and the number of doses given per day to a mammal requiring such treatment, are all choices within the knowledge of one of ordinary skill in the art and can be determined without undue experimentation. For example, see "Guidelines for the Use of Antiretroviral Agents in HIV-1 Infected Adults and Adolescents," United States Department of Health and Human Services, available at http://www.aidsinfo.nih.aov/guidelines.

The compounds of this invention are also useful as commercial reagents which effectively bind to HIV integrase. As commercial reagent, the compounds of this invention, and their derivatives, may be used to block integration of a target DNA molecule by integrase, or may be derivatized to bind to a stable resin as a tethered substrate for affinity chromatography applications. These and other uses which characterize commercial integrase inhibitors will be evident to those of ordinary skill in the art.

The compounds of the present invention can be used alone (monotherapy) or administered in combination with one or more other HIV-inhibiting agents including but not limited to additional compounds of the invention or entry inhibitors, protease inhibitors, reverse transcriptase inhibitors, fusion inhibitors, and integrase inhibitors, examples of which are described below and known to the skilled artisan.

In one example, the compounds of the invention can be used in combination with an additional HIV integrase inhibitor. Compounds that effectively inhibit HIV integrase may provide improved antiviral agents and compositions for treating HIV infection (Wai, J. S. et al., J. Med. Chem. 43:4923-4926 (2000); Grobler, J. et al., PNAS 99: 6661-6666 (2002); Pals, G. C. G. et al., J. Med. Chem. 45: 3184-3194 (2002); Young, S. D., Curr. Opin. Drug Disc. & Devel. 4(4): 402-410 (2001); Godwin, C. G. et al., J. Med. Chem. 45: 3184-3194 (2002); Opar, A. Nature Reviews, Drug Discovery, vol. 6, p. 258-259, (2007)). Other integrase inhibitors known in the art include those disclosed in patent applications WO200510305, WO2004039803, WO2004067531, WO2008/048538, WO2003082881 WO2007000043, and.

The compounds of this invention may be administered in combination with antiviral agents which target other steps in the retroviral replication cycle. For example, the co-administered antiviral agent can be one that targets early events in the life cycle of the virus, such as cell entry, reverse transcription and viral DNA integration into cellular DNA. Antiviral agents targeting such early life cycle events include, didanosine (ddI), zalcitabine (ddC), stavudine (d4T), zidovudine (AZT), polysulfated polysaccharides, sT4 (soluble CD4)—which blocks attachment or adsorption of the virus to host cells—and other compounds which block binding of virus to CD4 receptors on CD4-bearing T-lymphocytes. Other retroviral reverse transcriptase inhibitors, such as derivatives of AZT, may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformiate, eflornithine, ribavirin, acyclovir, alpha interferon and trimenotrexate. Additionally, non-ribonucleoside inhibitors of reverse transcriptase, such as TIBO, nevirapine or delavirdine, may be used to potentiate the effect of the compounds of this invention, as may viral uncoating inhibitors, inhibitors of trans-activating proteins such as tat or rev, or inhibitors of the viral protease. These compounds may also be co-administered with other inhibitors of HIV integrase.

Combination therapies according to this invention may exert an additive or combined inhibitory effect on HIV replication because each therapeutic agent of the combination acts on a different site of HIV replication or a synergistic effect. For example, the use of such combination therapies also advantageously enables a reduction in the dosage of each anti-retroviral agent, compared to administration of either agent alone as a monotherapy, while providing an equivalent or better therapeutic or prophylactic effect. Administration of lower doses of each therapeutic agent often reduces or even eliminates side effects or toxicity relative to monotherapy. Furthermore, combination therapies reduce the potential for the development of viral resistance to the agents administered compared to monotherapy.

Preferred combination therapies include the administration of a compound of this invention with AZT, 3TC, ddI, ddC, d4T, combivir, ziagen, sustiva, nevirapine and delavirdine. The compounds of this invention may also be co-administered with other HIV protease inhibitors such as saquinavir, indinavir, nelfinavir, ritonavir and amprenavir. Combination of the compounds of this invention with such protease inhibitors may increase the therapeutic or prophylactic against various HIV viral mutants, HIV quasi species or other closely related viruses.

The compounds of this invention may be administered in combination with nucleoside or non-nucleoside retroviral reverse transcriptase inhibitors (e.g. derivatives of AZT or HIV aspartyl protease inhibitors) HIV-entry inhibitors, HIV integrase inhibitors, immuno-modulators (e.g., bropirimine, anti-human alpha interferon antibody, IL-2, GM-CSF, methionine enkephalin, interferon alpha, diethyldithiocarbante, tumor necrosis factor, naltrexone and rEPO); antibiotics (e.g., pentamidine isethionate), vaccines or a combination thereof.

Administration of the compounds of this invention in combination therapies with other agents to patients may be sequential or concurrent. Furthermore, pharmaceutical or prophylactic compositions of this invention may include a combination of an integrase inhibitor compound of the present invention and another therapeutic or prophylactic agent or HIV-inhibiting agent. Additional examples of agents useful for treating AIDS and HIV and suitable for combination therapies with the compounds of this invention are listed in Tables 1 and 2 below.

TABLE 1

| Antiviral Drug | Manufacturer | Indication |
|---|---|---|
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon | Glaxo Wellcome | Kaposi's sarcoma |
| HIV in combination w/Retrovir | | |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/Novartis | HIV infection, AIDS, ARC |
| BMS-234475 (CGP-61755) (protease inhibitor) | Bristol-Myers Squibb/Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside RT inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |

TABLE 1-continued

| Antiviral Drug | Manufacturer | Indication |
|---|---|---|
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, combination with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (RT inhibitor) | Gilead | HIV infection, AIDS |
| Combivit ® (RT inhibitor) | GSK | HIV infection, AIDS |
| abacavir succiante (or Ziagen ®) (RT inhibitor) | GSK | HIV infection, AIDS |
| Reyataz ® (atazanavir) | Bristol-Myers Squibb | HIV infection, AIDS |
| Fuzeon (Enfuvirtide, T-20) | Rocheh/Trimeris | HIV infection, AIDS, viral fusion inhibitor |
| Trizivir ® | GSK | HIV infection, AIDS |
| Kaletra ® | Abbott | HIV infection, AIDS, ARC |

TABLE 2

| Immuno-Modulator | Manufacturer | Indication |
|---|---|---|
| Acemannan | Carrington Labs Inc. (Irving, TX) | AIDS, ARC |
| Alpha-2 Interferon | Schering Plough | Kaposi's sarcoma w/AZT, AIDS |
| AS-101 Bropirimine | Wyeth-Ayerst/Pharmacia Upjohn | AIDS, advanced AIDS |
| CL246,738 | American Cyanamid Lederle Labs | AIDS, Kaposi's sarcoma |
| EL10 | Elan Corp PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute/ Sandoz | AIDS |
| Granulocyte Macrophage Colony Stimulating Factor | Hoechst-Roussel\Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche/Immunex | AIDS, ARC, HIV, in combination w/AZT |
| IL-2 Interleukin-2 (aldeslukin) | Chiron | AIDS, increase in CD4 cell counts |
| IMERG-2 | Imreg (New Orleans, LA) | AIDS, Kaposi's sarcoma, ARC, PGL |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| Imuthiol Diethyl Dithio Carbamate | Merieux Institute | AIDS, ARC |
| Interferon Alfa 2a | Hoffman-La Roche | Kaposi's sarcoma, AIDS, in combination w/AZT ARC |
| Methionine-Enkephalin | TNI Pharmaceutical (Chicago, IL) | AIDS, ARC |
| MTP-PE Muramyl-Tripeptide Granulocyte Colony Stimulating Factor | Ciba-Geigy Corp./Amgen | Kaposi's sarcoma AIDS in combination w/AZT |
| rCD4 Soluble Human CD4 rCD4-IgG | Genentech | AIDS, ARC Recombinant AIDS, ARC hybrids |
| Recombinant Soluble Human CD4 | Biogen | AIDS, ARC |
| Remune | Immune Response Corp. | Immunotherapeutic |

Anti-infectives that may be used in combination with the compounds of the present invention include, but are not limited to, atovaquone, azithromycin, clarithromycin, trimethoprim, trovafloxacin, pyrimethamine, daunorubicin, clindamycin with primaquine, fluconazole, pastill, ornidyl, eflomithine pentamidine, rifabutin, spiramycin, intraconazole-R51211, trimetrexate, daunorubicin, recombinant human erythropoietin, recombinant human growth hormone, megestrol acetate, testerone, and total enteral nutrition.

Antifungals that may be used in combination with the compounds of the present invention include, but are not limited to, anidulafungin, C31G, caspofungin, DB-289, fluconzaole, itraconazole, ketoconazole, micafungin, posaconazole, and voriconazole.

Other compounds that may be used in combination with the compounds of the present invention include, but are not limited to, acmannan, ansamycin, LM 427, AR177, BMS-232623, BMS-234475, CI-1012, curdlan sulfate, dextran sulfate, STOCRINE EL10, hypericin, lobucavir, novapren, peptide T octabpeptide sequence, trisodium phosphonoformate, probucol, and RBC-CD4.

In addition, the compounds of the present invention may be used in combination with anti-proliferative agents for the treatment of conditions such as Kaposi's sarcoma. Such agents include, but are not limited to, inhibitors of metallomatrix proteases, A-007, bevacizumab, BMS-275291, halofuginone, interleukin-12, rituximab, paclitaxel, porfimer sodium, rebimastat, and COL-3.

Compounds of the present invention may be administered in combination with an additional agent or pharmaceutical composition that increases the bioavailability or slows the metabolism of the compounds. Agents or pharmaceutical compositions that may increase the bioavailablity or slow the metabolism of the compounds herein include inhibitors of at least one isoform of the cytochrome P450 (CYP450) enzymes, preferably CYP1A2, CYP2d6, CYP2C9, CYP2C19 and CYP3A4. Suitable agents that may be used to inhibit CYP 3A4 include, but are not limited to, delavirdine and ritonavir. Such combinations may be administered such that a compound or compounds of the present invention are present in a single formulation or in the form of separate formulations that may be administered sequentially with an appropriate period of time in between or simultaneously. The choice of whether to include the compound or compounds of the present invention in the same formulation as the additional agent or agents is within the knowledge of one of ordinary skill in the art.

Preparation of Intermediates and Compounds

Fifteen general approaches (synthetic schemes) were use to prepare the compounds of the present invention.

The first approach (Scheme 1) starts from pyridoxine which is modified to produce Intermediate I using methodologies described in Paul et al. J. Med. Chem., 1977, 20 p 745. Intermediate I is modified to produce a protected hydroxamic acid (II) by ester displacement and the isopropylidene protecting group of II is removed by mild hydrolysis with formic acid to give intermediate III. Selective oxidation of the 5-CH2OH group of III is effected using Manganese dioxide and III spontaneously cyclizes to the corresponding lactone intermediate (IV). IV may be substituted, as illustrated in Scheme 1, with an amine producing the corresponding amide V. Protecting groups are removed using hydrogenolysis giving the desired product VI.

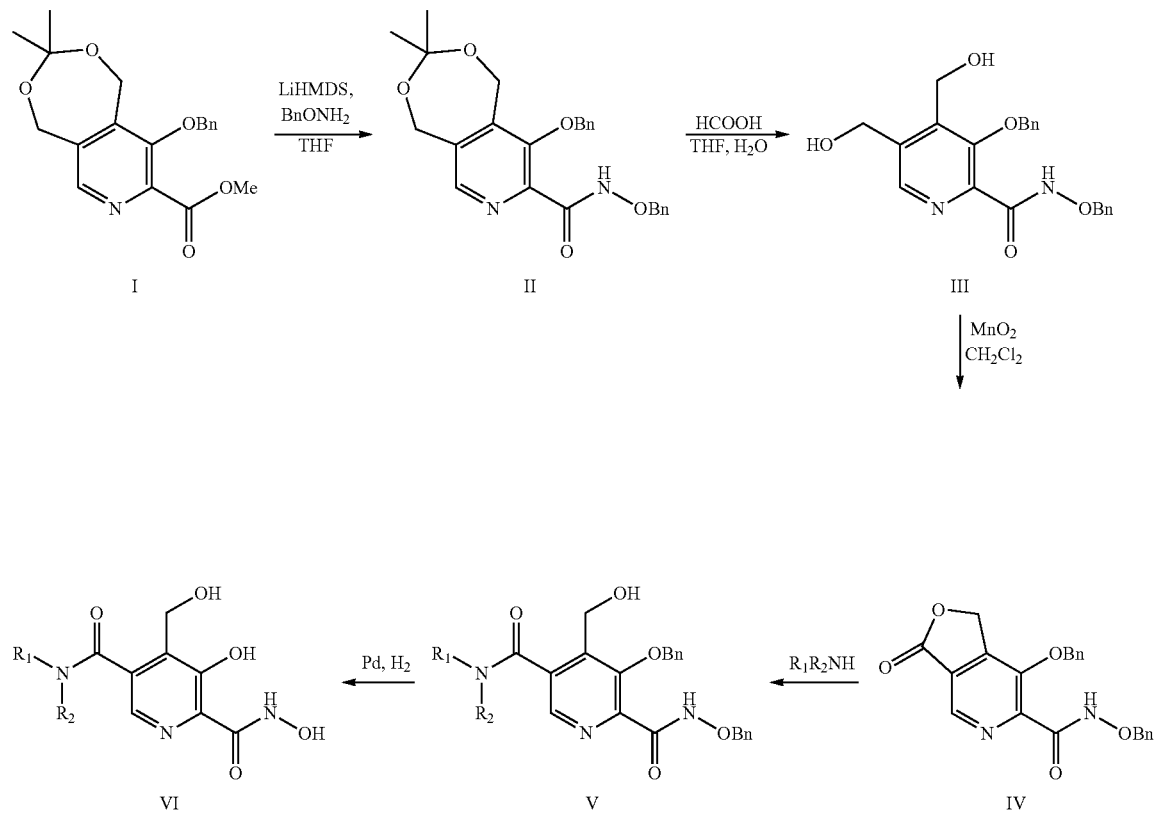

The second approach (Scheme 2 below) starts with intermediate VIII. VIII is obtained from Intermediate I (Scheme 1) using steps 2 and 3 of Scheme 1; removal of the isopropylidene protecting group by hydrolysis (as step 2 of scheme 1) followed by selective oxidation of 5-CH2OH with MnO2 (as step 3 of scheme 1). VIII is then hydrolysed using potassium trimethylsilanoate to generate intermediate VII. VII is transformed to intermediate IV using O-protected hydroxylamine and aryl sulfonyl halide. VI is substituted with an amine producing the corresponding amide V and the protecting groups are removed by hydrogenolysis (VI). Further hydrogenation yields the desired product IX.

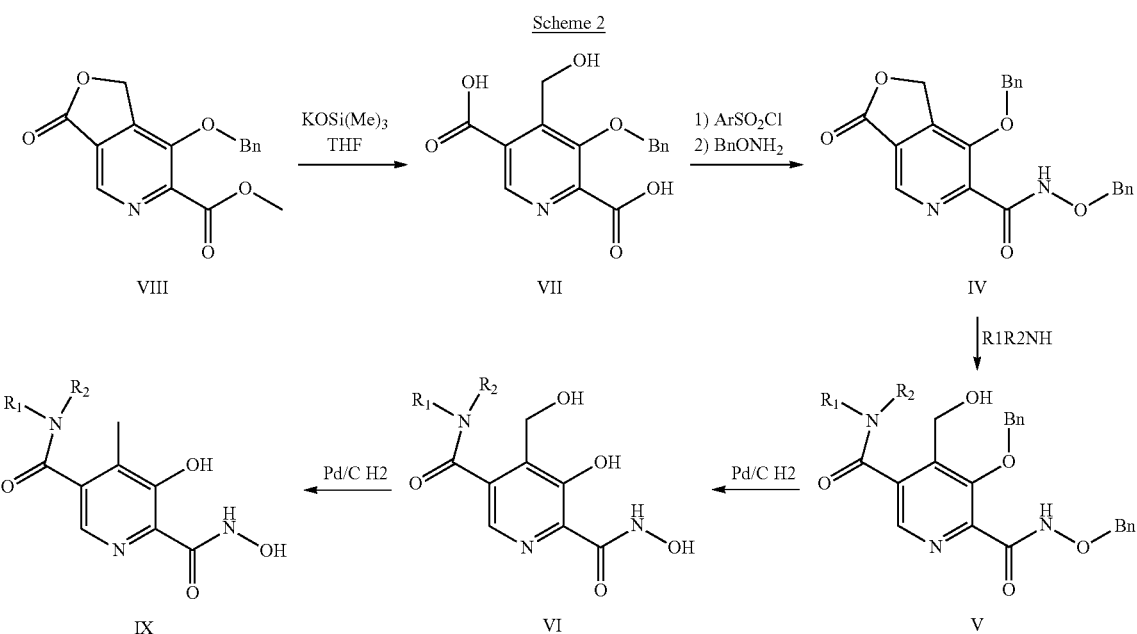

Scheme 2

The third approach (Scheme 3) starts with the protected pyro as in scheme I and generates the lactol IV by controlled oxidation with MnO2. The lactol (IV) is readily converted to the amine X through reductive amination and further reduction by catalytic hydrogenation generating compound XI.

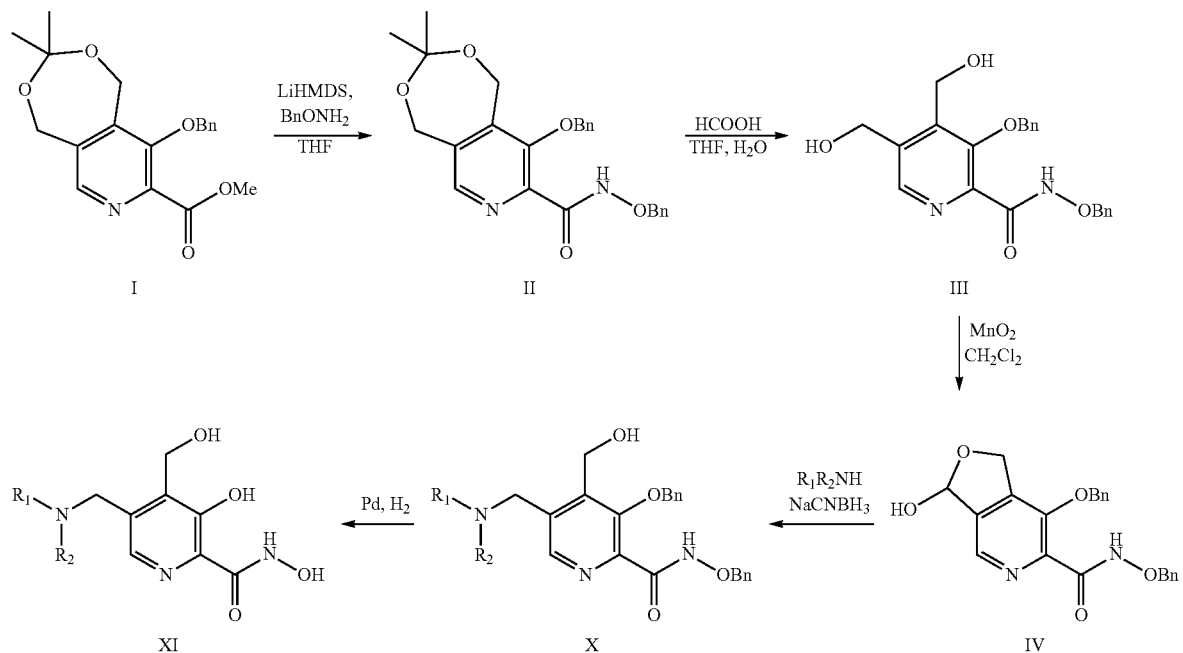

Scheme 3

The fourth approach (Scheme 4) starts from pyridoxine and generates intermediate XIII in a manner similar to that described in Adamczyk M. et al, Tetrahedron, 56, 2000 p 2379. XIII is then oxidized selectively at the 2 methyl group through an N-oxide intermediate XIV followed by rearrangement to the alcohol XV. Further stepwise oxidation yields an aldehyde (XVI) followed by an ester (XVII). Hydrolysis of the isopropylidene of XVII and displacement of the ester XVIII with hydroxylamine yields the desired product compound XIX.

Scheme 4

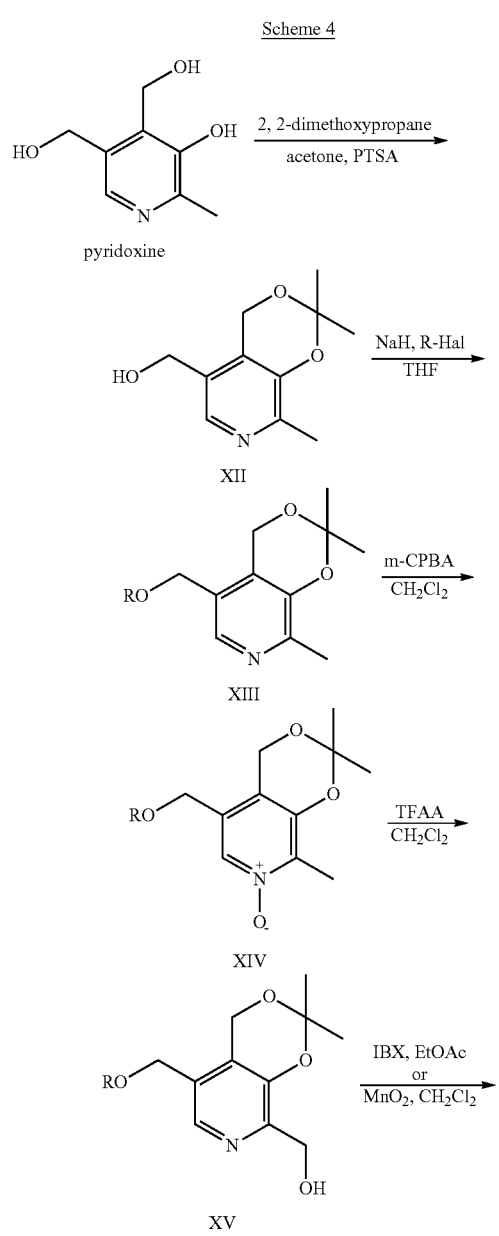
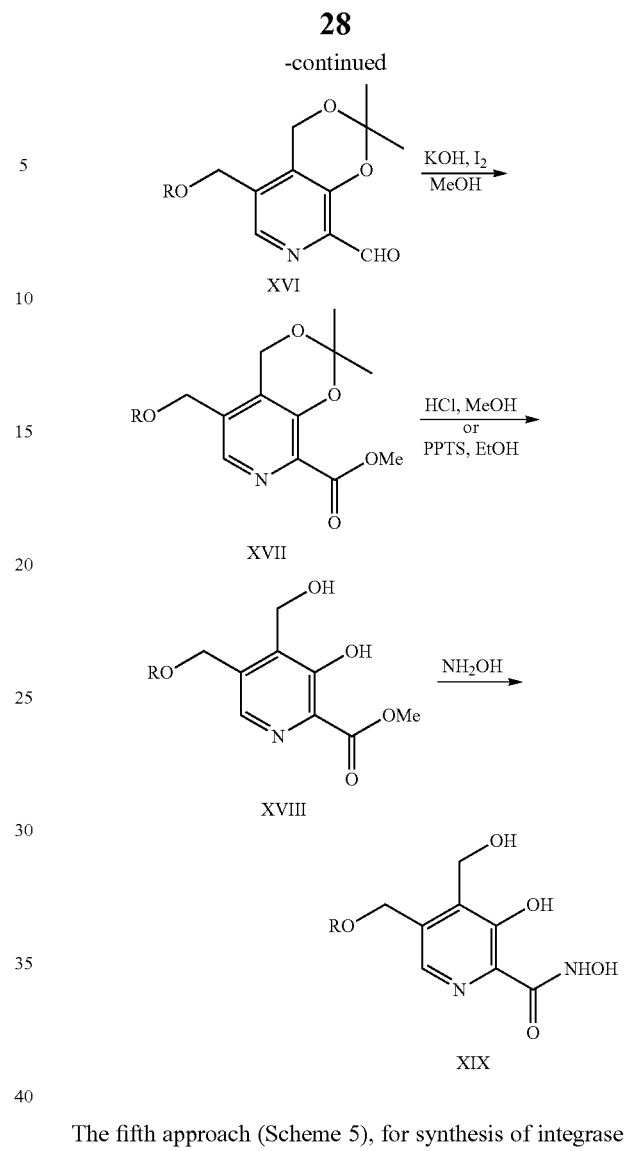

The fifth approach (Scheme 5), for synthesis of integrase inhibitor compounds of invention, starts from the intermediate XVII of scheme 4. XVII is hydrolysed to the acid XX and XX is subsequently coupled to O-benzylhydroxylamine to give XXI. XXI may be subjected to hydrogenation yielding the product compound XXIII or to hydrolysis yielding the product compound XXII.

Scheme 5

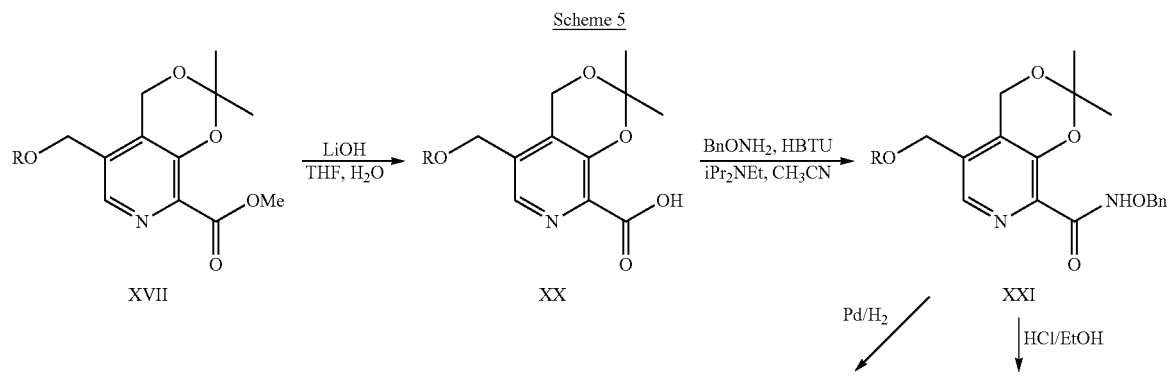

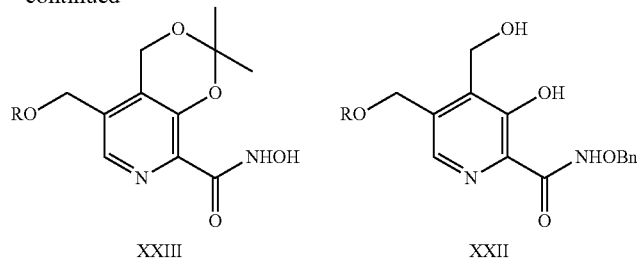

XXIII          XXII

The sixth approach (Scheme 6) begins from 7-(benzyloxy)-6-methylfuro[3,4-c]pyridin-3(1H)-one; intermediate XXIV (Paul, B., Korytnyk, W. J. Het. Chem., 1976, v13, p 701). XXIV is reacted with amine yielding intermediate XXV. XXV is then alkylated to XXVI and oxidized selectively at the 2 position through an N-oxide rearrangement, as described in Scheme 4, to yield intermediate XXX. XXX is then displaced and hydrogenated to yielding the desired product compound XXXII.

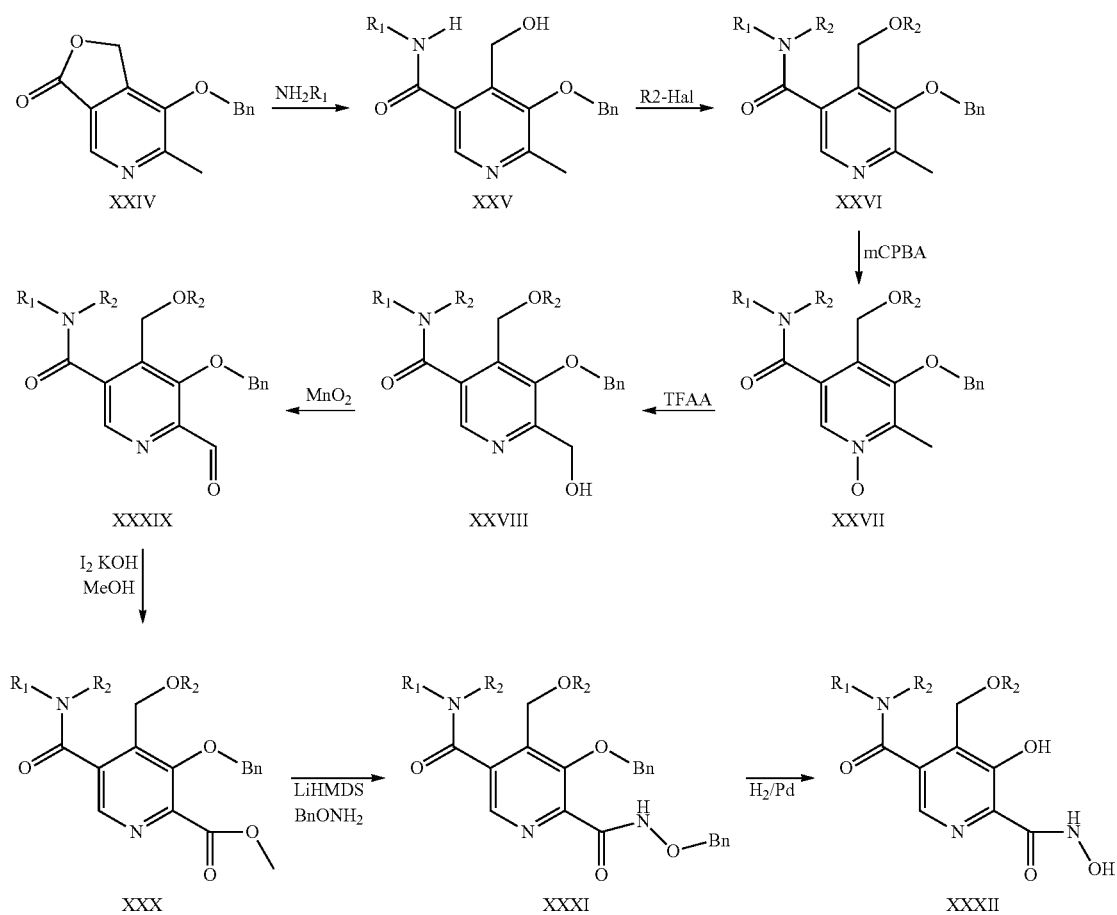

Scheme 6

The seventh approach begins from an analogue of compound XVII of scheme 5, XVIIe (17e below), which is acidified in anhydrous conditions to yield product XXXIII. This product is oxidized to give an intermediate aldehyde XXXIV and further oxidized, under controlled conditions, to give the carboxylic acid intermediate XXXV.

Scheme 7

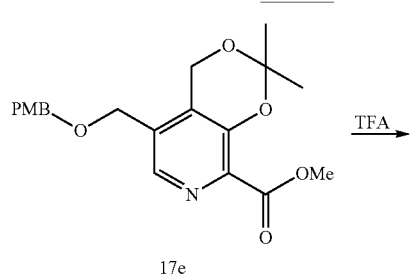

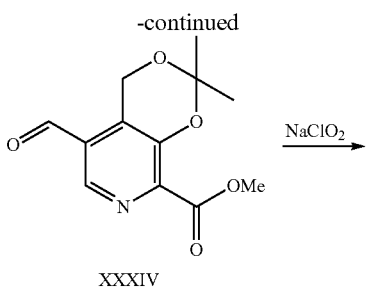

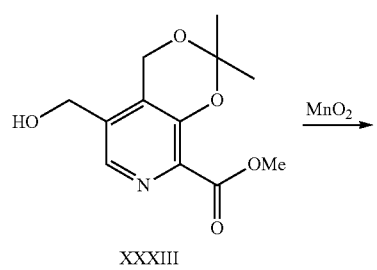

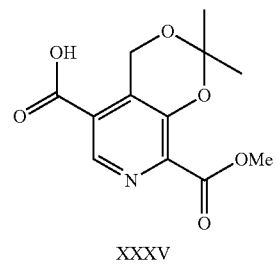

The eighth approach consists of reductive amination the intermediate XXXIV with either a primary or secondary amines to obtain XXXVI or XXXVII respectively. XXXVII analogues may be obtained by another reductive amination of aldehydes with XXXVI. Treatment of XXXVI and XXXVII with aqueous acids yield the intermediate XXXVIII which can be further reacted with hydroxylamine solutions to give product XXXIX.

Scheme 8

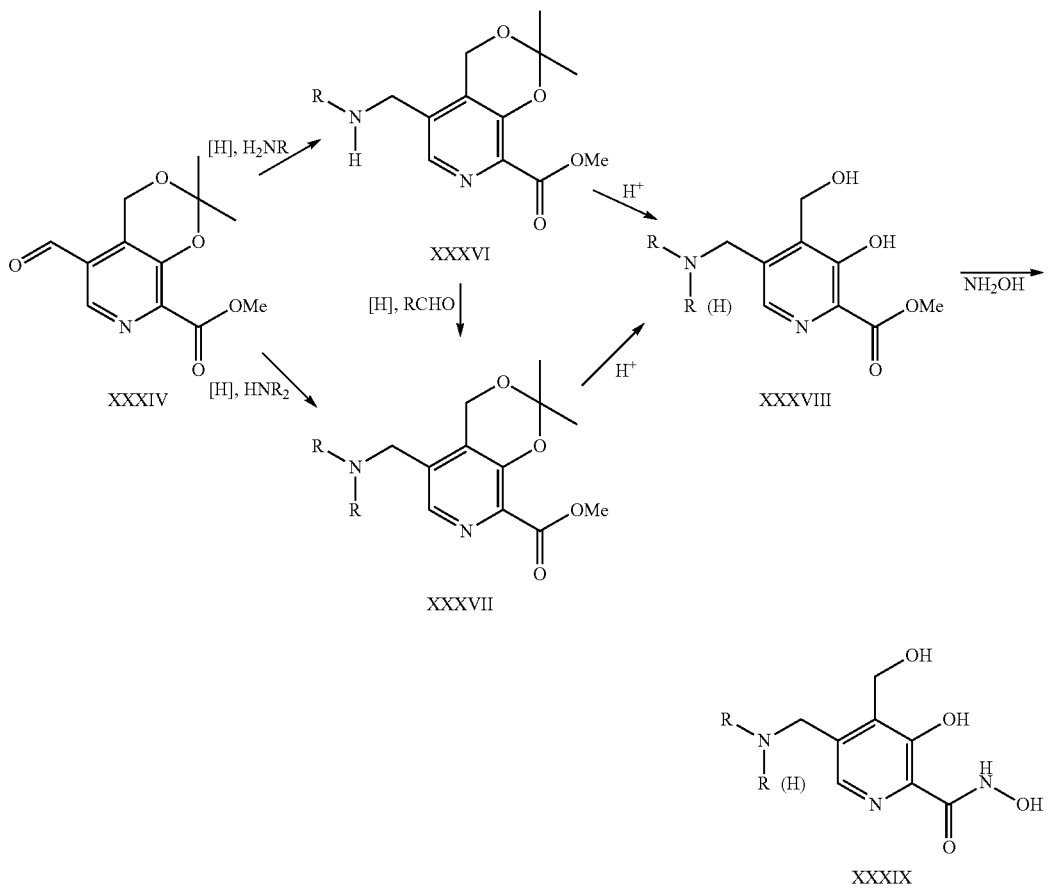

The ninth approach consists of controlled oxidation of intermediate XXXIV producing carboxylic acid XXXV. A Curtius rearrangement using diphenylphosphorylazide (DPPA) in the presence of benzyl alcohol affords the intermediate XL. XL may be deprotected by hydrogenation to yield the amine XLI which may be reacted with activated carboxylic acids, acyl halides, isocyanates, chloroformated and other electrophiles to yield intermediate XLII. These may then be converted to product XLIII by exposure to formic acid, followed by reaction with hydroxylamine.

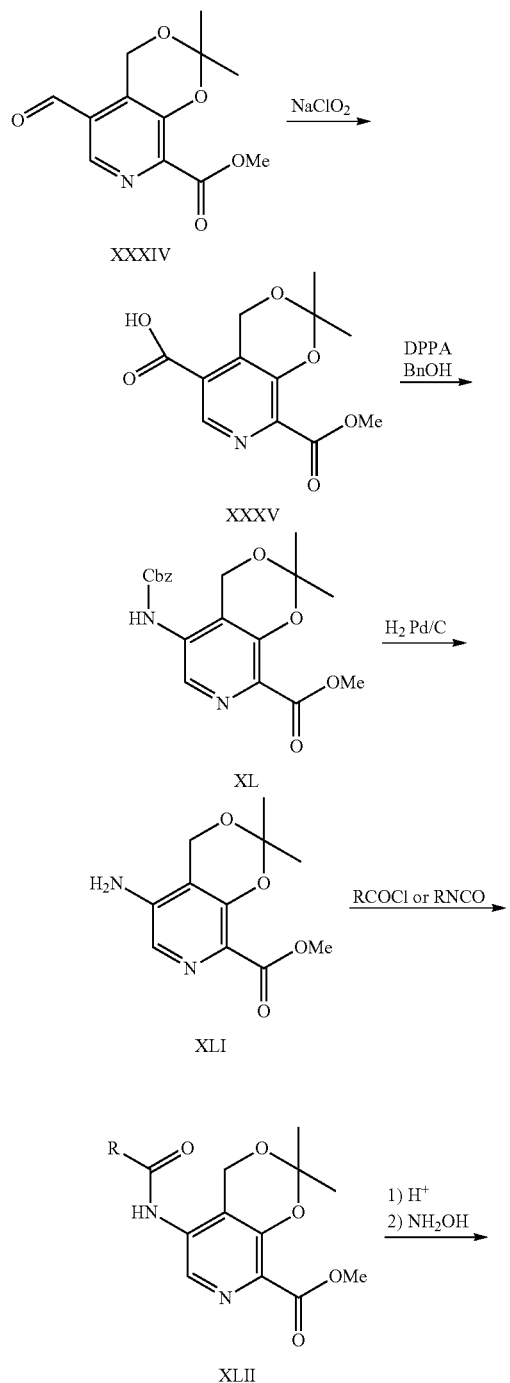

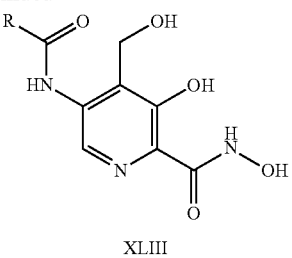

The tenth approach begins with intermediate XXXIII (scheme 7) which is reacted in a Mitsunobu reaction with phenols to yield ether XLIV. XLIV is exposed to aqueous formic acid, and subsequently reacted with hydroxylamine to yield product XLV.

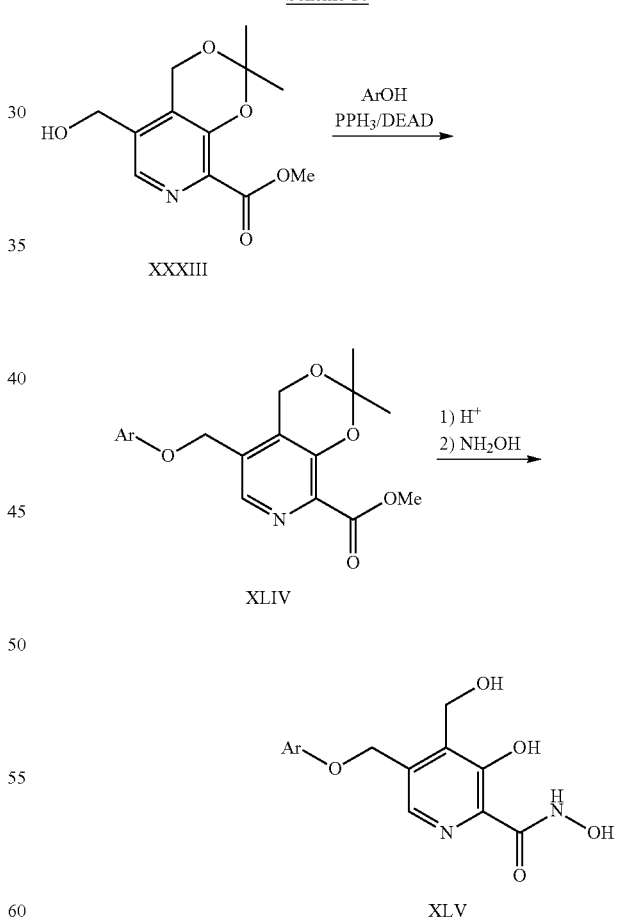

The eleventh approach consists of acylation of compound XXXVI by activated carboxylic acids, acyl halides, chloroformates isocyanates and other electrophiles to obtain compound XLVI. XLVI is then exposed to aqueous formic acid and reacted with hydroxylamine to yield product XLVII.

Scheme 11

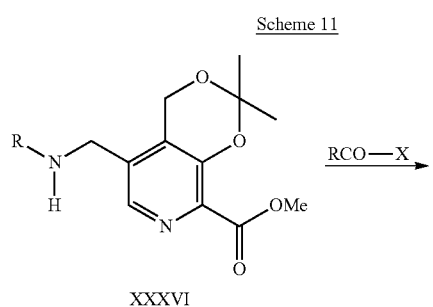

The twelfth approach begins with a Wittig reaction of intermediate XXXIV to yield alkenes of the form XLVII. XLVII is then hydrogenated producing saturated alkanes which are exposed to aqueous formic acid and subsequently reacted with hydroxylamine to yield product L.

Scheme 12

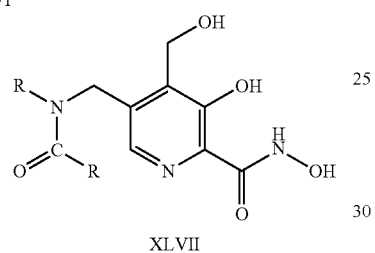

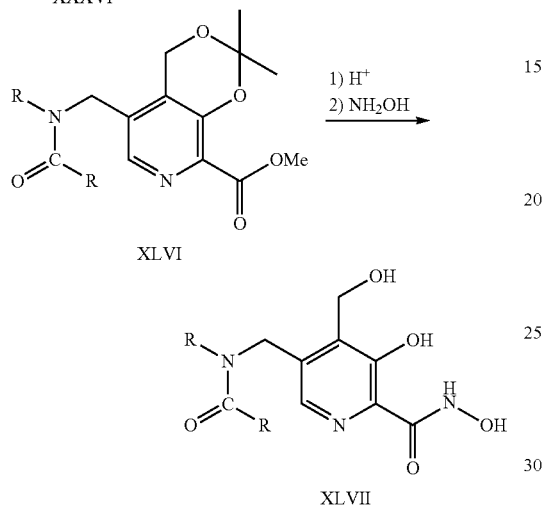

The thirteenth approach begins with intermediate XXXIII and reaction of XXXIII with methane sulfonyl chloride to yield the reactive intermediate alkyl chloride LI. LI is immediately and cautiously reacted with a mercaptan to yield the thioether LII. Reaction of LII with excess peroxide mCPBA yields a sulfone-N-Oxide intermediate LIII, which upon exposure to trifluoroacetic anhydride rearranges to products LIV. The intermediate alcohol may the be oxidized in a stepwise manner, to LV esters, which are then exposed to aqueous formic acid and reacted with hydroxylamine to yield products LVI.

Scheme 13

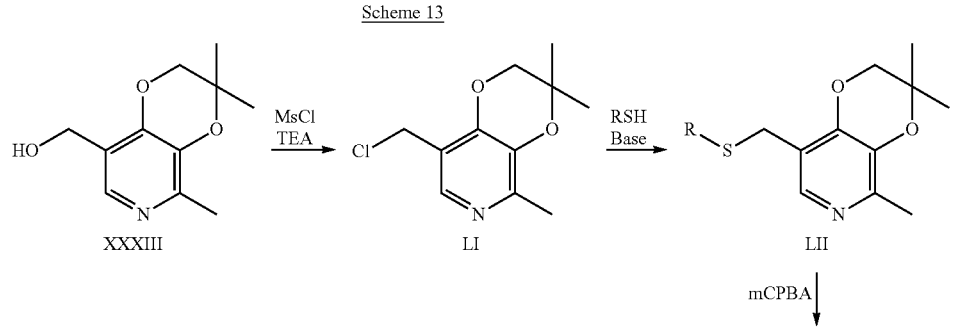

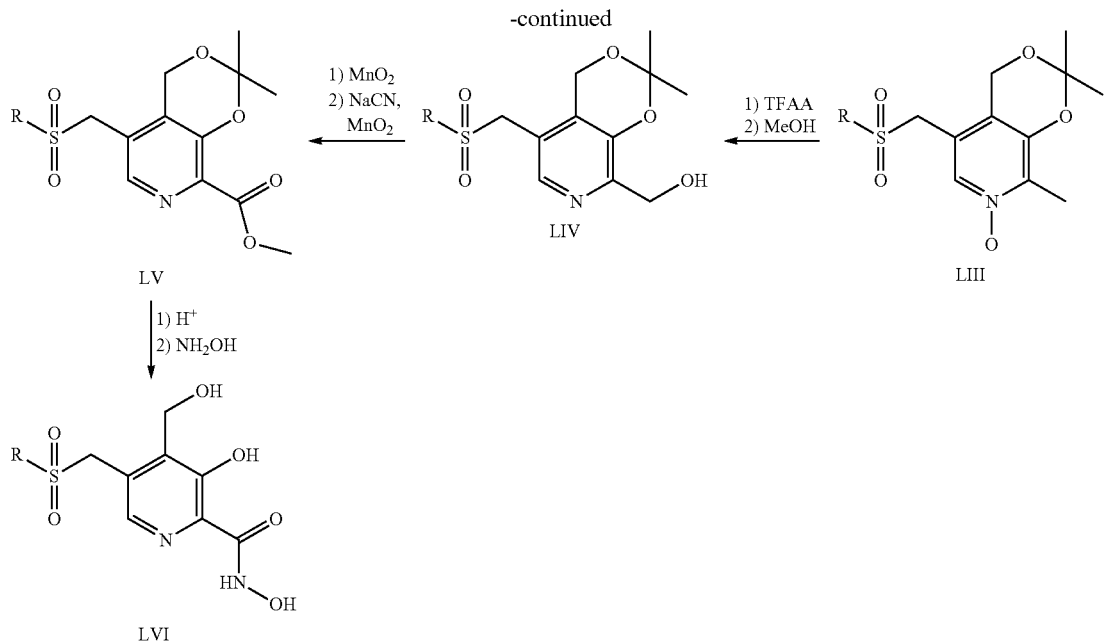

The fourteenth approach consists of first deprotecting intermediate XXIV through catalytic hydrogenation to yield LVII. LVII is then alkylated with trimethylsilyl diazomethane to the methoxy derivative LVIII. Reaction of the lactone with a primary amine followed by protection of the liberated alcohol with tert-butyl diphenylsilyl chloride gives intermediates LIX. Reaction of LIX with peroxide, mCPBA, yields intermediates LX. LX can be rearranged with trifluoroacetic anhydride yeilding LXI and oxidized in stepwise fashion to LXII. A protected hydroxylamide is formed from by first reacting O-benzylhydroxylamine hydrochloride with several equivalents of lithium hexamethyldisilazane and reacting this with intermediate LXII, quenched and exposed to fluoride ions, yielding LXIII. Catalytic hydrogenation of LXIII yields product LXIV.

Scheme 14

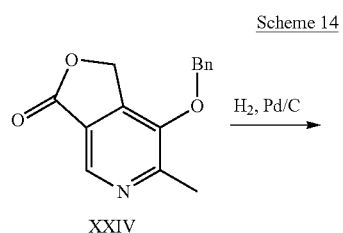

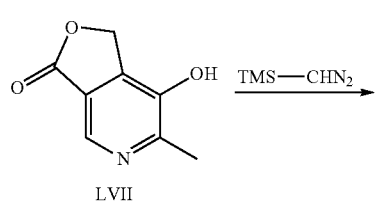

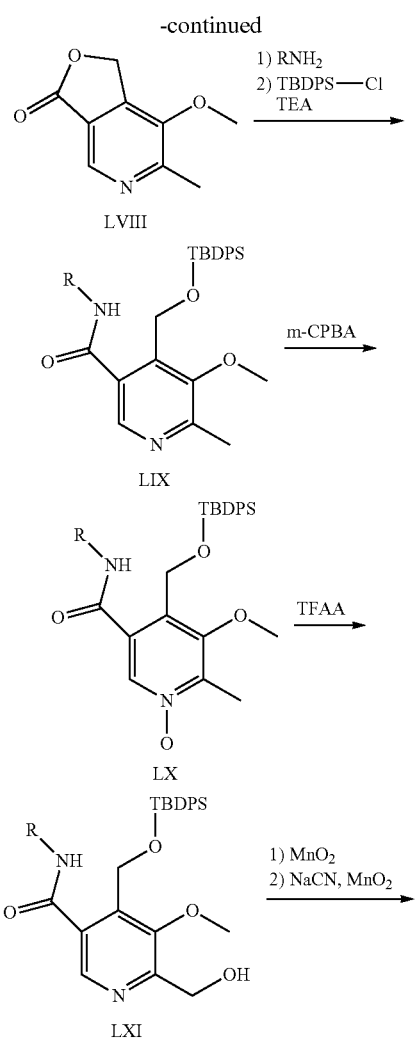

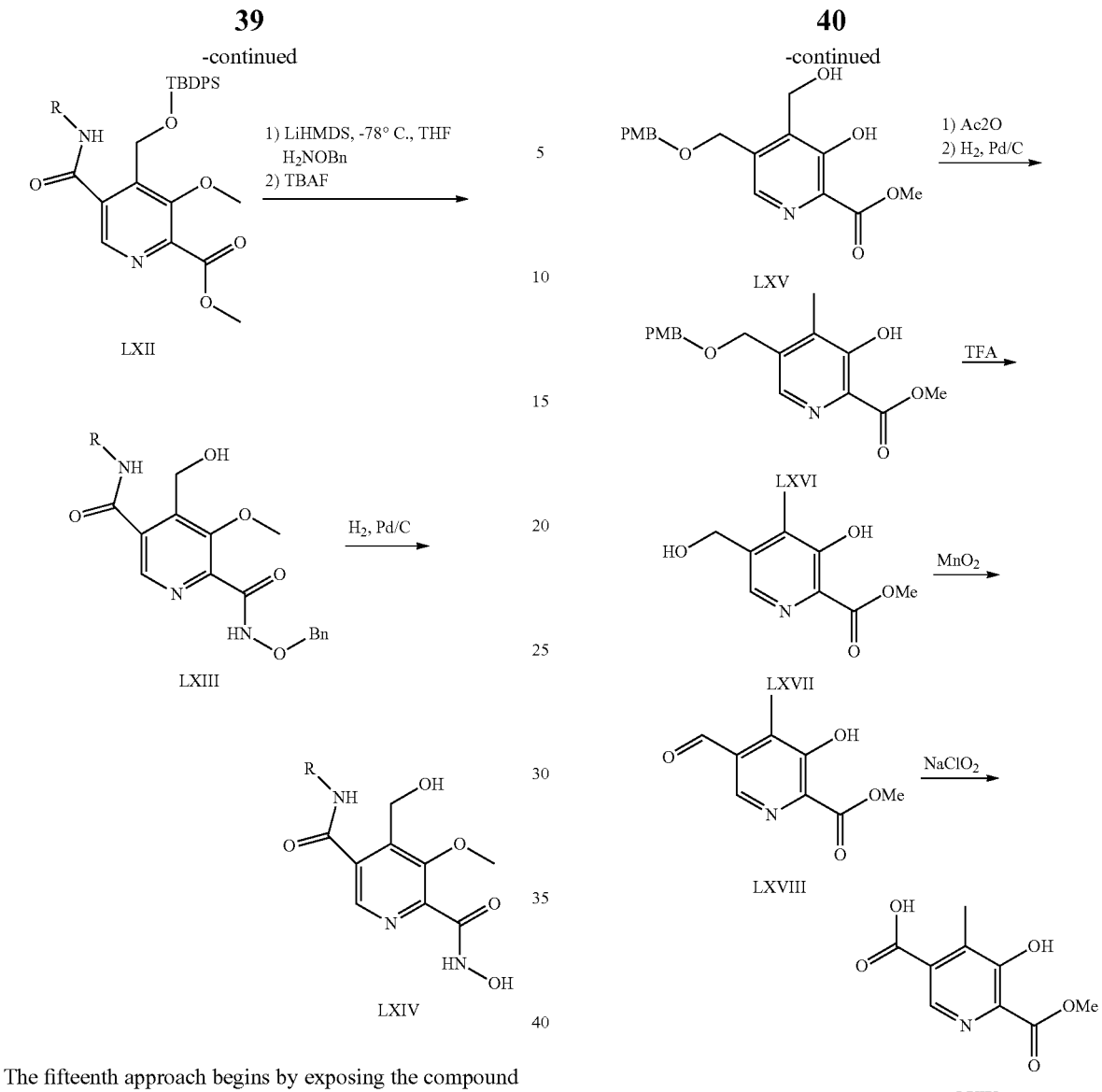

The fifteenth approach begins by exposing the compound XVIIe (of example 7) to aqueous formic acid to yield LXV. The liberated hydroxyl groups are then acylated with acetic anhydride to the acetyl esters and modified by catalytic hydrogenation to the methyl derivative LXVI in good yields. The PMB protecting group is remove by exposure to TFA and the liberated hydroxyl group oxidized in a stepwise manner to the aldehyde LXVII and carboxylic acid LXIX by reacting initially with manganese oxide then sodium chlorite respectively.

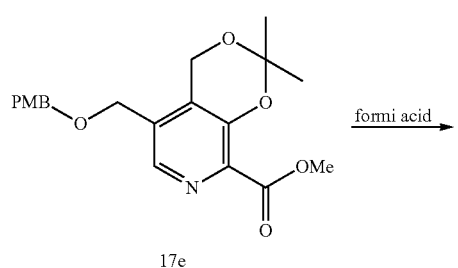

It can be appreciated by those skilled in the art the above synthetic schemes are not intended to be a comprehensive list of all means by which the compounds above may be synthesized. Further methods will be evident to those of ordinary skill in the art.

General Procedures

Preparative chromatography was performed by flash chromatography, using silica gel 60 (EM Science) with the indicated solvent systems and positive air pressure, to allow for a proper rate of elution, or with a Biotage SP4™ automated chromatography system. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid, followed by heating. Alternatively, analytical plates can be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Unless otherwise indicated: all starting materials were purchased from a commercial source such as Aldrich Co. or Sigma Co; melting points (mp) were determined on a Büchi 530 melting point apparatus in capillary tubes (uncorrected); mass spectra were recorded on a Hewlett Packard LC/MSD 1100 system APCI either in negative mode or positive mode; nuclear magnetic resonance (NMR) spectra were recorded on a Bruker AMX 400 equipped with a reversed or QNP probe.

Samples were dissolved in deutero-chloroform ($CDCl_3$), deuterium oxide ($D_2O$) or deutero-dimethylsulfoxide (DMSO-$d_6$) for data acquisition and tetramethylsilane was used as internal standard. Chemical shifts (δ) are expressed in parts per million (ppm), coupling constants (J) are expressed in hertz (Hz) and multiplicities are denoted as s for singlet, d for doublet, dd for doublet of doublets, t for triplet, q for quartet, quint for quintet, m for multiplet, and br s for broad singlet.

EXAMPLES

Example 1

Preparation of $N^2$,3-bis(benzyloxy)-$N^5$-(4-fluorobenzyl)-4-(hydroxymethyl)pyridine-2,5-dicarboxamide (Product 1)

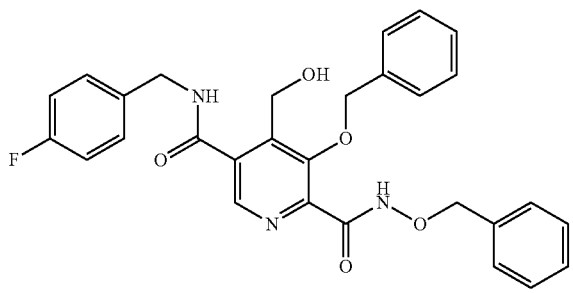 [SMILES: O=C(NCc1ccc(F)cc1)c1cnc(C(=O)NOCc2ccccc2)c(OCc2ccccc2)c1CO]

Step 1a: Preparation of N,9-bis(benzyloxy)-3,3-dimethyl-1,5-dihydro-[1,3]dioxepino[5,6-c]pyridine-8-carboxamide (Compound 1a)

Lithium bis(trimethylsilyl)amide (30.0 mL, 30.0 mmol, 3.75 eq) was added to benzylhydroxylamine hydrochloride (1.41 g, 8.82 mmol, 1.1 eq) in tetrahydrofuran (40.0 mL) at −78° C. The reaction mixture was stirred 10 min. and a solution of methyl 9-(benzyloxy)-3,3-dimethyl-1,5-dihydro-[1,3]dioxepino[5,6-c]pyridine-8-carboxylate, J. Med Chem, 1977, 20, p 745) (2.75 g, 8.01 mmol, 1 eq) in tetrahydrofuran (20.0 mL) was added. This reaction mixture was stirred at −78° C. for 30 min. and a solution of saturated ammonium chloride was added. The reaction mixture was then extracted with ethyl acetate and the organic phase recovered was concentrated under reduced pressure yielding 3.48 g of crude compound 1a (100% yield) as a white solid; MS-ESI m/z 435 [MH]$^+$.

Step 1b: Preparation of N,3-bis(benzyloxy)-4,5-bis(hydroxymethyl)picolinamide (Compound 1b)

Compound 1a was dissolved in water (50.0 mL), formic acid (5.0 mL) and tetrahydrofuran (25.0 mL) and stirred at 70° C. for 2 hours. Saturated aqueous sodium bicarbonate solution was added and the reaction mixture was extracted with ethyl acetate. The organic phase recovered was dried over magnesium sulfate and concentrated under reduced pressure yielding 3.44 g of crude compound 1b (100% yield) as a yellow oil; MS-ESI m/z 395 [MH]$^+$.

Step 1c: Preparation of N,7-bis(benzyloxy)-3-oxo-1,3-dihydrofuro[3,4-c]pyridine-6-carboxamide (Compound 1c)

Activated manganese dioxide (7 g, 80 mmol, 3 eq) and 3.4 g of compound 1b (80.0 mL) were stirred at room temperature in dichloromethane until the reaction was complete, as indicated by TLC. The reaction mixture was then filtered on Celite and concentrated under pressure. The crude product obtained was purified by chromatography on silica gel (30% ethyl acetate/hexane) yielding 0.4 g of compound 1c (13% yield) as a white solid and 1.8 g (58% yield) of the corresponding lactol, N,7-bis(benzyloxy)-3-hydroxy-1,3-dihydrofuro[3,4-c]pyridine-6-carboxamide (compound 1c-2); $^1$H-NMR (400 MHz, MeOD): δ=8.74 (s, 1H), 7.46 (m, 10H), 5.52 (s, 2H), 5.28 (s, 2H), 4.98 (s, 2H); MS-ESI m/z 391 [MH]$^+$.

Step 1d: Preparation of $N^2$,3-bis(benzyloxy)-$N^5$-(4-fluorobenzyl)-4-(hydroxymethyl)pyridine-2,5-dicarboxamide (Compound 1d)

4-Fluorobenzylamine (0.160 g, 1.29 mmol, 2 eq) and compound 1c (0.250 g, 0.641 mmol, 1 eq) were heated neat at 70° C. for 30 min. The crude product was purified by silica gel (100% ethyl acetate) yielding 0.275 g of $N^2$,3-bis(benzyloxy)-$N^5$-(4-fluorobenzyl)-4-(hydroxymethyl)pyridine-2,5-dicarboxamide as a white solid; MS-ESI m/z 516 [MH]$^+$.

Example 2

Preparation of $N^5$-(4-fluorobenzyl)-$N^2$,3-dihydroxy-4-(hydroxymethyl)pyridine-2,5-dicarboxamide (Product 2)

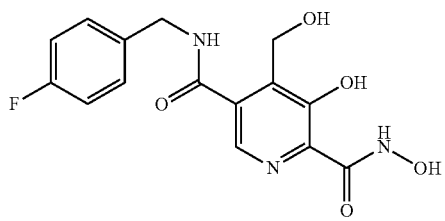 [SMILES: O=C(NCc1ccc(F)cc1)c1cnc(C(=O)NO)c(O)c1CO]

The product of example 1, $N^2$,3-bis(benzyloxy)-$N^5$-(4-fluorobenzyl)-4-(hydroxymethyl)pyridine-2,5-dicarboxamide, (0.170 g, 0.330 mmol, 1 eq) and 10% Pd/C catalyst (5 mg) were stirred in 4.0 mL of methanol under an atmosphere of hydrogen for 1 hour. The catalyst was filtered and the reaction mixture was concentrated under vacuum yielding 0.100 g of $N^5$-(4-fluorobenzyl)-$N^2$,3-dihydroxy-4-(hydroxymethyl)pyridine-2,5-dicarboxamide (90% yield) as a white solid;

¹H-NMR (400 MHz, MeOD): δ=8.17 (s, 1H), 7.44 (m, 2H), 7.09 (t, 2H), 4.78 (s, 2H), 4.58 (s, 2H); MS-ESI m/z 336 [MH]⁺.

Example 3

Preparation of N⁵-(benzo[d][1,3]dioxol-5-ylmethyl)-N2,3-bis(benzyloxy)-4-(hydroxymethyl)pyridine-2,5-dicarboxamide (Product 3)

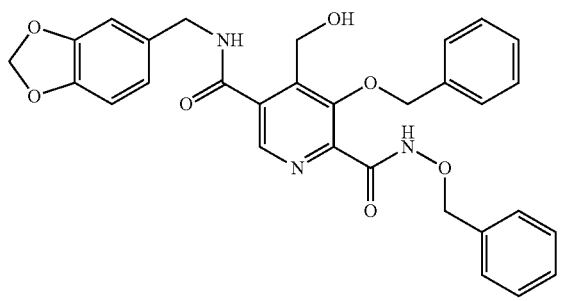 [SMILES: O=C(NCc1ccc2c(c1)OCO2)c1cnc(C(=O)NOCc2ccccc2)c(OCc2ccccc2)c1CO]

Piperonylamine (0.035 g, 0.288 mmol, 2 eq) and N,7-bis(benzyloxy)-3-oxo-1,3-dihydrofuro[3,4-c]pyridine-6-carboxamide (0.056 g, 0.144 mmol, 1 eq), compound 1c of example 1, were heated neat at 70° C. for 30 min. The crude product was purified by silica gel (30% ethyl acetate) yielding 0.048 g of N⁵-(benzo[d][1,3]dioxol-5-ylmethyl)-N2,3-bis(benzyloxy)-4-(hydroxymethyl)pyridine-2,5-dicarboxamide (62% yield) as a white solid; MS-ESI m/z 542 [MH]⁺.

Example 4

Preparation of N⁵-(benzo[d][1,3]dioxol-5-ylmethyl)-N2,3-dihydroxy-4-(hydroxymethyl)pyridine-2,5-dicarboxamide (Product 4)

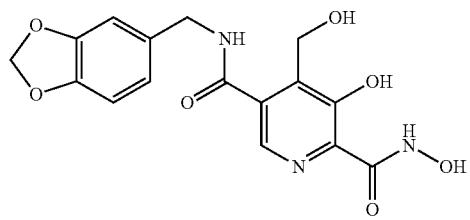 [SMILES: O=C(NCc1ccc2c(c1)OCO2)c1cnc(C(=O)NO)c(O)c1CO]

The final product of Example 3 above (0.170 g, 0.330 mmol, 1 eq) and 10% Pd/C (5 mg) catalyst were mixed in methanol (4.0 mL) under an atmosphere of hydrogen 1 hour. The catalyst was filtered and reaction mixture was concentrated under vacuum yielding 0.029 g of N⁵-(benzo[d][1,3]dioxol-5-ylmethyl)-N2,3-dihydroxy-4-(hydroxymethyl)pyridine-2,5-dicarboxamide (90% yield) as a white solid;

¹H-NMR (400 MHz, MeOD): δ=8.176 (s, 1H), 6.93 (m, 3H), 5.95 (s, 2H), 4.77 (s, 2H), 4.50 (s, 2H); MS-ESI m/z 362 [MH]⁺.

Example 5

Preparation of N²,3-bis(benzyloxy)-4-(hydroxymethyl)-N⁵-(4-methoxybenzyl)pyridine-2,5-dicarboxamide (Product 5)

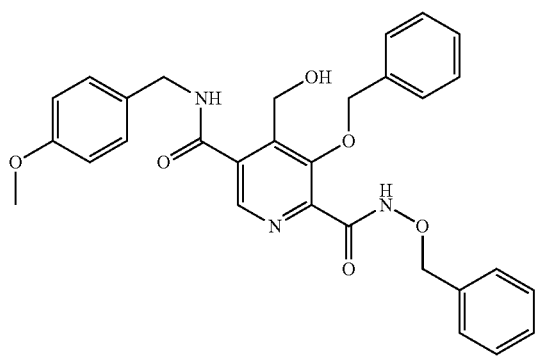 [SMILES: COc1ccc(CNC(=O)c2cnc(C(=O)NOCc3ccccc3)c(OCc3ccccc3)c2CO)cc1]

4-Methoxyaniline (0.018 g, 0.128 mmol, 2.5 eq) and N,7-bis(benzyloxy)-3-oxo-1,3-dihydrofuro[3,4-c]pyridine-6-carboxamide (0.020 g, 0.051 mmol, 1 eq) were heated neat at 70° C. for 30 min. The crude product was purified by silica gel (100% ethyl acetate) yielding 0.011 g of N²,3-bis(benzyloxy)-4-(hydroxymethyl)-N⁵-(4-methoxybenzyl)pyridine-2,5-dicarboxamide (41% yield) as a white solid; MS-ESI m/z 528 [MI-1]⁺.

Example 6

Preparation of N²,3-dihydroxy-4-(hydroxymethyl)-N⁵-(4-methoxybenzyl)pyridine-2,5-dicarboxamide (Product 6)

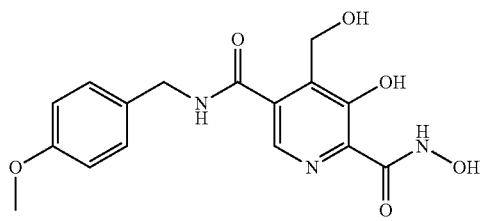 [SMILES: COc1ccc(CNC(=O)c2cnc(C(=O)NO)c(O)c2CO)cc1]

The product of example 5 (0.010 g, 0.019 mmol, 1 eq) and 10% Pd/C catalyst (5 mg) were stirred in 4.0 mL of methanol under an atmosphere of hydrogen for 1 hour. The catalyst was filtered and reaction mixture was concentrated under vacuum yielding 0.006 g of N²,3-dihydroxy-4-(hydroxymethyl)-N⁵-

(4-methoxybenzyl)pyridine-2,5-dicarboxamide (85% yield) as a white solid; MS-ESI m/z 348 [MH]$^+$.

Example 7

Preparation of N$^2$,3-bis(benzyloxy)-N$^5$-(3,5-difluorobenzyl)-4-(hydroxymethyl)pyridine-2,5-dicarboxamide (Product 7)

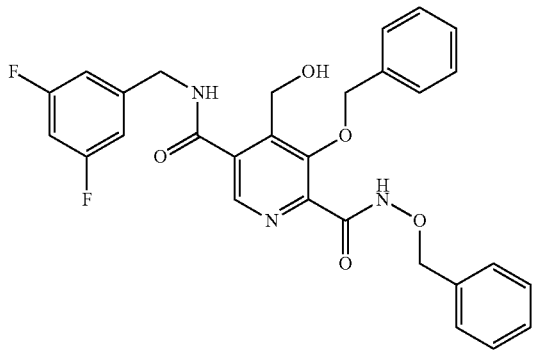 [SMILES: O=C(NCc1cc(F)cc(F)c1)c1cnc(C(=O)NOCc2ccccc2)c(OCc2ccccc2)c1CO]

3,5-difluorobenzylamine (0.02 g, 0.154 mmol, 2.5 eq) and N,7-bis(benzyloxy)-3-oxo-1,3-dihydrofuro[3,4-c]pyridine-6-carboxamide (0.030 g, 0.077 mmol, 1 eq) were heated neat at 70° C. for 30 min. The crude product was purified by silica gel (100% ethyl acetate) yielding 0.011 g of N$^2$,3-bis(benzyloxy)-N$^5$-(3,5-difluorobenzyl)-4-(hydroxymethyl)pyridine-2,5-dicarboxamide (15% yield) as a white solid; MS-ESI m/z 534 [MH]$^+$.

Example 8

Preparation of N$^5$-(3,5-difluorobenzyl)-N$^2$,3-dihydroxy-4-(hydroxymethyl)pyridine-2,5-dicarboxamide (Product 8)

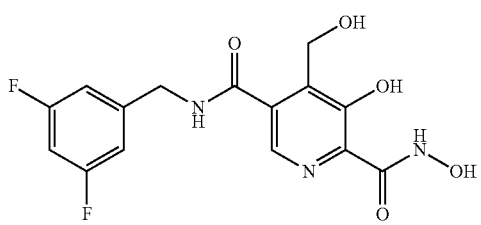 [SMILES: O=C(NCc1cc(F)cc(F)c1)c1cnc(C(=O)NO)c(O)c1CO]

The product of example 7 (0.006 g, 0.011 mmol, 1 eq) and 10% Pd/C catalyst (5 mg) were mixed in 4.0 mL of methanol under an atmosphere of hydrogen 1 hour.

The catalyst was filtered and the reaction mixture was concentrated under vacuum yielding 0.004 g of N$^5$-(3,5-difluorobenzyl)-N$^2$,3-dihydroxy-4-(hydroxymethyl)pyridine-2,5-dicarboxamide (67% yield) as a white solid; MS-ESI m/z 354 [MH]$^+$.

Example 9

Preparation of 5-((4-fluorobenzylamino)methyl)-N,3-dihydroxy-4-(methoxymethyl)picolinamide) (Product 9)

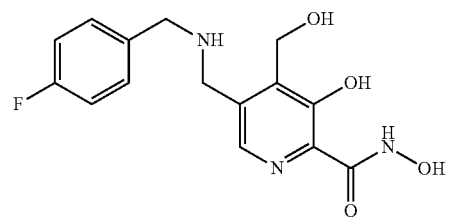 [SMILES: O=C(NO)c1ncc(CNCc2ccc(F)cc2)c(CO)c1O]

Step 9a: Preparation of N,3-bis(benzyloxy)-5-((4-fluorobenzylamino)methyl)-4-(hydroxymethyl)picolinamide (Compound 9a)

4-fluorobenzylamine (0.035 g, 0.281 mmol, 1.1 eq), followed by sodium cyanoborohydride (0.048 g, 0.765 mmol, 3 eq) were added to N,7-bis(benzyloxy)-3-hydroxy-1,3-dihydrofuro[3,4-c]pyridine-6-carboxamide (0.100 g, 0.255 mmol, 1 eq), compound 1c-2 of example 1, in 10.0 mL of ethanol. This reaction mixture was stirred at room temperature overnight. Saturated aqueous sodium bicarbonate solution was added and the reaction mixture was extracted with ethyl acetate. Organic phase recovered was dried over magnesium sulfate and concentrated under reduced pressure. The crude product was purified by silica gel (100% ethyl acetate) yielding 0.050 g of compound 9a (39% yield) as a white solid; MS-ESI m/z 502 [MH]$^+$.

Step 9b: Preparation of 5-((4-fluorobenzylamino)methyl)-N,3-dihydroxy-4-(methoxymethyl)picolinamide Compound 9a (0.013 g, 0.019 mmol, 1 eq) and 10% Pd/C catalyst (5 mg) were stirred in 4 mL of methanol under an atmosphere of hydrogen for 12 hrs. The catalyst was filtered and reaction mixture was concentrated under vacuum yielding 0.006 g of 5-((4-fluorobenzylamino)methyl)-N,3-dihydroxy-4-(methoxymethyl)picolinamide) (75% yield) as a white solid; MS-ESI m/z 322 [MH]$^+$.

Example 10

Preparation of 5-((3,5-difluorobenzylamino)methyl)-N,3-dihydroxy-4-(hydroxymethyl)picolinamide

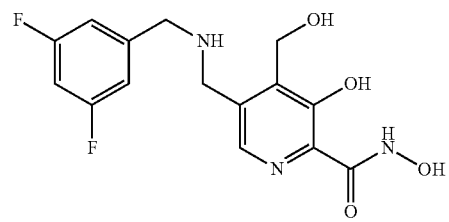 [SMILES: O=C(NO)c1ncc(CNCc2cc(F)cc(F)c2)c(CO)c1O]

Step 10a: Preparation of 5-((3,5-difluorobenzy-lamino)methyl)-N,3-dihydroxy-4-(hydroxymethyl) picolinamide (Compound 10a)

N,7-bis(benzyloxy)-3-hydroxy-1,3-dihydrofuro[3,4-c]pyridine-6-carboxamide (compound 1c-2 of example 1) (0.200 g, 0.510 mmol, 1 eq) in 10.0 mL of ethanol was added to 3,5-difluorobenzylamine (0.080 g, 0.561 mmol, 1.1 eq), followed by sodium cyanoborohydride (0.096 g, 1.53 mmol, 3 eq). The reaction mixture was stirred at room temperature overnight. 1M potassium carbonate solution was added and the reaction mixture was extracted with ethyl acetate. Organic phase recovered was dried over magnesium sulfate and concentrated under reduced pressure. The crude product was purified by silica gel (100% ethyl acetate) yielding 0.046 g of compound 10a (17% yield) as a white solid; MS-ESI m/z 520 [MH]+.

Step 10b: Preparation of 5-((3,5-difluorobenzy-lamino)methyl)-N,3-dihydroxy-4-(hydroxymethyl) picolinamide Compound 10a (0.020 g, 0.039 mmol, 1 eq) and 10% Pd/C (5 mg) in 4.0 mL of methanol were stirred under an atmosphere of hydrogen overnight. The catalyst was filtered and reaction mixture was concentrated under vacuum to give 0.010 g of 5-((3,5-difluorobenzylamino)methyl)-N,3-dihydroxy-4-(hydroxymethyl)picolinamide (76% yield) as a white solid; MS-ESI m/z 340 [MH]+.

Example 11

Preparation of 5-((benzo[d][1,3]dioxol-5-ylmethy-lamino)methyl)-N,3-dihydroxy-4-(hydroxymethyl) picolinamide (Product 11)

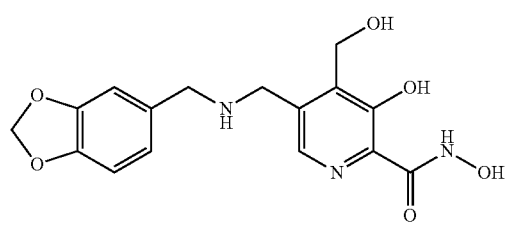 [SMILES: O=C(NO)c1ncc(CNCc2ccc3c(c2)OCO3)c(CO)c1O]

Step 11a: Preparation of 5-((benzo[d][1,3]dioxol-5-ylmethylamino)methyl)-N,3-bis(benzyloxy)-4-(hy-droxymethyl)picolinamide (Compound 11a)

N,7-bis(benzyloxy)-3-hydroxy-1,3-dihydrofuro[3,4-c]pyridine-6-carboxamide (compound 1c-2 of example 1) (0.150 g, 0.383 mmol, 1 eq) was added to 10.0 mL of ethanol followed by 0.072 g of sodium cyanoborohydride (1.15 mmol, 3 eq). The reaction mixture was stirred at room temperature overnight. A 1M potassium carbonate solution was added to the reaction mixture followed by extraction with ethyl acetate. Organic phase recovered was dried over magnesium sulfate and concentrated under reduced pressure. The crude product was purified by silica gel chromatography (100% ethyl acetate) yielding 0.046 g of compound 11a (22% yield) as a white solid; MS-ESI m/z 528 [MH]+.

Step 11b: Preparation of 5-((benzo[d][1,3]dioxol-5-ylmethylamino)methyl)-N,3-dihydroxy-4-(hy-droxymethyl)picolinamide Compound 11a (0.024 g, 0.039 mmol, 1 eq) and 10% Pd/C catalyst (5 mg) were stirred in 4.0 mL of methanol overnight under an atmosphere of hydrogen. The catalyst was filtered and the reaction mixture was concentrated under vacuum yielding 0.011 g of 5-((benzo[d][1,3]-dioxol-5-ylmethy-lamino)methyl)-N,3-dihydroxy-4-(hydroxymethyl)picolinamide (69% yield) as a white solid; MS-ESI m/z 348 [MH]+.

Example 12

Preparation of $N^5$-(4-fluorobenzyl)-N2,3-dihydroxy-4-(methoxymethyl)-$N^5$-methylpyridine-2,5-dicarboxamide (Product 12)

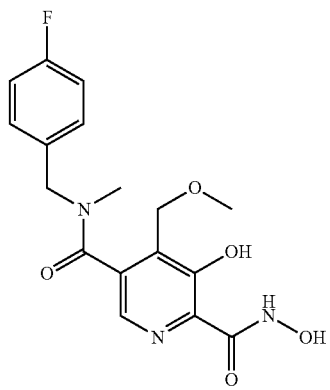 [SMILES: COCc1c(C(=O)N(C)Cc2ccc(F)cc2)cnc(C(=O)NO)c1O]

Step 12a: Preparation of 5-(benzyloxy)-N-(4-fluorobenzyl)-4-(hydroxymethyl)-6-methylnicotinamide (Compound 12a)

Benzyloxy)-6-methylfuro[3,4-c]pyridin-3(1H)-one (Paul, B., Korytnyk, W. J. Het. Chem., 1976, v13, p 701) (1.00 g, 3.92 mmol, 1 eq) and 4-fluorobenzylamine (0.491 g, 3.92 mmol, 1.1 eq) were heated neat at 70° C. for 1 hour. The crude product was purified by silica gel (100% ethyl acetate) yielding 1.42 g of compound 12a (95% yield) as a white solid; MS-ESI m/z 381 [MH]+.

Step 12b: Preparation of 5-(benzyloxy)-N-(4-fluorobenzyl)-4-(methoxymethyl)-N, 6-dimethylnicoti-namide (Compound 12b)

Sodium hydride in tetrahydrofuran (10.0 mL) was added to compound 12a (0.690 g, 1.82 mmol, 1 eq) at room temperature. The reaction mixture was stirred at room temperature 20 min. and 0.541 g of iodomethane (3.81 mmol, 2.1 eq) was added. Water was added and reaction mixture was extracted with ethyl acetate. Organic phase recovered was dried over magnesium sulfate and concentrated. The crude product was purified by silica gel (60% ethyl acetate/hexane) yielding 0.400 g of compound 12b (22% yield) as a white solid; MS-ESI m/z 409 [MH]+.

Step 12c: Preparation of 3-(benzyloxy)-5-((4-fluorobenzyl)(methyl)carbamoyl)-4-(methoxymethyl)-2-methylpyridine 1-oxide (Compound 12b)

Compound 12b (0.400 g, 0.980 mmol, 1 eq) in dichloromethane (20.0 mL) was added to 3-chloroperbenzoic acid (0.254 g, 1.47 mmol, 1.5 eq) at room temperature and the reaction mixture was stirred for 1 hour at room temperature. A 1M solution of potassium carbonate was added and the reaction mixture was extracted with dichloromethane. Organic phase recovered was dried over magnesium sulfate and concentrated yielding 0.400 g of compound 12c (95% yield) as a white solid; MS-ESI m/z 424 [MH]$^+$.

Step 12d: Preparation of 5-(benzyloxy)-N-(4-fluorobenzyl)-6-(hydroxymethyl)-4-(methoxymethyl)-N-methylnicotinamide (Compound 12d)

Compound 12c (0.400 g, 0.946 mmol, 1 eq) in dichloromethane (20.0 mL) was added to trifluoroacetic anhydride (1.30 g, 4.90 mmol, 5 eq) at room temperature. The reaction mixture was stirred overnight at room temperature. A 1M solution of potassium carbonate was added and the reaction mixture was extracted with ethyl acetate. Organic phase recovered was dried over magnesium sulfate and concentrated yielding 0.400 g of compound 12d (97% yield) as a white solid; MS-ESI m/z 424 [MH]$^+$.

Step 12e: Preparation of 5-(benzyloxy)-N-(4-fluorobenzyl)-6-formyl-4-(methoxymethyl)-N-methylnicotinamide (Compound 12d)

Compound 12d (0.400 g, 0.946 mmol, 1 eq) in dichloromethane (20.0 mL) was added to activated manganese oxide (0.852 g, 9.80 mmol, 10 eq) at room temperature. The reaction mixture was stirred overnight at room temperature. The reaction mixture was filtered on Celite and concentrated under reduced pressure. A 1M solution of potassium carbonate was added and the reaction mixture was extracted with ethyl acetate. The crude product was purified by silica gel (40% ethyl acetate/hexane) yielding 0.122 g of compound 12e (30% yield) as a white solid; MS-ESI m/z 423 [MH]$^+$.

Step 12f: Preparation methyl 3-(benzyloxy)-5-((4-fluorobenzyl)(methyl)carbamoyl)-4-(methoxymethyl)picolinate (Compound 12f)

Compound 12e (0.122 g, 0.289 mmol, 1 eq) in methanol (20.0 mL) was added to powdered potassium hydroxide (0.042 g, 0.751 mmol, 2.6 eq) at room temperature. The reaction mixture was stirred at room temperature 10 min. and iodine (0.095 g, 0.376 mmol, 1.3 eq) was added. The reaction mixture was then stirred for 4 hours at room temperature following which a solution of sodium bisulfite was added. The reaction mixture was extracted with ethyl acetate and organic phase recovered was dried over magnesium sulfate and concentrated to give 0.114 g of compound 12f (95%) as a colourless oil; MS-ESI m/z 453 [MH]$^+$.

Step 12g: Preparation of N$^2$,3-bis(benzyloxy)-N$^5$-(4-fluorobenzyl)-4-(methoxymethyl)-N$^5$-methylpyridine-2,5-dicarboxamide (Compound 12g)

Benzylhydroxylamine hydrochloride (0.045 g, 0.282 mmol, 1.1 eq) in tetrahydrofuran (3.0 mL) was added lithium bis(trimethylsilyl)amide (1.30 mL, 1.27 mmol, 5 eq) at −78° C. The reaction mixture was stirred for 10 min. following which a solution of compound 12f (0.115 g, 0.254 mmol, 1 eq) in tetrahydrofuran (2.0 mL) was added. The reaction mixture was then stirred at −78° C. for 30 min. and a solution of saturated ammonium chloride was added. The reaction mixture was extracted with ethyl acetate and organic phase recovered was concentrated under reduced pressure.

The crude product was purified by silica gel (100% ethyl acetate) yielding 0.100 g of compound 12g (72% yield) of a clear oil; MS-ESI m/z 544 [MH]$^+$.

Step 12h: Preparation of N$^5$-(4-fluorobenzyl)-N2,3-dihydroxy-4-(methoxymethyl)-N$^5$-methylpyridine-2, 5-dicarboxamide Compound 12g (0.100 g, 0.184 mmol, 1 eq) and 10% Pd/C (5 mg) catalyst were stirred in methanol (4.0 mL) under a hydrogen atmosphere for 1 hour. The catalyst was filtered and the reaction mixture was concentrated under vacuum yielding 0.040 g of N$^5$-(4-fluorobenzyl)-N2,3-dihydroxy-4-(methoxymethyl)-N$^5$-methylpyridine-2,5-dicarboxamide (60% yield) as a white solid; MS-ESI m/z 364 [MH]$^+$.

Example 13

Preparation of N$^2$,3-bis(benzyloxy)-N$^5$-(3-chloro-4-fluorobenzyl)-4-(hydroxymethyl)pyridine-2,5-dicarboxamide (Product 13)

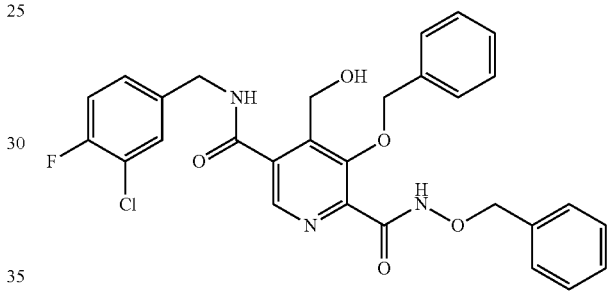

4-Fluoro-3-Chloro benzylamine (0.060 g, 1.29 mmol, 2 eq) and N,7-bis(benzyloxy)-3-oxo-1,3-dihydrofuro[3,4-c]pyridine-6-carboxamide (0.050 g, 0.141 mmol, 1 eq) (compound 1c of example 1) were heated in DMF at 90° C. for 120 min. The crude product was purified by silica gel (100% ethyl acetate) yielding 0.03 g of N$^2$,3-bis(benzyloxy)-N$^5$-(3-chloro-4-fluorobenzyl)-4-(hydroxymethyl)pyridine-2,5-dicarboxamide as a white solid; MS-ESI m/z 573 [MH]$^-$.

Example 14

Preparation of N$^5$-(3-chloro-4-fluorobenzyl)-N2,3-dihydroxy-4-(hydroxymethyl)pyridine-2,5-dicarboxamide (Product 14)

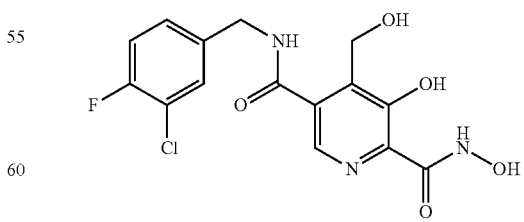

The product of example 13 (0.03 g, 0.330 mmol,) and 10% Pd/C catalyst (25 mg) were stirred in methanol (4.0 mL) under an atmosphere of hydrogen for 1 hour. The catalyst was filtered and the reaction mixture was concentrated under vacuum yielding 0.015 g of $N^5$-(3-chloro-4-fluorobenzyl)-$N^2$,3-dihydroxy-4-(hydroxymethyl)pyridine-2,5-dicarboxamide as a white solid; $^1$H-NMR (400 MHz, dmso): δ=13.01 (s, 1H), 12.0 (s, 1H), 9.51 (s 1H), 9.02 (t 1H), 8.11 (s, 1H), 7.60 (d 1H), 7.40 (m, 2H), 4.68 (s, 2H), 4.48 (s, 2H); MS-ESI m/z 370 [MH]$^+$.

Example 15

Preparation of $N^2$,3-bis(benzyloxy)-$N^5$-(3,4-dichlorobenzyl)-4-(hydroxymethyl)pyridine-2,5-dicarboxamide (Product 15)

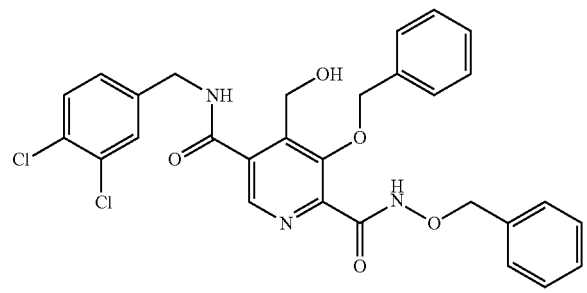 [SMILES: O=C(NCc1ccc(Cl)c(Cl)c1)c1cnc(C(=O)NOCc2ccccc2)c(OCc2ccccc2)c1CO]

3,4 diChloro benzylamine (0.060 g, 1.29 mmol, 2 eq) and N,7-bis(benzyloxy)-3-oxo-1,3-dihydrofuro[3,4-c]pyridine-6-carboxamide (0.050 g, 0.141 mmol, 1 eq) (compound 1c of example 1) were heated in DMF at 90° C. for 120 min. The crude product was purified by silica gel (100% ethyl acetate) yielding 0.03 g of $N^2$,3-bis(benzyloxy)-$N^5$-(3,4-dichlorobenzyl)-4-(hydroxymethyl)pyridine-2,5-dicarboxamide (29%) as a white solid; MS-ESI m/z 589 [MH]$^+$.

Example 16

Preparation of $N^5$-(3,4-dichlorobenzyl)-$N^2$-(3-dihydroxy-4-(hydroxymethyl)pyridine-2,5-dicarboxamide (Product 16)

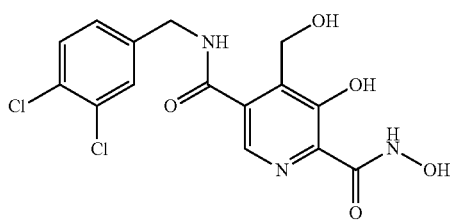 [SMILES: O=C(NCc1ccc(Cl)c(Cl)c1)c1cnc(C(=O)NO)c(O)c1CO]

Product 15 of example 15 (0.03 g, 0.330 mmol,) and 10% Pd/C (25 mg) catalyst were stirred in methanol (4.0 mL) under an atmosphere of hydrogen for 1 hour. The catalyst was filtered and the reaction mixture was concentrated under vacuum to give 0.006 g of $N^5$-(3,4-dichlorobenzyl)-$N^2$,3-dihydroxy-4-(hydroxymethyl)pyridine-2,5-dicarboxamide as a white solid; $^1$H-NMR (400 MHz, dmso): δ=13.01 (s, 1H), 12.0 (s, 1H), 9.51 (s 1H), 9.02 (t 1H), 8.11 (s, 1H), 7.60 (d 1H), 7.40 (m, 2H), 4.68 (s, 2H), 4.48 (s, 2H); MS-ESI m/z 386 [MH]$^+$.

Example 17

Preparation of N,3-Dihydroxy-4-(hydroxymethyl)-5-((4-methoxybenzyloxy)methyl)-picolinamide (Product 17)

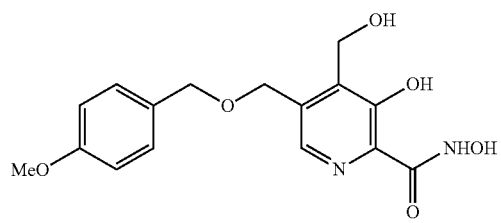

Step 17a: Preparation of 5-((4-Methoxybenzyloxy)methyl)-2,2,8-trimethyl-4H-[1,3]dioxino[4,5-c]pyridine (Compound 17a)

Anhydrous THF (200 ml) was added to NaH (60%, 24 g, 600 mmol) at 0° C. under a nitrogen atmosphere. To this suspended mixture a solution of 2,2,8-trimethyl-4H-[1,3]dioxino[4,5-c]pyridin-5-yl)methanol (32.0 g, 150 mmol) in 400 ml of THF (J. Med. Chem., 1977, 20, p 745) was added. The resulting mixture was refluxed for 30 min; a significant amount of precipitate accumulated during the reflux. After cooling to room temperature, p-methoxybenzyl chloride (23.5 g, 150 mmol) was introduced drop-wise and the resulting mixture was refluxed for another 8 h. The reaction was quenched carefully by adding ice-cold water to the viscous mixture at 0° C. and diluted with a saturated ammonium chloride solution followed by extraction with methylene chloride. The combined organic extracts were washed with brine, dried (Na$_2$SO$_4$), and concentrated yielding a brown oil. The crude product was purified by chromatography (10% ethyl acetate/petroleum ether) yielding 25.0 g of compound 17a (50% yield); LC-MS (M+H)$^+$ m/z 331.

Step 17b: Preparation of 5-((4-Methoxybenzyloxy)methyl)-2,2,8-trimethyl-4H-[1,3]dioxino[4,5-c]pyridine 7-oxide (Compound 17b)

Compound 17a was dissolved in dry CH$_2$Cl$_2$ (500 mL) and the solution was cooled to 0° C. and m-chloroperbenzoic acid (85% purity of the reagent, 37.0 g, 182 mmol, 1.2 equiv) was added. After stirring at 23° C. for 12 h, the reaction mixture was extracted with Na$_2$SO$_3$ (10%, 2×200 mL), NaHCO$_3$ (5%, 2×200 mL), H$_2$O, dried (Na$_2$SO$_4$), filtered and the solvent was removed under reduced pressure. The crude product was purified by chromatography (10% methanol/ethyl acetate) yielding 35 g of compound 17b (68% yield) as pale-yellow solid; LC-MS (M+H)$^+$ m/z 346).

Step 17c: Preparation of (5-((4-Methoxybenzyloxy)methyl)-2,2-dimethyl-4H-[1,3]dioxino[4,5-c]pyridin-8-yl)methanol (Compound 17c)

Trifluoroacetic anhydride (4.5 mL, 32 mmol) was added to a solution of compound 17b (21.2 g, 61 mmol) in dry CH$_2$Cl$_2$ (200 ml) at 0° C. and stirred for 5 min. An additional amount of trifluoroacetic anhydride (11.5 mL, 82.7 mmol) was added and the reaction mixture was stirred overnight at 23° C. The reaction mixture was cooled to 0° C. and MeOH (150 mL) was added while stirring was continued. The solvents were evaporated and the resulting residue was dissolved in CH$_2$Cl$_2$ and washed with Na$_2$CO$_3$ (20% aqueous) and H$_2$O until the pH was neutral. Organic phase recovered was dried (Na$_2$SO$_4$), filtered and concentrated under vacuum. The residue was crystallized from EtOH—CH$_2$Cl$_2$ yielding 17.5 g of compound 17c (83% yield); LC-MS (M+H)$^+$ m/z 346.

Step 17d: Preparation of 5-((4-Methoxybenzyloxy) methyl)-2,2-dimethyl-4H-[1,3]dioxino[4,5-c]pyridine-8-carbaldehyde (Compound 17d)

IBX (35.5 g, 128 mmol) was added to a solution of (5-((4-methoxybenzyloxy)methyl)-2,2-dimethyl-4H-[1,3]dioxino[4,5-c]pyridin-8-yl)methanol (compound 17c) (14.60 g, 42.3 mmol) in ethyl acetate (500 mL) and the suspension was heated to reflux for 4 h. The precipitate was removed by filtration and the filtrate was concentrated under reduced pressure yielding 14.0 g of compound 17d (95% yield). Crude compound 17d was used for the next step without further purification; LC-MS (M+H)$^+$ m/z 344.

Step 17e: Preparation of ethyl 5-((4-methoxybenzyloxy)methyl)-2,2-dimethyl-4H-[1,3]dioxino[4,5-c]pyridine-8-carboxylate (Compound 17e)

KOH (85%, 5.3 g, 78 mmol) and iodine (9.9 g, 39 mmol) were added to a solution compound 17d (10.3 g, 30 mmol) in anhydrous MeOH (120 mL), at 0° C. The reaction mixture was kept at 23° C. and stirred for 12 h until no starting material was detected by TLC. The solution was then treated with Na$_2$SO$_3$ (solid) and the pH was adjusted to 7. The solid was filtered and solvent was removed under reduced pressure. The residue was dissolved in EtOAc and washed with water. The combined organic extracts were dried (Na$_2$SO$_4$), filtered and concentrated in vacuum. The crude residue was purified by chromatography (SiO$_2$) with petroleum ether:ethyl acetate (5:1) as eluent yielding 8.8 g of compound 17e (78% yield) as pale-yellow solid; LC-MS (M+H)$^+$ m/z 374.

Step 17f: Preparation of Ethyl 3-hydroxy-4-(hydroxymethyl)-5-(4-methoxybenzyloxy)methyl)picolinate (Compound 17f)

A solution of compound 17e (8.8 g, 23.6 mmol) in 200 mL of HCl/MeOH was stirred at 23° C. for 24 h. MeOH (500 mL) was added to dissolve the suspension and NaHCO$_3$ (solid) was added to neutralize the reaction mixture. Excess solid was filtered and the solvent was removed under reduced pressure. The residue was dissolved in EtOAc and washed with water. The combined organic extracts were dried (Na$_2$SO$_4$), filtered and concentrated in vacuum yielding 6.0 g of compound 17f (100% yield) as a light yellow solid; LC-MS (M+H)$^+$ m/z 334.

Step 17g: Preparation of N,3-Dihydroxy-4-(hydroxymethyl)-5-((4-methoxybenzyloxy)methyl)picolinamide Hydroxylamine hydrochloride (0.042 g, 0.60 mmol) and N,N-diisopropylethylamine (0.13 mL, 0.75 mmol) were added to a solution of compound 17f (0.050 g, 0.15 mmol) in MeOH (3 mL). The resulting mixture was placed in the microwave and heated to 80° C. for 1.5 h. The crude mixture was diluted with EtOAc and washed with saturated aqueous ammonium chloride solution and brine. The organic extract was dried (Na$_2$SO$_4$), filtered and concentrated in vacuum to yielding 0.039 g of N,3-Dihydroxy-4-(hydroxymethyl)-5-((4-methoxybenzyloxy)methyl)-picolinamide (78% yield); LC-MS (M+H)$^+$ m/z 335.

Example 18

Preparation of 5-(Benzyloxymethyl)-N,3-dihydroxy-4-(hydroxymethyl)picolinamide (Product 18)

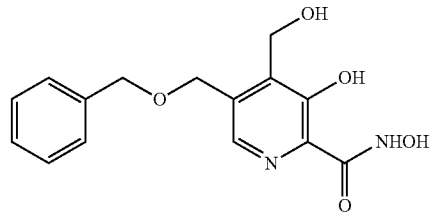

The procedure described in Example 17 was applied using benzyl bromide in step 17a yielding 0.054 g of 5-(Benzyloxymethyl)-N,3-dihydroxy-4-(hydroxymethyl)picolinamide as a white solid (45% yield); LC-MS (M+H)$^+$ m/z 305.

Example 19

Preparation of N-hydroxy-5-((4-methoxybenzyloxy)methyl)-2,2-dimethyl-4H-[1,3]dioxino[4,5-c]pyridine-8-carboxamide (Product 19)

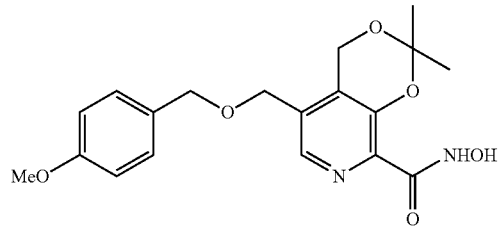

Step 19a: Preparation of 5-((4-Methoxybenzyloxy)methyl)-2,2-dimethyl-4H-[1,3]dioxino[4,5-c]pyridine-8-carboxylic Acid (Compound 19a)

Lithium hydroxide monohydrate (0.049 g, 1.18 mmol) was added to a solution of compound 17e (0.367 g, 0.98 mmol) in THF/H$_2$O (5/10 mL). The resulting mixture was stirred at 23° C. for 18 h. The solution was then acidified with AcOH, extracted with EtOAc and washed with brine. The organic extract was dried (Na$_2$SO$_4$), filtered and concentrated in vacuum yielding 0.315 g of compound 19a (90% yield); LC-MS (M+H)$^+$ m/z 360.

Step 19b: Preparation of N-(Benzyloxy)-5-((4-methoxybenzyloxy)methyl)-2,2-dimethyl-4H-[1,3]dioxino[4,5-c]pyridine-8-carboxamide (Compound 19a)

A solution of compound 19a (0.307 g, 0.86 mmol) and O-(benzotriazol-1-yl)-N,N,N',N'-tetramethyluronium hexafluorophosphate (HBTU) (0.389 g, 1.03 mmol) in acetonitrile (20 mL) was stirred at 23° C. for 15 minutes. Benzylhydroxylamine hydrochloride (0.137 g, 0.86 mmol) and N,N- diisopropylethylamine (0.45 mL, 2.58 mmol) were added to the solution and the reaction mixture was stirred at 23° C. for 17 h. The solvent was then removed in vacuum, and saturated aqueous ammonium chloride solution was added, followed by extraction with EtOAc. The combined organic extracts were washed with brine, dried (MgSO$_4$), filtered and concentrated in vacuum. The crude residue was purified by flash chromatography (SiO$_2$) with hexane:ethyl acetate as eluent yielding 0.380 g of compound 19b (95% yield); LC-MS (M+H)$^+$ m/z 465.

Step 19c: Preparation of N-(Benzyloxy)-3-hydroxy-4-(hydroxymethyl)-5-((4-methoxybenzyloxy)methyl)picolinamide (Compound 19c)

A solution of compound 19b (0.060 g, 0.13 mmol) in hydrogen chloride-ethanol solution (5 mL) was stirred at 23° C. for 5 h. The solvent was then removed in vacuum and an aqueous solution of NaHCO$_3$ (1M) was added. The reaction mixture was extracted with CH$_2$Cl$_2$ and the combined organic extracts were washed with brine, dried (MgSO$_4$), filtered and concentrated in vacuum yielding 0.030 g of compound 19c (54% yield); LC-MS (M+H)$^+$ m/z 425.

Step 19d N-hydroxy-5-((4-methoxybenzyloxy)methyl)-2,2-dimethyl-4H-[1,3]dioxino[4,5-c]pyridine-8-carboxamide A solution of compound 19c (0.10 g, 0.22 mmol) in ethyl acetate (10 mL) was hydrogenated under 1 atm of hydrogen at 23° C. over 10% palladium on activated carbon for 1 h. The reaction mixture was filtered and the solution was concentrated in vacuum. The residue was purified on preparative TLC with CH$_2$Cl$_2$:MeOH (9:1) as eluent yielding 0.016 g of N-hydroxy-5-((4-methoxybenzyloxy)methyl)-2,2-dimethyl-4H-[1,3]dioxino[4,5-c]pyridine-8-carboxamide (20% yield). LC-MS (M+H)$^+$ m/z 375.

Example 20

Preparation of N$^5$-(3,4-difluorobenzyl)-N$^2$,3-dihydroxy-4-(hydroxymethyl)pyridine-2,5-dicarboxamide (Product 20)

N$^5$-(3,4-difluorobenzyl)-N$^2$,3-dihydroxy-4-(hydroxymethyl)pyridine-2,5-dicarboxamide was prepared using the procedure described in Example 2 and using 3,4 difluorobenzylamine as the starting material.

Example 21

Preparation of 5-[(4-Fluoro-phenylamino)-methyl]-3-hydroxy-4-hydroxymethyl-pyridine-2-carboxylic Acid Hydroxyamide (Product 21)

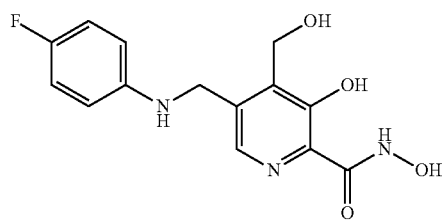 [SMILES: O=C(NO)c1ncc(CNc2ccc(F)cc2)c(CO)c1O]

Step 21a: Preparation of methyl 5-((4-fluorophenylamino)methyl)-2,2-dimethyl-4H-[1,3]dioxino[4,5-c]pyridine-8-carboxylate (Compound 21a)

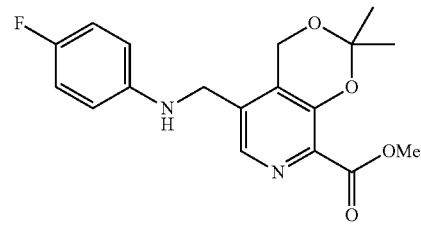 [SMILES: COC(=O)c1ncc(CNc2ccc(F)cc2)c2c1OC(C)(C)OC2]

Acetic acid (50 µL, 0.87 mmol) was added to a mixture of 5-Formyl-2,2-dimethyl-4H-[1,3]dioxino[4,5-c]pyridine-8-carboxylic acid methyl ester [J. Org. Chem. 1999, 64, 4537] (220 mg, 0.87 mmol) and 4-fluoroaniline (125 µL, 1.3 mmol) in dry methanol (4 mL) and stirred at room temperature for 15 min. and sodium cyanoborohydride (72 mg, 1.3 mmol) was added. This mixture was stirred at room temperature for 3 h followed by evaporation of 90% of the methanol volume under reduced pressure. The residue was extracted with dichloromethane (3×25 mL) and the combined organic layers were dried (anh. Na$_2$SO$_4$), filtered and concentrated under reduced pressure. The crude product was purified by silica gel (methanol/dichloromethane, 0 to 10% methanol) to give 0.290 g of methyl 5-((4-fluorophenylamino)methyl)-2,2-dimethyl-4H-[1,3]dioxino[4,5-c]pyridine-8-carboxylate (compound 21a) (96%) as a white solid MS-ESI m/z 347 [MI-1]$^+$.

Step 21b: Preparation of 5-((4-fluorophenylamino)methyl)-3-hydroxy-4-(hydroxymethyl)picolinate (Compound 21b)

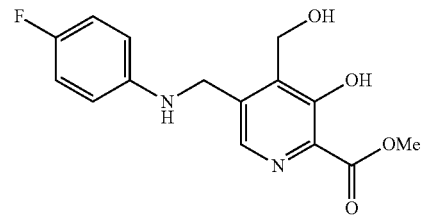 [SMILES: COC(=O)c1ncc(CNc2ccc(F)cc2)c(CO)c1O]

Formic acid (2 mL) was added to methyl 544-fluorophenylamino)methyl)-2,2-dimethyl-4H-[1,3]dioxino[4,5-c]pyridine-8-carboxylate (2) (180 mg, 0.5 mmol) at 0° C. and stirred at room temperature for 2 hours. Evaporation under reduced pressure afforded a residue 5-((4-fluorophenylamino)methyl)-3-hydroxy-4-(hydroxymethyl) picolinate (compound 21b), which was triturated in acetonitrile. MS-ESI m/z 307 [MH]$^+$ Step 21c: Preparation of N$^5$-(3,4-difluorobenzyl)-N$^2$,3-dihydroxy-4-(hydroxymethyl)pyridine-2,5-dicarboxamide (Product 21)

Diisopropylethylamine (142 µL, 0.8 mmol) and hydroxylamine hydrochloride (45 mg, 0.64 mmol) were added to a solution of 5-((4-fluorophenylamino)methyl)-3-hydroxy-4-(hydroxymethyl)picolinate (compound 21b) (50.0 mg, 0.16 mmol) in methanol (1.0 mL). The reaction mixture was heated to 55° C. for 16 h. The reaction mixture was allowed to cool to room temperature and a saturated solution of ammonium chloride was added. The reaction mixture was extracted with ethyl acetate (3×25 mL) and the combined organic layers were dried (anh. Na₂SO₄), filtered and concentrated under reduced pressure to give a solid residue which was recrystallised in acetonitrile to give compound 21.

¹H-NMR (500 MHz, DMSO-d₆) δ ppm 8.24 (s, 1H), 7.45 (m, 4H), 4.94 (s, 2H), 3.77 (s, 2H), 3.33 (s, 2H); MS-ESI m/z 308 [MH]⁺

Example 22

Preparation of 5-{[2-(4-Fluoro-phenyl)-ethylamino]-methyl}-3-hydroxy-4-hydroxymethyl-pyridine-2-carboxylic acid hydroxyamide (Product 22)

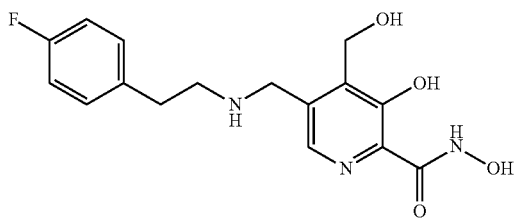 [SMILES: O=C(NO)c1ncc(CNCCc2ccc(F)cc2)c(CO)c1O]

Step 22a: Preparation of Methyl 5-((4-fluorophenethylamino)methyl)-2,2-dimethyl-4H-[1,3]dioxino[4,5-c]pyridine-8-carboxylate

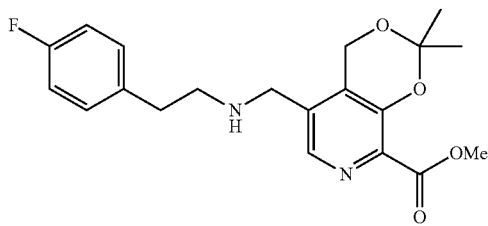 [SMILES: COC(=O)c1ncc(CNCCc2ccc(F)cc2)c2c1OC(C)(C)OC2]

Methyl 5-((4-fluorophenethylamino)methyl)-2,2-dimethyl-4H-[1.3]dioxino[4,5-c]pyridine-8-carboxylate (compound 22a) was synthesized from methyl 5-formyl-2,2-dimethyl-4H-[1,3]dioxino[4,5-c]pyridine-8-carboxylatein and 4-fluorophenethylamine as described in example 21. MS-ESI m/z 375 [MH]⁺.

Step 22b: Preparation of Methyl 5-((4-fluorophenethylamino)methyl)-3-hydroxy-4-(hydroxymethyl)picolinate

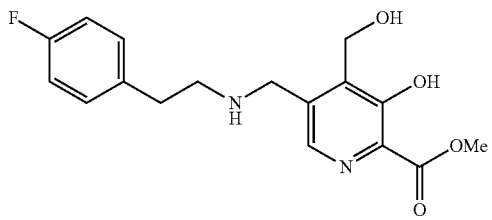 [SMILES: COC(=O)c1ncc(CNCCc2ccc(F)cc2)c(CO)c1O]

Methyl 5-((4-fluorophenethylamino)methyl)-3-hydroxy-4-(hydroxymethyl)picolinate (3) was synthesized starting from methyl 5-((4-fluorophenethylamino)methyl)-2,2-dimethyl-4H-[1,3]dioxino[4,5-c]pyridine-8-carboxylate (compound 22a) as described in example 21. MS-ESI m/z 335 [MH]⁺

Step 22c: Preparation of Product 22

Product 22 was synthesized following a procedure similar to the one described above for the synthesis of 5-((4-fluorophenylamino)methyl)-N,3-dihydroxy-4-(hydroxymethyl)picolinamide starting from methyl 5-((4-fluorophenethylamino)methyl)-3-hydroxy-4-(hydroxymethyl)picolinate (compound 22b). ¹H-NMR (500 MHz, DMSO-d₆) δ ppm 8.08 (s, 1H), 7.24 (m, 2H), 7.09 (t, J=7.2 Hz, 2H), 4.58 (s, 2H), 3.92 (s, 2H), 2.80 (m, 2H), 2.76 (m, 2H). MS-ESI m/z 336 [MH]⁺

Example 23

Preparation of 5-(4-Fluoro-benzoylamino)-3-hydroxy-4-hydroxymethyl-pyridine-2-carboxylic Acid Hydroxyamide (Product 23)

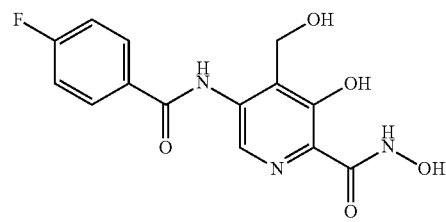 [SMILES: O=C(Nc1cnc(C(=O)NO)c(O)c1CO)c1ccc(F)cc1]

Step 23a: Preparation of 8-(methoxycarbonyl)-2,2-dimethyl-4H-[1,3]dioxino[4,5-c]pyridine-5-carboxylic Acid (Compound 23a)

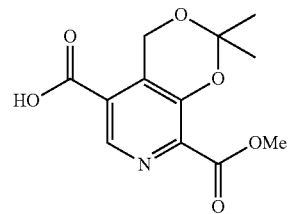 [SMILES: COC(=O)c1ncc(C(=O)O)c2c1OC(C)(C)OC2]

8-(methoxycarbonyl)-2,2-dimethyl-4H-[1,3]dioxino[4,5-c]pyridine-5-carboxylic acid (23a) was synthesized from 5-Formyl-2,2-dimethyl-4H-[1,3]dioxino[4,5-c]pyridine-8-carboxylic acid methyl ester [*J. Org. Chem.* 1999, 64, 4537] 1 mmol and 1.5 mmol NaClO₂ in t-butanol/water Step 23b: Preparation of Methyl 5-(benzyloxycarbonylamino)-2,2-dimethyl-4H-[1,3]dioxino[4,5-c]pyridine-8-carboxylate (Compound 23b)

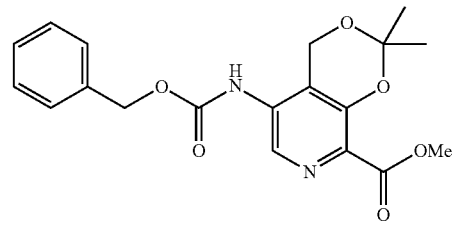 [SMILES: COC(=O)c1ncc(NC(=O)OCc2ccccc2)c2c1OC(C)(C)OC2]

Methyl 5-(benzyloxycarbonylamino)-2,2-dimethyl-4H-[1,3]dioxino[4,5-c]pyridine-8-carboxylate (23b) was made according to the following procedure: diphenyl phosphorylazide (275 µL, 1.46 mmol) was added to a mixture of 8-(methoxycarbonyl)-2,2-dimethyl-4H-[1,3]dioxino[4,5-c]pyridine-5-carboxylic acid (compound 23a) (390 mg, 1.46 mmol) and triethylamine (205 µL, 1.46 mmol) in DMF (7 mL). This mixture was stirred for 3 h and water was added. The reaction mixture was then extracted with ethyl ether (3×25 mL) and the combined organic layers were washed with saturated sodium bicarbonate, dried (anh. Na$_2$SO$_4$), filtered and concentrated under reduced pressure to give a solid, the acylazide intermediate. This intermediate was dissolved in toluene (5 mL) and benzyl alcohol (1.1 mL) was added. The mixture was heated to reflux for 4 h. and allowed to cool at room temperature. Evaporation afforded a residue which was purified by silica gel with methanol/dichloromethane (5% to 35%).

Step 23c: Preparation of 5-Amino-2,2-dimethyl-4H-[1,3]dioxino[4,5-c]pyridine-8-carboxylic Acid Methyl Ester (Compound 23c)

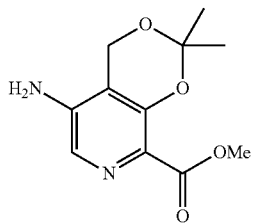 [SMILES: COC(=O)c1ncc(N)c2c1OC(C)(C)OC2]

A mixture of methyl 5-(benzyloxycarbonylamino)-2,2-dimethyl-4H-[1,3]dioxino[4,5-c]pyridine-8-carboxylate (Compound 23b) (110 mg, 0.25 mmol) and palladium on charcoal 10% (20 mg) in methanol was vigorously stirred at room temperature for 12 h. under an atmosphere of hydrogen. Filtration through Celite and evaporation afforded the aniline, compound 23c. MS-ESI m/z 239 [MH]$^+$.

Step 23d: Preparation of Methyl 5-(4-fluorobenzamido)-2,2-dimethyl-4H-[1,3]dioxino[4,5-c]pyridine-8-carboxylate (Compound 23d)

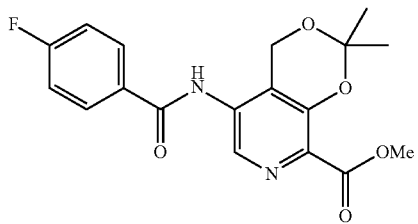 [SMILES: COC(=O)c1ncc(NC(=O)c2ccc(F)cc2)c2c1OC(C)(C)OC2]

A mixture of methyl 5-amino-2,2-dimethyl-4H-[1,3]dioxino[4,5-c]pyridine-8-carboxylate (23c) (70 mg, 0.25 mmol), 4-fluorobenzoyl chloride (35 µL, 0.27 mmol) and 4-dimethylaminopyridine in pyridine (1 mL) was stirred at room temperature overnight and a saturated solution of ammonium chloride was added. The reaction mixture was extracted with dichloromethane (3×25 mL) and the combined organic layers were dried (anh. Na$_2$SO$_4$), filtered and concentrated under reduced pressure to give methyl 5-(4-fluorobenzamido)-2,2-dimethyl-4H-[1,3]dioxino[4,5-c]pyridine-8-carboxylate (23d) as a white solid MS-ESI m/z 361 [MH]$^+$.

Step 23e: Preparation of Methyl 5-(4-fluorobenzamido)-3-hydroxy-4-(hydroxymethyl)picolinate (Compound 23e)

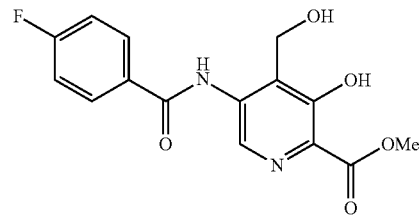 [SMILES: COC(=O)c1ncc(NC(=O)c2ccc(F)cc2)c(CO)c1O]

Methyl 5-(4-fluorobenzamido)-3-hydroxy-4-(hydroxymethyl)picolinate (23e) was synthesized from methyl 5-(4-fluorobenzamido)-2,2-dimethyl-4H-[1,3]dioxino[4,5-c]pyridine-8-carboxylate (Compound 23d) and formic acid as described above. MS-ESI m/z 361 [MH]$^+$.

Step 23f: Preparation of Product 23

5-(4-fluorobenzamido)-N,3-dihydroxy-4-(hydroxymethyl)picolinamide was synthesized from methyl 5-(4-fluorobenzamido)-3-hydroxy-4-(hydroxymethyl)picolinate (compound 23e) using the procedure described in Example 22. MS-ESI m/z 322 [MH]$^+$.

Example 24

Preparation of (8-Hydroxycarbamoyl-2,2-dimethyl-4H-[1,3]dioxino[4,5-c]pyridin-5-yl)-carbamic Acid Benzyl Ester (Product 24)

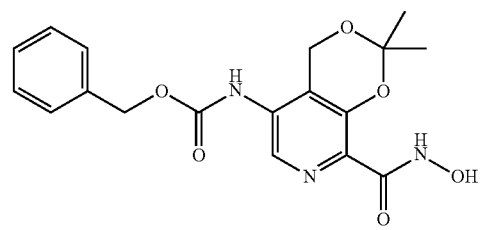 [SMILES: CC1(C)OCc2c(NC(=O)OCc3ccccc3)cnc(C(=O)NO)c2O1]

Benzyl 8-(hydroxycarbamoyl)-2,2-dimethyl-4H-[1,3]dioxino[4,5-c]pyridin-5-ylcarbamate was prepared from methyl 5-(benzyloxycarbonylamino)-2,2-dimethyl-4H-[1,3]dioxino[4,5-c]pyridine-8-carboxylate (23b) according to the procedure described in Example 23. MS-ESI m/z 374 [MH]$^+$.

Example 25

Preparation of 5-{[Benzyl-(4-fluoro-phenyl)-amino]-methyl}-3-hydroxy-4-hydroxymethyl-pyridine-2-carboxylic Acid Hydroxyamide (Product 25)

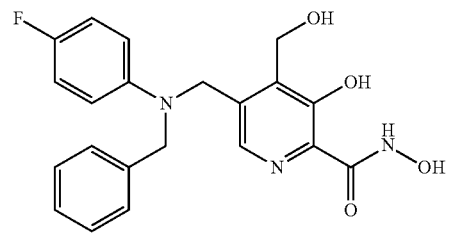 [SMILES: O=C(NO)c1ncc(CN(Cc2ccccc2)c2ccc(F)cc2)c(CO)c1O]

Step 25a: Preparation of Methyl 5-((benzyl(4-fluorophenyl)amino)methyl)-2,2-dimethyl-4H-[1,3]dioxino[4,5-c]pyridine-8-carboxylate (Compound 25a)

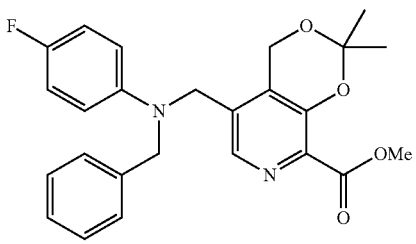 [SMILES: COC(=O)c1ncc(CN(Cc2ccccc2)c2ccc(F)cc2)c2c1OC(C)(C)OC2]

Methyl 5-((benzyl(4-fluorophenyl)amino)methyl)-2,2-dimethyl-4H-[1,3]dioxino[4,5-c]pyridine-8-carboxylate 25a was prepared from methyl 5-((4-fluorophenylamino)methyl)-2,2-dimethyl-4H-[1,3]dioxino[4,5-c]pyridine-8-carboxylate (21a) (120 mg, 0.3 mmol), benzaldehyde (100 uL, 1.0 mmol) and sodium cyanoborohydride (28 mg, 0.45 mmol) according to the procedure described in Example 24. MS-ESI m/z 437 [MH]$^+$.

Step 25b: Preparation of Product 25

Product 25 was obtained by analogous procedures to Example 21 Step 21b and 21c. MS-ESI m/z 398 [MH]$^+$.

Example 26

Preparation of 5-({(2-Benzyloxy-ethyl)-[2-(4-fluorophenyl)-ethyl]-amino}-methyl)-3-hydroxy-4-hydroxymethyl-pyridine-2-carboxylic Acid Hydroxyamide (Product 26)

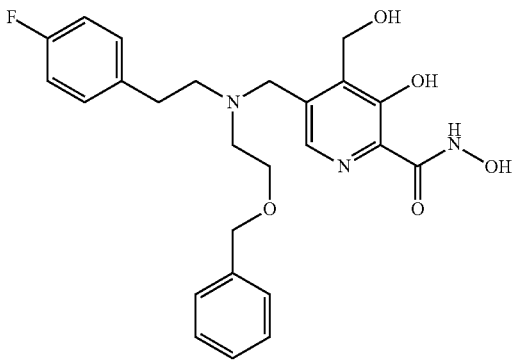 [SMILES: O=C(NO)c1ncc(CN(CCOCc2ccccc2)CCc2ccc(F)cc2)c(CO)c1O]

Step 26a: Preparation of Compound 26a

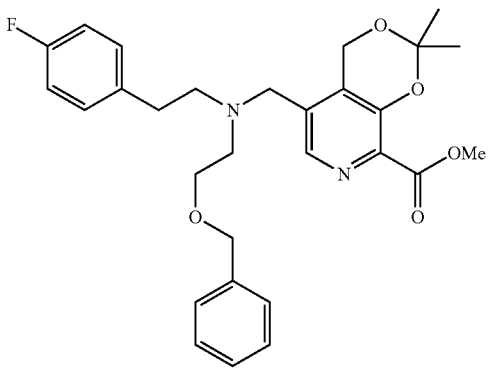 [SMILES: COC(=O)c1ncc(CN(CCOCc2ccccc2)CCc2ccc(F)cc2)c2c1OC(C)(C)OC2]

Methyl 5-(((2-(benzyloxy)ethyl)(4-fluorophenethyl)amino)methyl)-3-hydroxy-4-(hydroxymethyl)picolinate (compound 22a) was reacted with benzyloxyacetaldehyde according to the procedure described above. MS-ESI m/z 509 [MH]$^+$.

Step 26b: Preparation of Methyl 5-(((2-(benzyloxy)ethyl)(4-fluorophenethyl)amino)methyl)-3-hydroxy-4-(hydroxymethyl)picolinate (Compound 26b)

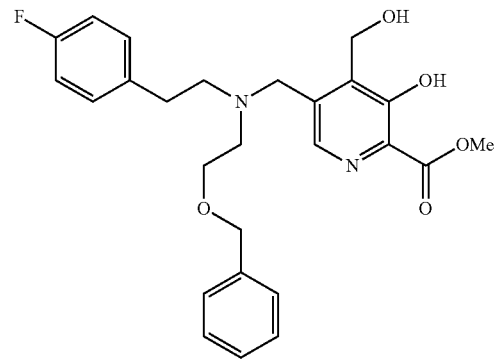 [SMILES: COC(=O)c1ncc(CN(CCOCc2ccccc2)CCc2ccc(F)cc2)c(CO)c1O]

Methyl 5-(((2-(benzyloxy)ethyl)(4-fluorophenethyl)amino)methyl)-2,2-dimethyl-4H-[1,3]dioxino[4,5-c]pyridine-8-carboxylate (compound 26a) was reacted with formic acid according to the procedure described in example 21 step 21b. MS-ESI m/z 469 [MH]$^+$.

Step 26c: Preparation of 5-({(2-Benzyloxy-ethyl)-[2-(4-fluoro-phenyl)-ethyl]-amino}-methyl)-3-hydroxy-4-hydroxymethyl-pyridine-2-carboxylic Acid Hydroxyamide (Product 26)

Product 26 was made from methyl 5-(((2-(benzyloxy)ethyl)(4-fluorophenethyl)amino)methyl)-3-hydroxy-4-(hydroxymethyl)picolinate (compound 23b) according to the procedure described in example 21 step 21c. MS-ESI m/z 470

Example 27

Preparation of 5-[3-(4-Fluoro-phenyl)-ureido]-3-hydroxy-4-hydroxymethyl-pyridine-2-carboxylic Acid Hydroxyamide (Product 27)

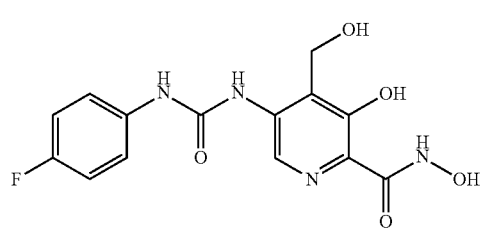 [SMILES: O=C(Nc1ccc(F)cc1)Nc1cnc(C(=O)NO)c(O)c1CO]

Step 27a Preparation of Methyl 5-(3-(4-fluorophenyl)ureido)-2,2-dimethyl-4H-[1,3]dioxino[4,5-e]pyridine-8-carboxylate (Compound 27a)

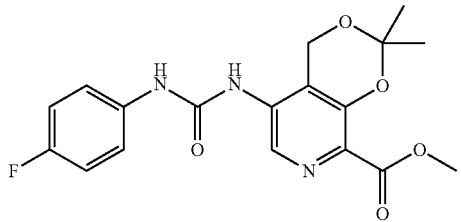 [SMILES: COC(=O)c1ncc(NC(=O)Nc2ccc(F)cc2)c2c1OC(C)(C)OC2]

Compound 27a was prepared according to the procedure described for the synthesis of methyl 5-(benzyloxycarbonylamino)-2,2-dimethyl-4H-[1,3]dioxino[4,5-c]pyridine-8-carboxylate (23b) above, except that in the second step, benzyl alcohol was substituted by 4-fluoroaniline. MS-ESI m/z 376 [MH]+.

Step 27b: Preparation of Methyl 5-(3-(4-fluorophenyl)ureido)-3-hydroxy-4-(hydroxymethyl)picolinate (Compound 27b)

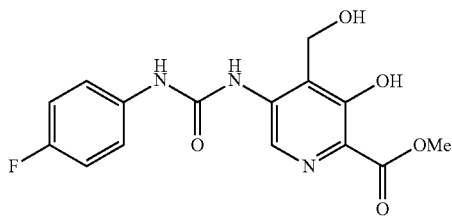 [SMILES: COC(=O)c1ncc(NC(=O)Nc2ccc(F)cc2)c(CO)c1O]

Compound 27b was made from methyl 5-(3-(4-fluorophenyl)ureido)-2,2-dimethyl-4H-[1,3]dioxino[4,5-c]pyridine-8-carboxylate 27a according to the procedure described in example 23, step 23e. MS-ESI m/z 337 [MH]+.

Step 27c: Preparation of 5-[3-(4-Fluoro-phenyl)-ureido]-3-hydroxy-4-hydroxymethyl-pyridine-2-carboxylic Acid Hydroxyamide (Product 27)

Product 27 was made from methyl 5-(3-(4-fluorophenyl)ureido)-3-hydroxy-4-(hydroxymethyl)picolinate 27b according to the procedure described above. MS-ESI m/z 336 [MH]+.

Example 28

Preparation of 5-(4-Fluoro-phenoxymethyl)-3-hydroxy-4-hydroxymethyl-pyridine-2-carboxylic Acid Hydroxyamide (Product 28)

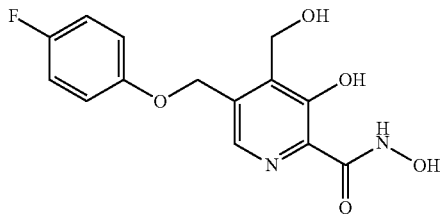 [SMILES: O=C(NO)c1ncc(COc2ccc(F)cc2)c(CO)c1O]

Step 28a: Preparation of Methyl 5-((4-fluorophenoxy)methyl)-2,2-dimethyl-4H-[1,3]dioxino[4,5-c]pyridine-8-carboxylate (Compound 28a)

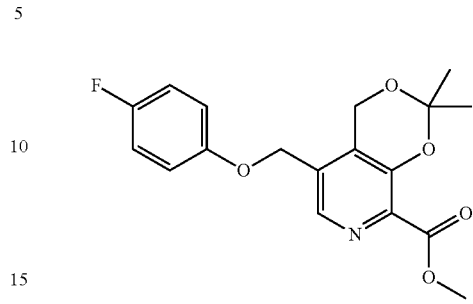

Triphenylphosphine (0.105 g, 0.40 mmol), followed by diethyl azodicarboxylate (DEAD) (0.06 mL, 0.40 mmol) were added to a solution of methyl 5-(hydroxymethyl)-2,2-dimethyl-4H-[1,3]dioxino[4,5-c]pyridine-8-carboxylate (0.102 g, 0.40 mmol) in 10 mL of THF, at room temperature under Ar. The resulting mixture was stirred at room temperature for 6 h and then concentrated. The crude residue was purified by chromatography (SiO$_2$) with hexanes:ethyl acetate (1:1) as eluent to afford the title compound with a contaminant. LC-MS (M+H)+ m/z 348.

Step 28b: Preparation of Methyl 5-((4-fluorophenoxy)methyl)-3-hydroxy-4-(hydroxymethyl)picolinate (Compound 28b)

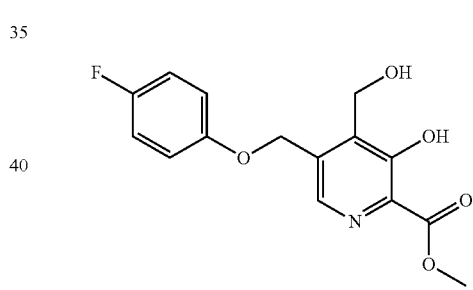

A solution of methyl 5-((4-fluorophenoxy)methyl)-2,2-dimethyl-4H-[1,3]dioxino[4,5-c]pyridine-8-carboxylate 28a (0.129 g, 0.37 mmol) in 3 mL of formic acid was stirred at 23° C. for 2 h and then it was concentrated. The crude residue was purified by chromatography (SiO$_2$) with hexanes:ethyl acetate (3:7) as eluent to afford the title compound as a white solid: LC-MS (M+H)+ m/z 308; $^1$H NMR (DMSO-d$_6$): 1.39 (s, 6H), 4.80 (s, 2H), 4.89 (s, 2H), 5.01 (s, 2H), 7.39-7.46 (m, 5H), 8.38 (s, 1H), 10.04 (s, 1H).

Step 28c: Preparation of Product 28

Hydroxylamine hydrochloride (0.045 g, 0.65 mmol) and N,N-diisopropylethylamine (0.14 mL, 0.81 mmol) were added to a solution of methyl 5-((4-fluorophenoxy)methyl)-3-hydroxy-4-(hydroxymethyl)picolinate 28b (0.050 g, 0.16 mmol) in MeOH (3 mL) and heated to 70° C. for 5 h. The crude mixture was diluted with EtOAc and washed with saturated aqueous ammonium chloride solution and brine. The organic extract was dried (Na₂SO₄), filtered and concentrated in vacuo to afford the title compound (0.048 g, 96%): LC-MS (M+H)⁺ m/z 309.

Example 29

Preparation of 5-(3-Chloro-4-fluoro-phenoxymethyl)-3-hydroxy-4-hydroxymethyl-pyridine-2-carboxylic Acid Hydroxyamide (Product 29)

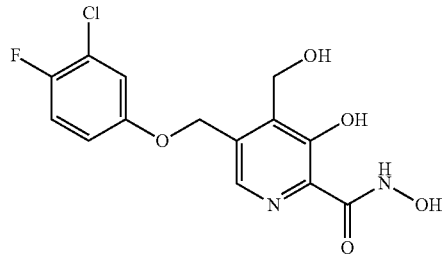 [SMILES: O=C(NO)c1ncc(COc2ccc(F)c(Cl)c2)c(CO)c1O]

Step 29a: Preparation of Methyl 5-((3-chloro-4-fluorophenoxy)methyl)-2,2-dimethyl-4H-[1,3]dioxino[4,5-c]pyridine-8-carboxylate (Compound 29a)

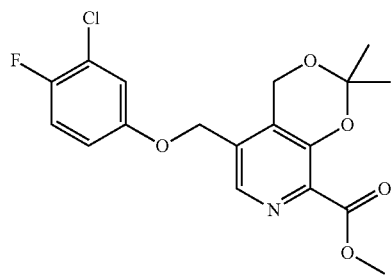 [SMILES: COC(=O)c1ncc(COc2ccc(F)c(Cl)c2)c2c1OC(C)(C)OC2]

Using similar procedure as described in the example of methyl 5-((4-fluorophenoxy)methyl)-2,2-dimethyl-4H-[1,3]dioxino[4,5-c]pyridine-8-carboxylate (step 28a), we obtained compound 29a: ESI-MS (M+H)⁺ m/z 382.

Step 29b: Preparation of Methyl 5-((3-chloro-4-fluorophenoxy)methyl)-3-hydroxy-4(hydroxymethyl)picolinate (compound 29b)

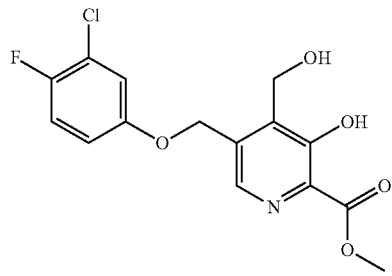 [SMILES: COC(=O)c1ncc(COc2ccc(F)c(Cl)c2)c(CO)c1O]

Using similar procedure as described in the example 28, in the preparation of methyl 5-((4-fluorophenoxy)methyl)-3-hydroxy-4-(hydroxymethyl)picolinate 28b, we obtained compound 29b as a white solid: yield (63%); LC-MS (M+H)⁺ m/z 342.

Step 29c: Preparation of Product 29

Using similar procedure as described in the example 28, in the preparation of 5-((4-fluorophenoxy)methyl)-N,3-dihydroxy-4-(hydroxymethyl)picolinamide 28c, we obtained Product 29 as a beige solid: yield (98%); LC-MS (M+H)⁺ m/z 342.

Example 30

Preparation of 5-(3-Chloro-4-fluoro-benzyloxymethyl)-3-hydroxy-4-hydroxymethyl-pyridine-2-carboxylic Acid Hydroxyamide (Product 30)

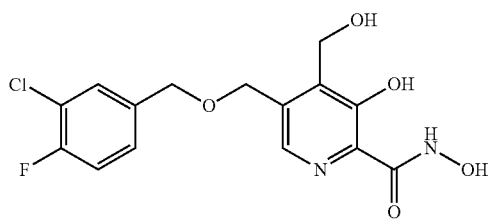 [SMILES: O=C(NO)c1ncc(COCc2ccc(F)c(Cl)c2)c(CO)c1O]

Product 30 was prepared in a procedure analogous to that shown in example 20 with the exception of the use of 4-fluoro-3-chloro-benzyl chloride as alkylating agent. LC-MS (M+H)⁺ m/z 357.7.

Example 31

Preparation of 5-[2-(4-Fluoro-phenyl)-ethoxymethyl]-3-hydroxy-4-hydroxymethyl-pyridine-2-carboxylic Acid Hydroxyamide (Product 31)

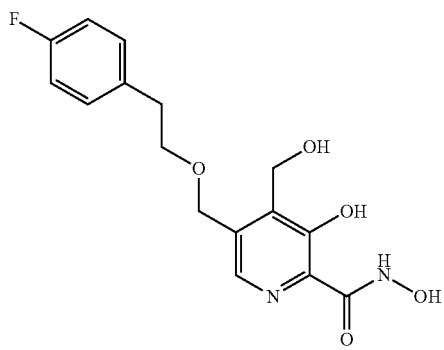 [SMILES: O=C(NO)c1ncc(COCCc2ccc(F)cc2)c(CO)c1O]

Product 31 was prepared in a procedure analogous to that shown in example 20 with the exception of the use of 4-fluoro-3-chloro-benzyl chloride as alkylating agent. LC-MS (M+H)⁺ m/z 337.

Example 32

Preparation of 5-(2,4-Difluoro-benzyloxymethyl)-3-hydroxy-4-hydroxymethyl-pyridine-2-carboxylic Acid Hydroxyamide (Product 32)

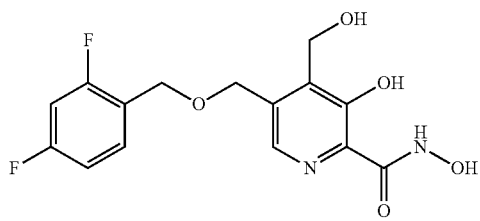 [SMILES: O=C(NO)c1ncc(COCc2ccc(F)cc2F)c(CO)c1O]

Product 32 was prepared in a procedure analogous to that shown in example 20 with the exception of the use of 2,4-difluoro-benzyl chloride as alkylating agent. LC-MS (M+H)⁺ m/z 341.

Example 33

Preparation of 5-(3,4-Difluoro-benzyloxymethyl)-3-hydroxy-4-hydroxymethyl-pyridine-2-carboxylic Acid Hydroxyamide (Product 33)

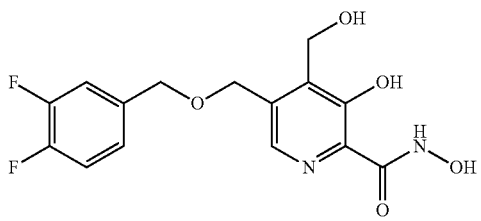 [SMILES: O=C(NO)c1ncc(COCc2ccc(F)c(F)c2)c(CO)c1O]

Product 33 was prepared in a procedure analogous to that shown in example 20 with the exception of the use of 3,4-difluoro-benzyl chloride as alkylating agent. LC-MS (M+H)⁺ m/z 341.

Example 34

Preparation of 5-(4-Fluoro-benzyloxymethyl)-3-hydroxy-4-hydroxymethyl-pyridine-2-carboxylic Acid Hydroxyamide

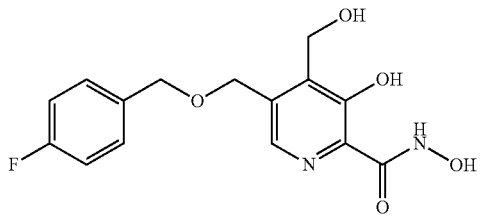 [SMILES: O=C(NO)c1ncc(COCc2ccc(F)cc2)c(CO)c1O]

Product 34 was prepared in a procedure analogous to that shown in example 20 with the exception of the use of 4-fluoro-benzyl chloride as alkylating agent. LC-MS (M+H)⁺ m/z 323.

Example 35

Preparation of 5-(4-Fluoro-phenoxymethyl)-3-hydroxy-4-methyl-pyridine-2-carboxylic Acid Hydroxyamide (Product 35)

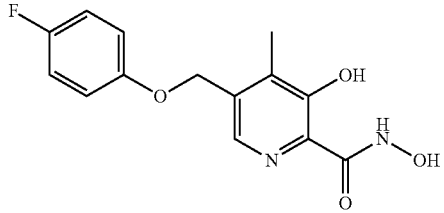 [SMILES: Cc1c(COc2ccc(F)cc2)cnc(C(=O)NO)c1O]

Step 35a: Preparation of Methyl 3-(benzyloxy)-5-((4-fluorophenoxy)methyl)-4-methylpicolinate (Compound 35a)

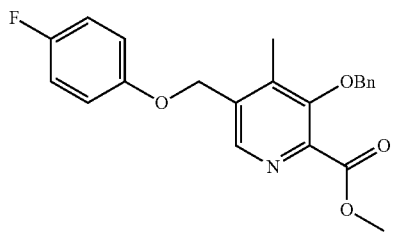 [SMILES: COC(=O)c1ncc(COc2ccc(F)cc2)c(C)c1OCc1ccccc1]

Using a procedure similar to that described in the example 28 in the preparation of methyl 5-((4-fluorophenoxy)methyl)-2,2-dimethyl-4H-[1,3]dioxino[4,5-c]pyridine-8-carboxylate 28a, we obtained 35a as a colorless oil: Yield (72%); LC-MS (M+H)$^F$ m/z 382.

Step 35b: Preparation of Methyl 5-((4-fluorophenoxy)methyl)-3-hydroxy-4-methylpicolinate (Compound 35b)

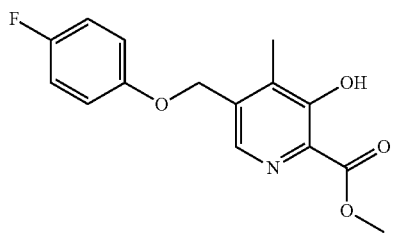 [SMILES: COC(=O)c1ncc(COc2ccc(F)cc2)c(C)c1O]

A solution of methyl 3-(benzyloxy)-5-((4-fluorophenoxy)methyl)-4-methylpicolinate 35a (0.245 g, 0.64 mmol) in ethyl acetate (10 mL) was hydrogenated under 1 atm of hydrogen at 23° C. over 10% palladium on activated carbon for 1 h. The reaction mixture was filtrated and the solution was concentrated in vacuo to afford 35b as a white solid (0.171 g, 92%): LC-MS (M+H)⁺ m/z 292.

Step 35c: Preparation of Product 35

Using similar procedure as described in the example 28 in the preparation of 5-((4-fluorophenoxy)methyl)-N,3-dihydroxy-4-(hydroxymethyl)picolinamide, (28c)
Product 35 was obtained as an off-white solid: Yields (97%); LC-MS (M+H)⁺ m/z 293.

Example 36

Preparation of 5-(3-Chloro-4-fluoro-phenoxymethyl)-3-hydroxy-4-methyl-pyridine-2-carboxylic Acid Hydroxyamide (Product 36)

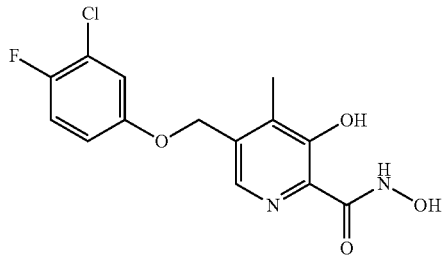 [SMILES: Cc1c(COc2ccc(F)c(Cl)c2)cnc(C(=O)NO)c1O]

Step 36a: Preparation of Methyl 3-(benzyloxy)-5-((3-chloro-4-fluorophenoxy)methyl)-4-methylpic (Compound 36a)

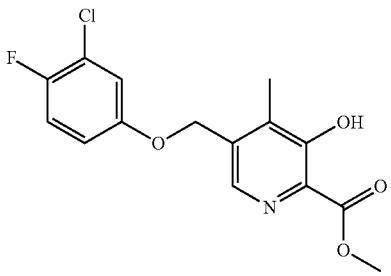 [SMILES: COC(=O)c1ncc(COc2ccc(F)c(Cl)c2)c(C)c1O]

Using similar procedure as described in the example of Methyl 3-(benzyloxy)-5-((4-fluorophenoxy)methyl)-4-methylpicolinate, (example 35a) we obtained the title compound as a colorless oil: Yields (68%); LC-MS (M+H)+ m/z 416.

Step 36b: Preparation of Methyl 5-((3-chloro-4-fluorophenoxy)methyl)-3-hydroxy-4-methylpicolinate (Compound 36b)

A solution of methyl 3-(benzyloxy)-5-((3-chloro-4-fluorophenoxy)methyl)-4-methylpicolinate (0.167 g, 0.13 mmol) in trifluoroacetic acid (6 mL) was stirred at 23° C. for 2 days. The solvent was then removed in vacuo and an aqueous solution of NaHCO$_3$ (1M) was added, followed by extraction with ethyl acetate. The combined organic extracts were washed with brine, dried (Na$_2$SO$_4$), filtered and concentrated. The crude residue was purified by flash chromatography (SiO$_2$) with hexane:ethyl acetate (7:3) as eluent to afford 36b as a white solid (0.113 g, 86%): LC-MS (M+H)+ m/z 326.

Step 36c: Preparation of Product 36

Using a procedure similar to that described in the example 28 in the preparation of 5-((4-fluorophenoxy)methyl)-N,3-dihydroxy-4-(hydroxymethyl)picolinamide, (28c) Product 36 was obtained as an off-white solid: Yield (100%); LC-MS (M+H)+ m/z 327.

Example 37

Preparation of 5-(2,4-Difluoro-benzyloxymethyl)-3-hydroxy-4-methyl-pyridine-2-carboxylic Acid Hydroxyamide (Product 37)

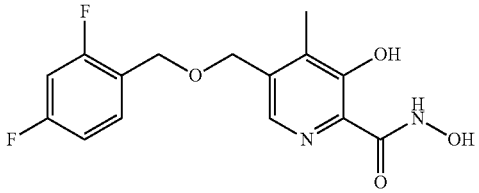 [SMILES: Cc1c(COCc2ccc(F)cc2F)cnc(C(=O)NO)c1O]

Product 37 was prepared using a procedure analogous to that shown in example 20 with the exception of the use of 4-fluoro-3-chloro-benzyl chloride as an alkylating agent, and 3-Benzyloxy-5-hydroxymethyl-4-methyl-pyridine-2-carboxylic acid methyl ester: LC-MS (M+H)+ m/z 325.

Example 38

Preparation of 5-(3,4-Difluoro-benzyloxymethyl)-3-hydroxy-4-methyl-pyridine-2-carboxylic Acid Hydroxyamide (Product 38)

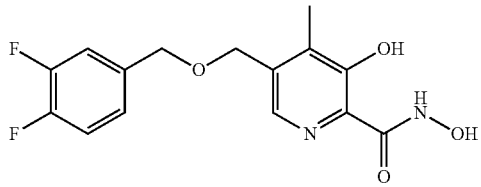 [SMILES: Cc1c(COCc2ccc(F)c(F)c2)cnc(C(=O)NO)c1O]

Product 38 was prepared using a procedure analogous to that shown in example 20 with the exception of the use of 3,4-difluoro-benzyl chloride as the alkylating agent and 3-Benzyloxy-5-hydroxymethyl-4-methyl-pyridine-2-carboxylic acid methyl ester. LC-MS (M+H)+ m/z 325.

Example 39

Preparation of 5-(4-Fluoro-benzyloxymethyl)-3-hydroxy-4-methyl-pyridine-2-carboxylic Acid Hydroxyamide (Product 39)

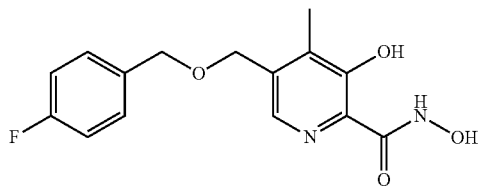 [SMILES: Cc1c(COCc2ccc(F)cc2)cnc(C(=O)NO)c1O]

Product 39 was prepared using a procedure analogous to that shown in example 20 with the exception of the use of 4-fluorobenzyl chloride as the alkylating agent and 3-Benzyloxy-5-hydroxymethyl-4-methyl-pyridine-2-carboxylic acid methyl ester. LC-MS (M+H)+ m/z 307.

Example 40

Preparation of 5-Benzyloxymethyl-3-hydroxy-4-methyl-pyridine-2-carboxylic Acid Hydroxyamide (Product 40)

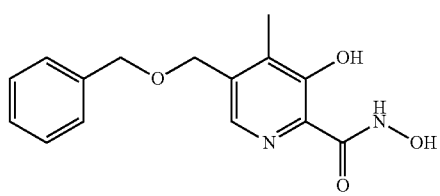 [SMILES: Cc1c(COCc2ccccc2)cnc(C(=O)NO)c1O]

Product 40 was prepared using a procedure analogous to that shown in example 20 with the exception of the use of benzyl chloride as the alkylating agent and 3-Benzyloxy-5- hydroxymethyl-4-methyl-pyridine-2-carboxylic acid methyl ester. LC-MS (M+H)⁺ m/z 389.

Example 41

Preparation of (S)-(−)-3-Hydroxy-4-hydroxymethyl-pyridine-2,5-dicarboxylic Acid 2-hydroxyamide 5-[(1-phenyl-ethyl)-amide](Product 41)

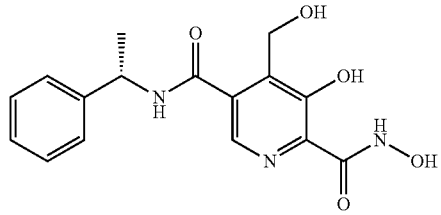 [SMILES: C[C@H](NC(=O)c1cnc(C(=O)NO)c(O)c1CO)c1ccccc1]

Step 41a: Preparation of Compound 41a

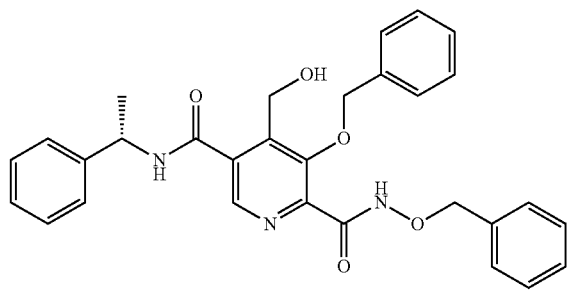 [SMILES: C[C@H](NC(=O)c1cnc(C(=O)NOCc2ccccc2)c(OCc2ccccc2)c1CO)c1ccccc1]

(S)-(−)-α-Methylbenzylamine (0.027 g, 0.226 mmol, 2.2 eq) and III (scheme I) (0.040 g, 0.103 mmol, 1 eq) were heated neat at 70° C. for 20 min. The crude product was purified by silica gel (50% ethyl acetate/hexane) to give 0.043 g of 41a (83%) as a white solid. MS-ESI m/z 512 [MH]⁺.

Step 41b: Preparation of Product 41

(0.040 g, 0.078 mmol, 1 eq) and 10% Pd/C (5 mg) in methanol (4.0 mL) were stirred under an atmosphere of hydrogen 1 hour. The catalyst was filtered and reaction mixture was concentrated under vacuum to give 0.015 g of 41b (58%) as a white solid. ¹H-NMR (400 MHz, MeOD): δ=8.16 (s, 1H), 7.42 (m, 5H), 4.75 (s, 2H), 4.59 (s, 2H), 1.58 (s, 3H); MS-ESI m/z 332 [MH]⁺.

Example 42

Preparation of 3-Hydroxy-4-hydroxymethyl-pyridine-2,5-dicarboxylic Acid 2-hydroxyamide 5-[(pyridin-2-ylmethyl)-amide](Product 42)

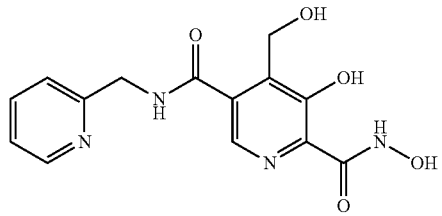 [SMILES: O=C(NCc1ccccn1)c1cnc(C(=O)NO)c(O)c1CO]

Step 42a: Preparation of xxx (Compound 42a)

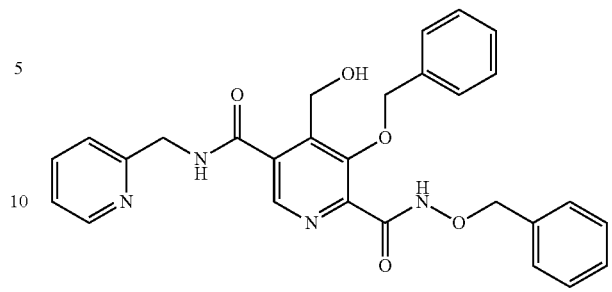

2-(Aminomethyl)pyridine (0.024 g, 0.226 mmol, 2.2 eq) and 111 (Scheme I) (0.040 g, 0.103 mmol, 1 eq) were heated neat at 70° C. for 20 min to give compound 42a. MS-ESI m/z 499 [MH]⁺.

Step 42b: Preparation of Product 42

Compound 42a (0.103 mmol, 1 eq) and 10% Pd/C (5 mg) in methanol (4.0 mL) were stirred under an atmosphere of hydrogen 1 hour. The catalyst was filtered and triturated with diethyl ether and acetonitrile and precipitated with MeOH/aceotnitrile to give 0.003 g of Product 42 (1%) as a white solid. ¹H-NMR (400 MHz, MeOD): δ=8.53 (d, J=5.7 Hz, 1H), 8.12 (s, 1H), 7.84 (m, 1H), 7.55 (d, J=7.7 Hz, 1H), 7.34 (m, 1H), 4.90 (s, 2H), 4.58 (s, 2H); MS-ESI m/z 319 [MH]⁺.

Example 43

Preparation of 3-Hydroxy-4-hydroxymethyl-pyridine-2,5-dicarboxylic Acid 5-benzylamide 2-hydroxyamide (Product 43)

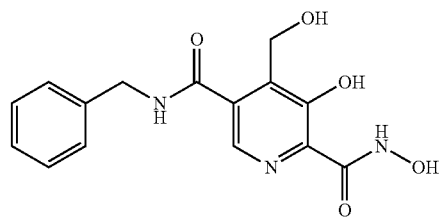 [SMILES: O=C(NCc1ccccc1)c1cnc(C(=O)NO)c(O)c1CO]

Step 43a: Preparation of Compound 43a

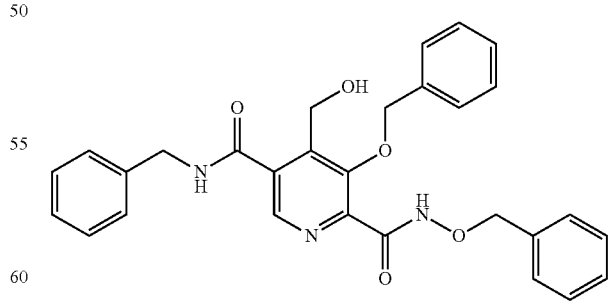

Benzylamine (0.024 g, 0.235 mmol, 2.5 eq) and 111 (Scheme I) (0.040 g, 0.103 mmol, 1 eq) were heated neat at 70° C. for 20 min. The crude product was purified by silica gel (60% ethyl acetate/hexane) to give 0.012 g of compound 43a (24%) as a white solid. MS-ESI m/z 498 [MH]⁺.

Step 43b: Preparation of Product 43

Compound 43a (0.012 g, 0.024 mmol, 1 eq) and 10% Pd/C (5 mg) in methanol (4.0 mL) were stirred under an atmosphere of hydrogen 1 hour. The catalyst was filtered and reaction mixture was concentrated under vacuum to give 0.008 g of 43b (75%) as a white solid. MS-ESI m/z 318 [MH]$^+$.

Example 44

Preparation of (S)-(−)-3-Hydroxy-4-hydroxymethyl-pyridine-2,5-dicarboxylic Acid 2-hydroxyamide 5-[(2-hydroxy-1-phenyl-ethyl)-amide] (Product 44)

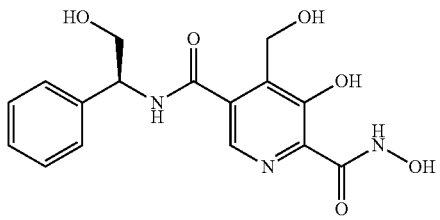 [SMILES: O=C(N[C@H](CO)c1ccccc1)c1cnc(C(=O)NO)c(O)c1CO]

Step 44a: Preparation of Compound 44a

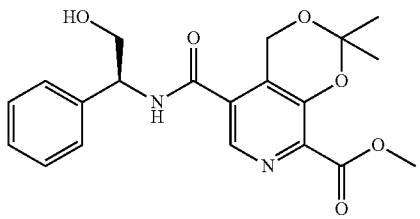 [SMILES: COC(=O)c1ncc(C(=O)N[C@H](CO)c2ccccc2)c2c1OC(C)(C)OC2]

N,N-diisopropylethylamine (0.275 g, 2.133 mmol, 3 eq) and N,N,N'',N''-Tetramethyl-O-(1H-benzotriazol-1-yl)uranium hexafluorophosphate (0.404 g, 1.067 mmol, 1.5 eq) were added to 8-(methoxycarbonyl)-2,2-dimethyl-4H-[1,3]dioxino[4,5-c]pyridine-5-carboxylic acid (23a) (0.190 g, 0.711 mmol, 1 eq) and (S)-phenylglycinol (0.107 g, 0.783 mmol, 1.1 eq) in N,N-dimethylformamide (5.0 mL). The reaction mixture was stirred at room temperature overnight. Water was added and reaction mixture was extracted with ethyl acetate. Organic phases were combined, dried over magnesium sulfate and concentrated. The crude product was purified by silica gel (75% ethyl acetate/hexane) to give 0.254 g of 44a (93%) as a white solid. MS-ESI m/z 387 [MH]$^+$.

Step 44b: Preparation of Compound 44b

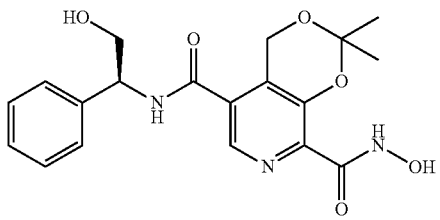 [SMILES: CC1(C)OCc2c(C(=O)N[C@H](CO)c3ccccc3)cnc(C(=O)NO)c2O1]

Hydroxylamine solution 50 wt. % in water (5.0 mL) was added to 44a (0.178 g, 0.461 mmol, 1 eq) in tetrahydrofuran (5.0 mL). The reaction mixture was stirred at reflux 3 hrs. The pH was adjusted to 6 and reaction mixture was extracted with ethyl acetate. Organic phases were combined, dried over magnesium sulfate and concentrated under vacuum to give 0.045 g of 44b (25%) as a white solid. MS-ESI m/z 388 [MH]$^+$.

Step 44c: Preparation of Product 44

To 44b (0.045 g, 0.116 mmol, 1 eq) was added formic acid (2 mL). The reaction mixture was stirred at room temperature 10 min. Formic acid was concentrated under vacuum and solid was triturated with diethyl ether to give 0.035 g of 44 (87%) as a white solid. MS-ESI m/z 348 [MH]$^+$.

Example 45

Preparation of Pyridine-2,5-dicarboxylic Acid 5-(4-fluoro-benzylamide)2-hydroxyamide (Product 45)

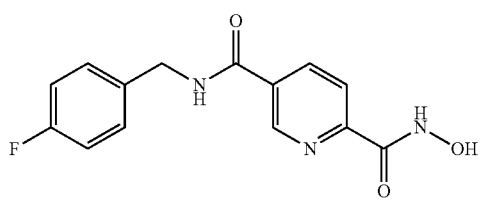 [SMILES: O=C(NCc1ccc(F)cc1)c1ccc(C(=O)NO)nc1]

Step 45a: Preparation of Compound 45a

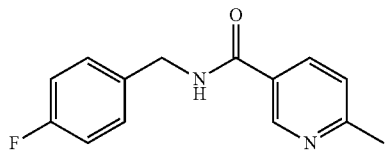 [SMILES: Cc1ccc(C(=O)NCc2ccc(F)cc2)cn1]

4-fluorobenzylamine (1.00 g, 8.02 mmol, 1.1 eq), N,N-diisopropylethylamine (0.942 g, 21.87 mmol, 3 eq) and N,N,N',N''-Tetramethyl-O-(1H-benzotriazol-1-yl)uranium hexafluorophosphate (4.15 g, 10.93 mmol, 1.5 eq) were added to 6-methylnicotinic acid (1.00 g, 7.29 mmol, 1 eq) in N-N-dimethylformamide (10.0 mL). The reaction mixture was stirred at room temperature overnight. Water was added and reaction mixture was extracted with ethyl acetate. Organic phases were combined, dried over magnesium sulfate and concentrated. The crude product was purified by silica gel (75% ethyl acetate/hexane) to give 1.44 g of 45a (80%) as a white solid. MS-ESI m/z 245 [MH]$^+$.

Step 45b: Preparation of Compound 45b

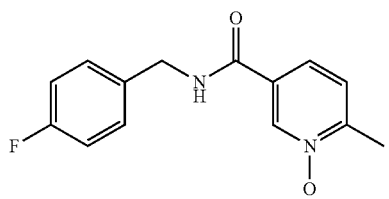

3-chloroperbenzoic acid (1.30 g, 7.56 mmol, 1.5 eq) at room temperature was added to 45a (1.23 g, 5.04 mmol, 1 eq) in dichloromethane (30.0 mL). The reaction mixture was stirred 1 hour at room temperature. A 1M solution of potassium carbonate was added and reaction mixture was extracted

Step 45c: Preparation of Compound 45a

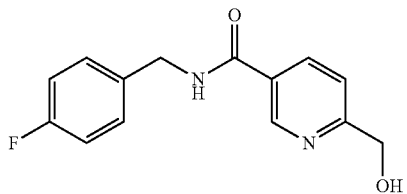 [SMILES: O=C(NCc1ccc(F)cc1)c1ccc(CO)nc1]

Trifluoroacetic anhydride (3.18 g, 15.12 mmol, 4.3 eq) at room temperature was added to 45b (0.908 g, 3.49 mmol, 1 eq) in dichloromethane (20.0 mL). The reaction mixture was stirred overnight at room temperature. A 1M solution of potassium carbonate was added and reaction mixture was extracted with ethyl acetate. Organic phases were combined, dried over magnesium sulfate and concentrated to give 0.900 g of 45c (99%) as a white solid. MS-ESI m/z 260 [MH]+.

Step 45d: Preparation of Compound 45a

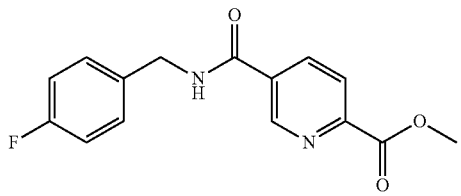 [SMILES: COC(=O)c1ccc(C(=O)NCc2ccc(F)cc2)cn1]

Activated manganese oxide (0.083 g, 0.962 mmol, 5 eq) at room temperature was added to 45c (0.050 g, 0.192 mmol, 1 eq) in chloroform (10.0 mL) and tetrahydrofuran (5.0 mL). The reaction mixture was stirred at reflux 1 hr or until all starting material disappeared by LC-MS. Solvent was concentrated under vacuo and crude reaction mixture was dissolved in methanol (10.0 mL). A solution of sodium cyanide (0.011 g, 0.230 mmol, 1.2 eq) in methanol (3.0 mL) was added and the reaction mixture was stirred 20 min. at room temperature. The reaction mixture was filtered on Celite. Organic phase was washed with water and extracted with ethyl acetate. The crude product was purified by silica gel (100% ethyl acetate/hexane) to give 0.025 g of 45d (46%) as a white solid. MS-ESI m/z 289 [MH]+.

Step 45e: Preparation of Product 45

N,N-diisopropylethylamine (0.062 g, 0.479 mmol, 6 eq) and hydroxylamine hydrochloride (0.022 g, 0.319 mmol, 4 eq) were added to 45d (0.023 g, 0.079 mmol, 1 eq) in methanol (5.0 mL). The reaction mixture was stirred at reflux 3 hrs. Water was added and reaction mixture was extracted with ethyl acetate. Organic phases were combined, dried over magnesium sulfate and concentrated under vacuum to give 0.015 g of 45 (65%) as a white solid. MS-ESI m/z 290 [MH]+.

Example 46

2,2-Dimethyl-4H-[1,3]dioxino[4,5-c]pyridine-5,8-dicarboxylic Acid 5-{[1-(4-fluoro-phenyl)-cyclopropyl]-amide}8-hydroxyamide (Product 46)

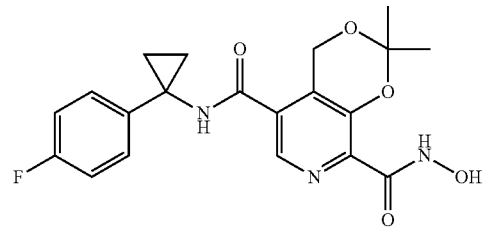 [SMILES: CC1(C)OCc2c(C(=O)NC3(c4ccc(F)cc4)CC3)cnc(C(=O)NO)c2O1]

Step 46a: Preparation of Compound 46a

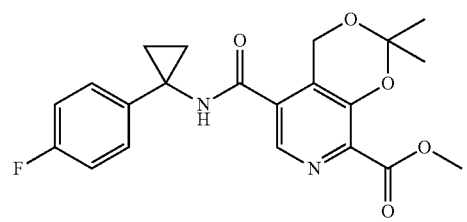 [SMILES: COC(=O)c1ncc(C(=O)NC2(c3ccc(F)cc3)CC2)c2c1OC(C)(C)OC2]

N,N-diisopropylethylamine (0.145 g, 1.12 mmol, 3 eq) and N,N,N',N''-Tetramethyl-O-(1H-benzotriazol-1-yl)uranium hexafluorophosphate (0.213 g, 0.561 mmol, 1.5 eq) were added to 8-(methoxycarbonyl)-2,2-dimethyl-4H-[1,3]dioxino[4,5-c]pyridine-5-carboxylic acid (23a) (0.100 g, 0.374 mmol, 1 eq) and 1-(4-fluorophenyl)cyclopropylamine (0.062 g, 0.412 mmol, 1.1 eq) in N,N-dimethylformamide (5.0 mL). The reaction mixture was stirred at room temperature overnight. Water was added and reaction mixture was extracted with ethyl acetate. Organic phases were combined, dried over magnesium sulfate and concentrated. The crude product was purified by silica gel (75% ethyl acetate/hexane) to give 0.254 g of 46a (93%) as a white solid. MS-ESI m/z 401 [MH]+.

Step 46b: Preparation of Product 46

To 46b (0.140 g, 0.350 mmol, 1 eq) in tetrahydrofuran (5.0 mL) was added hydroxylamine solution 50 wt. % in water (5.0 mL). The reaction mixture was stirred at reflux 3 hrs. Water was added and reaction mixture was extracted with ethyl acetate. Organic phases were combined, dried over magnesium sulfate and concentrated under vacuum to give 0.130 g of 46 (93%) as a white solid. MS-ESI m/z 402 [MH]+.

Example 47

Preparation of 3-Hydroxy-4-hydroxymethyl-pyridine-2,5-dicarboxylic Acid 5-{[1-(4-fluoro-phenyl)-cyclopropyl]-amide}2-hydroxyamide (Product 47)

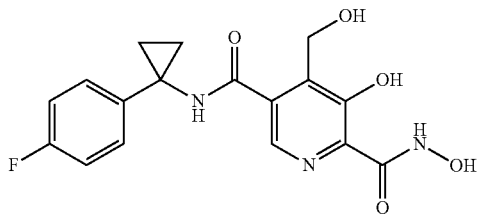 [SMILES: O=C(NC1(c2ccc(F)cc2)CC1)c1cnc(C(=O)NO)c(O)c1CO]

To 46 (0.125 g, 0.312 mmol, 1 eq) was added formic acid (2 mL). The reaction mixture was stirred at room temperature 10 min. Formic acid was concentrated under vacuum and solid was triturated with diethyl ether under to give 0.070 g of 47 (62%) as a white solid. MS-ESI m/z 362 [MH]+.

Example 48

Preparation of 2,2-Dimethyl-4H-[1,3]dioxino[4,5-c]pyridine-5,8-dicarboxylic Acid 5-(4-fluoro-benzylamide)8-(methoxy-amide) (Product 48)

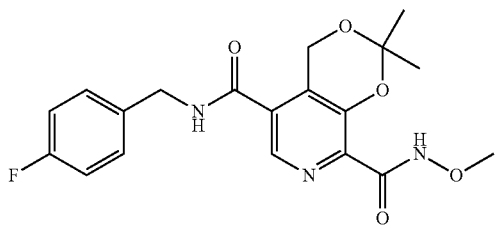 [SMILES: CONC(=O)c1ncc(C(=O)NCc2ccc(F)cc2)c2c1OC(C)(C)OC2]

Step 48a: Preparation of Compound 48a

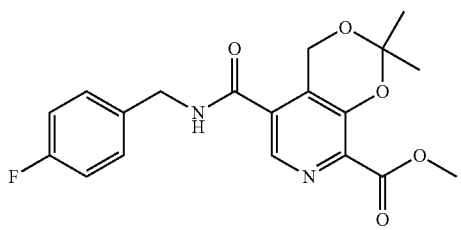 [SMILES: COC(=O)c1ncc(C(=O)NCc2ccc(F)cc2)c2c1OC(C)(C)OC2]

N,N,N',N''-Tetramethyl-O-(1H-benzotriazol-1-yl)uranium hexafluorophosphate (0.287 g, 0.758 mmol, 1.5 eq) was added to 8-(methoxycarbonyl)-2,2-dimethyl-4H-[1,3]dioxino[4,5-c]pyridine-5-carboxylic acid (23a) (0.135 g, 0.505 mmol, 1 eq) and N,N-diisopropylethylamine (0.196 g, 1.515 mmol, 3 eq) in N,N-dimethylformamide (5.0 mL). Reaction was stirred 10 min. before 4-fluorobenzylamine (0.070 g, 0.556 mmol, 1.1 eq) was added. The reaction mixture was stirred at room temperature overnight. Water was added and reaction mixture was extracted with ethyl acetate. Organic phases were combined, dried over magnesium sulfate and concentrated. The crude product was purified by silica gel (50% ethyl acetate/hexane) to give 0.066 g of 48a (34%) as a white solid. MS-ESI m/z 375 [MH]+.

Step 48b: Preparation of Product 48

Lithium bis(trimethylsilyl)amide (0.870 mL of 1M solution in tetrahydrofuran, 0.870 mmol, 5 eq) at −78° C. was added to methoxylamine hydrochloride (0.017 g, 0.209 mmol, 1.2 eq) in tetrahydrofuran (3.0 mL). The reaction mixture was stirred 10 min. then a solution of 48a. 065 g, 0.174 mmol, 1 eq) in tetrahydrofuran (3.0 mL) was added. The reaction mixture was stirred at −78° C. 30 min. before a solution of saturated ammonium chloride was added. This reaction mixture was extracted with ethyl acetate and organic phases were combined and concentrated under reduced pressure to give 0.50 g of crude product 48 (74%) as a white solid. MS-ESI m/z 390 [MH]+.

Example 49

3-Hydroxy-4-hydroxymethyl-pyridine-2,5-dicarboxylic Acid 5-(4-fluoro-benzylamide)2-(methoxyamide)

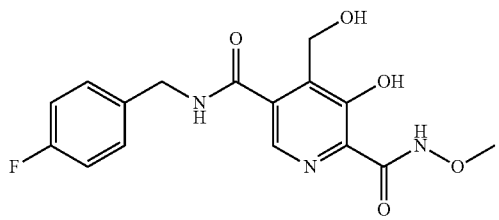 [SMILES: CONC(=O)c1ncc(C(=O)NCc2ccc(F)cc2)c(CO)c1O]

Formic acid (2 mL) was added to 48 (0.048 g, 0.123 mmol, 1 eq). The reaction mixture was stirred at room temperature 10 min. Formic acid was concentrated under vacuum and solid was triturated with diethyl ether under to give 0.030 g of 49 (71%) as a white solid. MS-ESI m/z 350 [MH]+.

Example 50

Preparation of 2,2-Dimethyl-4H-[1,3]dioxino[4,5-e]pyridine-5,8-dicarboxylic Acid 5-cyclohexylmethyl-amide 8-hydroxyamide (Product 50)

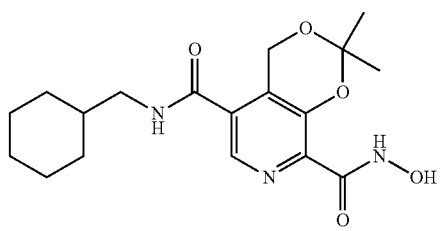 [SMILES: CC1(C)OCc2c(C(=O)NCC3CCCCC3)cnc(C(=O)NO)c2O1]

Step 50a: Preparation of xxx (Compound 50a)

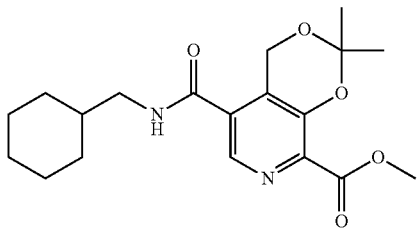 [SMILES: COC(=O)c1ncc(C(=O)NCC2CCCCC2)c2c1OC(C)(C)OC2]

To 8-(methoxycarbonyl)-2,2-dimethyl-4H-[1,3]dioxino[4,5-c]pyridine-5-carboxylic acid (23a) (0.100 g, 0.374 mmol, 1 eq) and N,N-diisopropylethylamine (0.145 g, 1.122 mmol, 3 eq) in N,N-dimethylformamide (5.0 mL) was added N,N,N',N''-Tetramethyl-O-(1H-benzotriazol-1-yl)uranium hexafluorophosphate (0.213 g, 0.758 mmol, 1.5 eq). Reaction was stirred 10 min. before cylohexanemethylamine (0.047 g, 0.412 mmol, 1.1 eq) was added. The reaction mixture was stirred at room temperature overnight. Water was added and reaction mixture was extracted with ethyl acetate. Organic phases were combined, dried over magnesium sulfate and concentrated. The crude product was purified by silica gel (60% ethyl acetate/hexane) to give 0.040 g of 50a (30%) as a white solid. MS-ESI m/z 363 [MH]+.

Step 50b: Preparation of Product 50

To 50a (0.140 g, 0.350 mmol, 1 eq) in tetrahydrofuran (5.0 mL) was added hydroxylamine solution 50 wt. % in water (5.0 mL). The reaction mixture was stirred at reflux 3 hrs. The pH was adjusted to 6 and reaction mixture was extracted with ethyl acetate. Organic phases were combined, dried over magnesium sulfate and concentrated under vacuum to give 0.025 g of 50 (63%) as a white solid. MS-ESI m/z 364 [MH]+.

Example 51

Preparation of 3-Hydroxy-4-hydroxymethyl-pyridine-2,5-dicarboxylic Acid 5-cyclohexylmethyl-amide 2-hydroxyamide (Product 51)

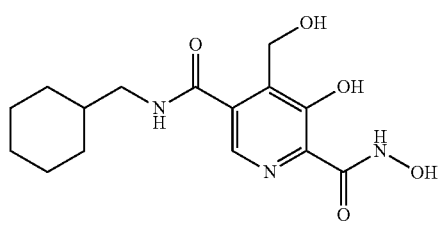 [SMILES: O=C(NCC1CCCCC1)c1cnc(C(=O)NO)c(O)c1CO]

To 50 (0.020 g, 0.055 mmol, 1 eq) was added formic acid (2.0 mL). The reaction mixture was stirred at room temperature 10 min. Formic acid was concentrated under vacuum and solid was triturated with diethyl ether under to give 0.015 g of 51 (88%) as a white solid. MS-ESI m/z 324 [MH]+.

Example 52

Preparation of 3-Hydroxy-4-hydroxymethyl-pyridine-2,5-dicarboxylic acid 5-cyclohexylmethyl-amide 2-hydroxyamide (Product 52)

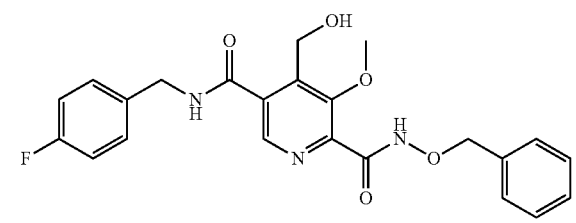 [SMILES: COc1c(C(=O)NOCc2ccccc2)ncc(C(=O)NCc2ccc(F)cc2)c1CO]

Step 52a: Preparation of Compound 52a

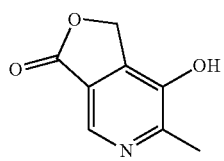

The starting material was obtained by the catalytic hydrogenation of XXIV (2.0 g) over Pd/C 5% in EtOAc. Filtration and evaporation gave 1.3 g white powder quantitative conversion.

Step 52b: Preparation of Compound 52b

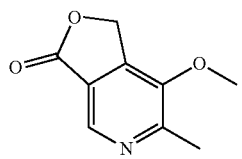

Trimethylsilyl-diazomethane (8.40 mL, 16.8 mmol, 3 eq) at 0° C. was added to 52a (0.924 g, 0.516 mmol, 1 eq) in methanol (10.0 mL) and tetrahydrofuran (10.0 mL). The reaction mixture was stirred at room temperature 20 min. A saturated sodium bicarbonate solution was added and reaction mixture was extracted with ethyl acetate. Organic phases were combined, dried over magnesium sulfate and concentrated under reduced pressure. The crude product was purified by silica gel (50% ethyl acetate/hexane) to give 0.600 g of 52b (60%) as a white solid. MS-ESI m/z 180

Step 52c: Preparation of Compound 52c

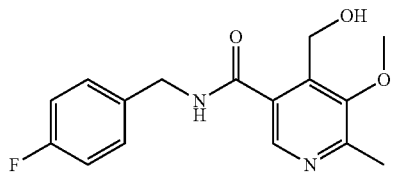 [SMILES: COc1c(C)ncc(C(=O)NCc2ccc(F)cc2)c1CO]

4-Fluorobenzylamine (0.440 g, 3.519 mmol, 2 eq) and 52b (0.315 g, 1.759 mmol, 1 eq) were heated neat at 80° C. for 30 min. The crude product was purified by silica gel (100% ethyl acetate) to give 0.350 g of 52c (%) as a white solid. MS-ESI m/z 305 [MH]+.

Step 52d: Preparation of Compound 52d

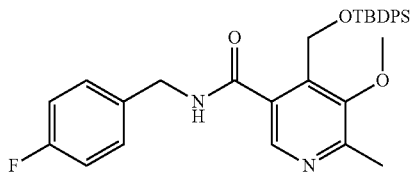

tert-Butyl(chloro)diphenylsilane (0.380 g, 1.382 mmol, 1.2 eq) was added to imidazole (0.235 g, 3.45 mmol, 3 eq) in dichloromethane (30.0 mL). The reaction mixture was stirred at room temperature 10 min. then a solution of 52c (0.350 g, 1.151 mmol, 1 eq) in dichloromethane (5.0 mL) was added. The reaction was stirred at room temperature 2 hrs. Water was added and reaction mixture was extracted with ethyl acetate. Organic phases were combined, dried over magnesium sulfate and concentrated under reduced pressure. The crude product was purified by silica gel (70% ethyl acetate/hexane) to give 0.387 g of 52d (62%) as a white solid. MS-ESI m/z 543 [MH]+.

Step 52e: Preparation of Compound 52e

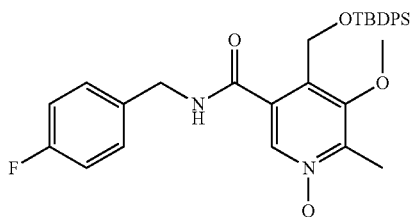

3-chloroperbenzoic acid (0.222 g, 1.285 mmol, 1.8 eq) at room temperature was added to 52d (0.387 g, 0.714 mmol, 1 eq) in dichloromethane (30.0 mL) was added. The reaction mixture was stirred 1 hour at room temperature. A 1M solution of potassium carbonate was added and reaction mixture was extracted with dichloromethane. Organic phases were combined, dried over magnesium sulfate and concentrated to give 0.398 g of 52e (100%) as a white solid. MS-ESI m/z 559 [MH]+.

Step 52f: Preparation of Compound 52f

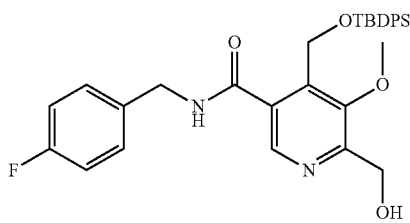

Trifluoroacetic anhydride (0.450 g, 2.142 mmol, 3 eq) at room temperature was added to 52e (0.398 g, 0.714 mmol, 1 eq) in dichloromethane (30.0 mL). The reaction mixture was stirred overnight at room temperature. A 1M solution of potassium carbonate was added and reaction mixture was extracted with ethyl acetate. Organic phases were combined, dried over magnesium sulfate and concentrated. The crude product was purified by silica gel (60% ethyl acetate) to give 0.209 g of 52f (53%) as a white solid. MS-ESI m/z 559 [MH]+.

Step 52g: Preparation of Compound 52g

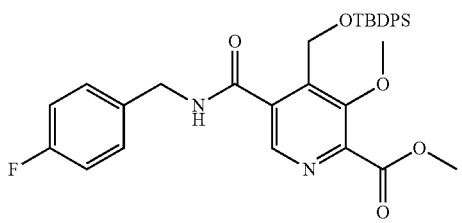

Activated manganese oxide (0.164 g, 1.88 mmol, 5 eq) at room temperature was added to 52f (0.210 g, 0.376 mmol, 1 eq) in chloroform (30.0 mL). The reaction mixture was stirred at reflux 5 hr. Solvent was concentrated under vacuo and crude reaction mixture was dissolved in methanol (20.0 mL). A solution of sodium cyanide (0.022 g, 0.451 mmol, 1.2 eq) in methanol (3.0 mL) was added and the reaction mixture was stirred 1 hr at room temperature. The reaction mixture was filtered on Celite. Organic phase was washed with water and extracted with ethyl acetate. The crude product was purified by silica gel (30% ethyl acetate/hexane) to give 0.130 g of 52g (59%) as a white solid. MS-ESI m/z 587 [MH]+.

Step 52h: Preparation of Compound 52h

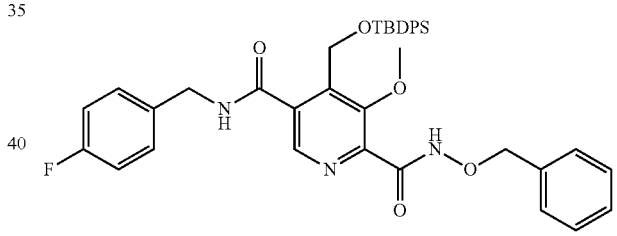

Lithium bis(trimethylsilyl)amide (1.2 mL of a 1M solution in tetrahydrofuran, 1.135 mmol, 5 eq) at −78° C. was added to benzylhydroxylamine hydrochloride (0.041 g, 0.249 mmol, 1.1 eq) in tetrahydrofuran (20.0 mL). The reaction mixture was stirred 10 min. then a solution of 52g (0.133 g, 0.227 mmol, 1 eq) in tetrahydrofuran (3.0 mL) was added. The reaction mixture was stirred at −78° C. 30 min. before a solution of saturated ammonium chloride was added. This reaction mixture was extracted with ethyl acetate and organic phases were combined and concentrated under reduced pressure to give 0.140 g of crude product 52h (100%) as a white solid. MS-ESI m/z 678 [MH]+.

Step 52i: Preparation of Product 52

A tetrabutylammonium fluoride solution (0.620 mL of a solution 1M in tetrahydrofuran, 0.620 mmol, 3 eq) was added to a solution of 52h (0.140 g, 0.207 mmol, 1 eq) in tetrahydrofuran (10.0 mL) was added. The reaction mixture was stirred at room temperature 1 hr. and concentrated under vacuo. The crude product was purified by silica gel (70% ethyl acetate/hexane) to give 0.062 g of 52 (62%) as a white solid. MS-ESI m/z 440 [MH]+.

Example 53

Preparation of 4-Hydroxymethyl-3-methoxy-pyridine-2,5-dicarboxylic Acid 5-(4-fluoro-benzylamide) 2-hydroxyamide (Product 53)

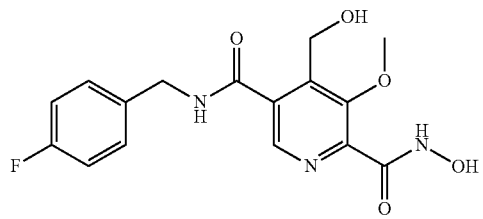 [SMILES: COc1c(C(=O)NO)ncc(C(=O)NCc2ccc(F)cc2)c1CO]

Compound 52 (0.060 g, 0.137 mmol, 1 eq) and 10% Pd/C (5 mg) in methanol (4.0 mL) were stirred under an atmosphere of hydrogen 1 hour. The catalyst was filtered and reaction mixture was concentrated under vacuum to give 0.040 g of 53 (85%) as a white solid. MS-ESI m/z 350 [MH]+.

Example 54

Preparation of 3-Hydroxy-4-hydroxymethyl-pyridine-2,5-dicarboxylic Acid 5-(4-fluoro-benzylamide) 2-(hydroxy-methyl-amide) (Product 54)

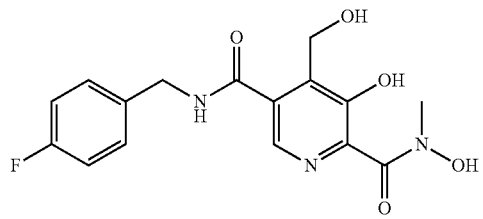 [SMILES: CN(O)C(=O)c1ncc(C(=O)NCc2ccc(F)cc2)c(CO)c1O]

Product 54 was prepared using the procedure described in example 2 and using methoxylamine. MS-ESI m/z 350 [MH]+.
MS-ESI m/z 350 [MH]+.

Example 55

Preparation of 3-Hydroxy-4-hydroxymethyl-pyridine-2,5-dicarboxylic Acid 5-dibenzylamide 2-hydroxyamide (Product 55)

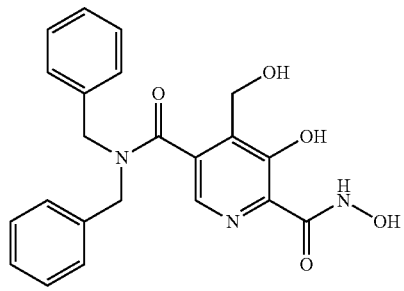 [SMILES: O=C(NO)c1ncc(C(=O)N(Cc2ccccc2)Cc2ccccc2)c(CO)c1O]

Compound 55 was synthesized in a manner similar to example 2 using dibenzylamine. MS-ESI m/z 408 [MH]+.

Example 56

5-{[1-(4-Fluoro-phenyl)-cyclopropylamino]-methyl}-3-hydroxy-4-hydroxymethyl-pyridine-2-carboxylic Acid Hydroxyamide (Product 56)

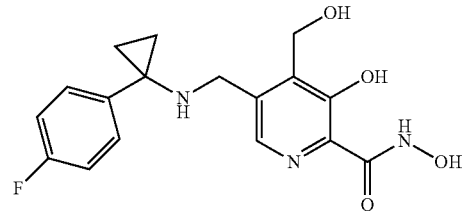 [SMILES: O=C(NO)c1ncc(CNC2(c3ccc(F)cc3)CC2)c(CO)c1O]

Product 56 was synthesized in a manner analogous to that in example 9 using 1-4-Fluoro-phenyl)-cyclopropylamine. MS-ESI m/z 354 [MH]+.

Example 57

Preparation of 5-{[(1-(4-Fluoro-phenyl)-cyclopropylamino]-methyl}-2,2-dimethyl-4H-[1,3]dioxino[4,5-c]pyridine-8-carboxylic Acid Hydroxyamide (Product 57)

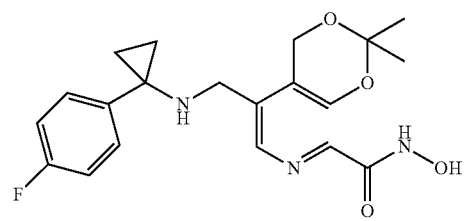 [SMILES: CC1(C)OC=C(/C(=C\N=C\C(=O)NO)CNC2(c3ccc(F)cc3)CC2)CO1]

Product 57 was synthesized in a manner analogous to that in example 48 using 1-4-Fluoro-phenyl)-cyclopropylamine. MS-ESI m/z 354 [MH]+.

Example 58

Preparation of 5-(4-Fluoro-benzyloxymethyl)-3-hydroxy-4-hydroxymethyl-pyridine-2-carboxylic Acid Methoxy-amide

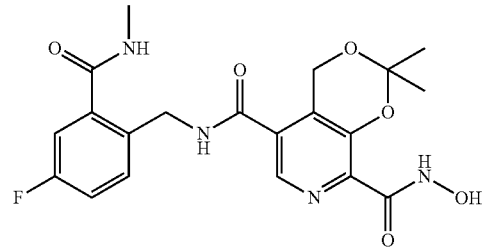 [SMILES: CNC(=O)c1cc(F)ccc1CNC(=O)c1cnc(C(=O)NO)c2c1COC(C)(C)O2]

Product 58 was synthesized in a manner similar to that in example 20 using 4-fluorobenzyl chloride and methoxylamine.
MS-ESI m/z 337 [MH]+.

Example 59

Preparation of 2,2-Dimethyl-4H-[1,3]dioxino[4,5-c]pyridine-5,8-dicarboxylic Acid 5-(4-fluoro-2-methylcarbamoyl-benzylamide) 8-hydroxyamide (Product 59)

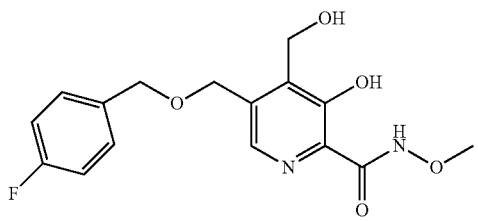 [SMILES: CONC(=O)c1ncc(COCc2ccc(F)cc2)c(CO)c1O]

Product 59 was synthesized in a manner similar to example 48 using 4-fluoro-2-methylcarbamoyl-benzylamine.

MS-ESI m/z 433 [MH]⁺.

Example 60

Preparation of 3-Hydroxy-4-hydroxymethyl-pyridine-2,5-dicarboxylic Acid 2-hydroxyamide 5-(4-methyl-benzylamide) (Product 60)

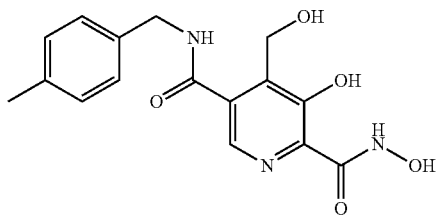 [SMILES: Cc1ccc(CNC(=O)c2cnc(C(=O)NO)c(O)c2CO)cc1]

Product 60 was synthesized in a manner similar to example 2 using 4-methyl-benzylamine.

MS-ESI m/z 332 [MH]⁺.

Example 61

Preparation of 3-Hydroxy-4-hydroxymethyl-pyridine-2,5-dicarboxylic Acid 5-{[2-(4-fluoro-phenyl)-ethyl]-amide}2-hydroxyamide (Product 61)

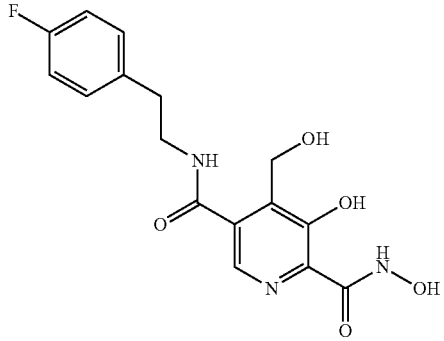 [SMILES: O=C(NCCc1ccc(F)cc1)c1cnc(C(=O)NO)c(O)c1CO]

Product 61 was synthesized in a manner similar to example 2 using 2-(4-fluoro-phenyl)-ethylamine MS-ESI m/z 350 [MH]⁺.

Example 62

Preparation of 3-Hydroxy-4-hydroxymethyl-pyridine-2,5-dicarboxylic Acid 5-(2,4-difluoro-benzylamide) 2-hydroxyamide (Product 62)

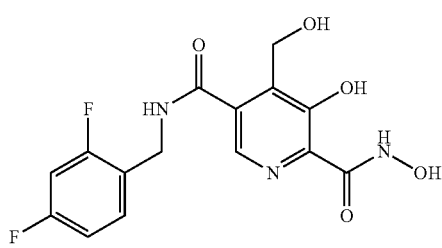 [SMILES: O=C(NCc1ccc(F)cc1F)c1cnc(C(=O)NO)c(O)c1CO]

Product 62 was synthesized in a manner similar to example 2 using 2,4-difluoro-benzylamine MS-ESI m/z 354 [MH]⁺.

Example 63

Preparation of (rac)-{2-(4-Chloro-phenyl)-1-[(4-fluoro-benzyl)-(5-hydroxy-6-hydroxycarbamoyl-4-hydroxymethyl-pyridin-3-ylmethyl)-carbamoyl]-ethyl}-carbamic Acid Methyl Ester (Product 63)

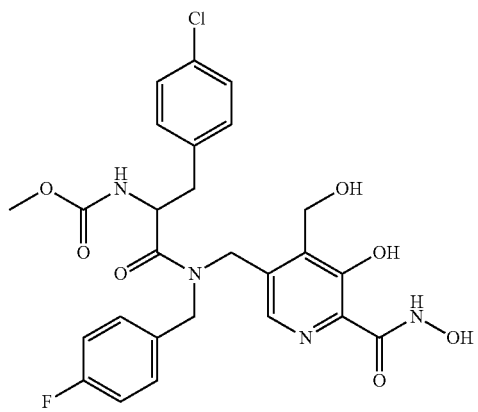 [SMILES: COC(=O)NC(Cc1ccc(Cl)cc1)C(=O)N(Cc1ccc(F)cc1)Cc1cnc(C(=O)NO)c(O)c1CO]

Product 63 was obtained from the reaction of 3-(4-Chlorophenyl)-2-methoxycarbonylamino-propionic acid chloride and compound obtained from example 9 step 9a, followed by catalytic hydrogenation Over Pd/C 5% in ethyl acetate. MS-ESI m/z 561 [MH]+.

Example 64

Preparation of (Rac) 5-{[(4-Fluoro-benzyl)-(2-phenyl-cyclopropanecarbonyl)-amino]-methyl}-3-hydroxy-4-hydroxymethyl-pyridine-2-carboxylic Acid Hydroxyamide (Compound 64)

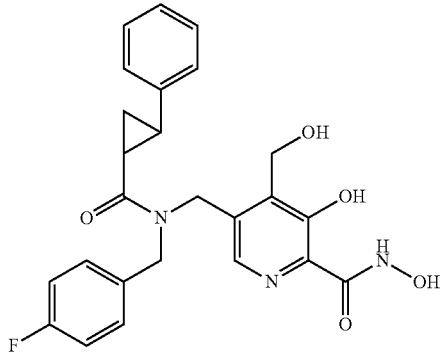 [SMILES: O=C(NO)c1ncc(CN(Cc2ccc(F)cc2)C(=O)C2CC2c2ccccc2)c(CO)c1O]

Product 64 was obtained from the reaction of 2-phenyl-cyclopropanecarbonyl chloride and compound obtained from example 9, step 9a, followed by catalytic hydrogenation over Pd/C 5% in ethyl acetate. MS-ESI m/z 466 [MH]+.

Example 65

Preparation of (4-Fluoro-benzyl)-(5-hydroxy-6-hydroxycarbamoyl-4-hydroxymethyl-pyridin-3-ylmethyl)-carbamic Acid Methyl Ester (Product 65)

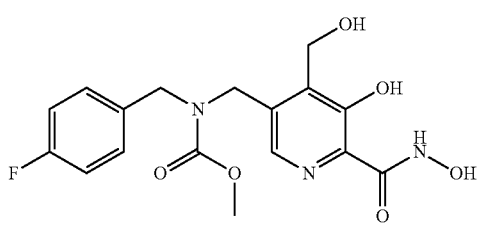 [SMILES: COC(=O)N(Cc1ccc(F)cc1)Cc1cnc(C(=O)NO)c(O)c1CO]

Product 65 was obtained from the reaction of methyl chloroformate and compound obtained from example 9a, followed by catalytic hydrogenation over Pd/C 5% in ethyl acetate. MS-ESI m/z 380 [MH]+.

Example 66

Preparation of (3-Chloro-4-fluoro-benzyl)-(5-hydroxy-6-hydroxycarbamoyl-4-hydroxymethyl-pyridin-3-ylmethyl)-carbamic Acid Benzyl Ester (Product 66)

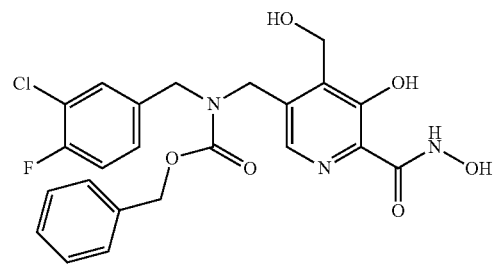 [SMILES: O=C(NO)c1ncc(CN(Cc2ccc(F)c(Cl)c2)C(=O)OCc2ccccc2)c(CO)c1O]

Product 66 was obtained in a similar manner as that of example 65, using 4-fluoro-3-Chlorobenzyl amine in the initial step and benzyl chloroformate as the acylating agent. MS-ESI m/z 490 [MH]+.

Example 67

Preparation of 5-[2-(4-Fluoro-phenyl)-ethyl]-3-hydroxy-4-hydroxymethyl-pyridine-2-carboxylic Acid Hydroxyamide ((Product 67)

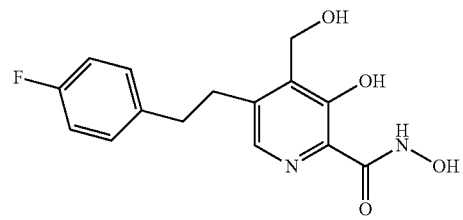 [SMILES: O=C(NO)c1ncc(CCc2ccc(F)cc2)c(CO)c1O]

Product 67 was synthesized by reaction of 5-formyl (0.751 g, 3 mmol) an 1000 mg (3.5 mmol) (4-fluorobenzyl) triphenyphosphonium bromide in THF at −78*C then stirred overnight at R.T. The reaction was quenched with NH4Cl (sat). The crude product was separated on silica gel to yield 417 mg (31%). This product was hydrogenated by catalytic hydrogenation over Pd/C 5% in EtOAc. Silica gel chromatography purification yielded 305 mg, which was reacted with hydroxylamine (excess) in ethanol (2 h, 80*C). The compound was precipitated HCl 1N, filtered and redissolved in MeOH with the addition of 6N HCl, stirred for 4 hr, followed by evaporation; providing the desired product. MS-ESI m/z 307 [MH]+.

Example 68

Preparation of 3-Hydroxy-4-hydroxymethyl-5-(3-phenyl-propyl)-pyridine-2-carboxylic Acid Hydroxyamide ((Product 68)

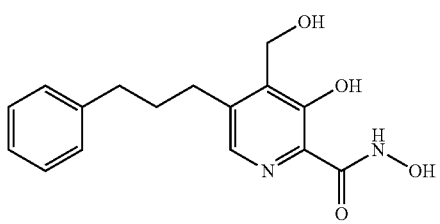 [SMILES: O=C(NO)c1ncc(CCCc2ccccc2)c(CO)c1O]

Product 68 was synthesized in a manner similar to example 68 using (phenylacetylene lithium salt in the initial step. Catalytic hydrogenation (Pd/C 5% in EtOAc) was done in the presence of 3 eq of acetic anhydride, 1 atm 24 h. The subsequent steps were as per example 68. MS-ESI m/z 303 [MH]+.

Example 69

Preparation of 5-Benzenesulfonylmethyl-3-hydroxy-4-hydroxymethyl-pyridine-2-carboxylic Acid Hydroxyamide ((Product 69)

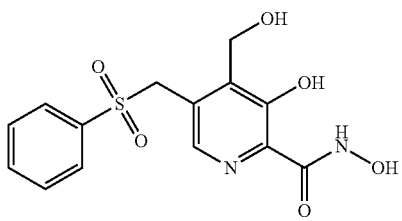 [SMILES: O=C(NO)c1ncc(CS(=O)(=O)c2ccccc2)c(CO)c1O]

550 mg of Compound XI, of scheme 3, was dissolved in 30 mL DCM was reacted with 2.5 eq of methane sulfonyl chloride in the presence of 5 eq triethyl amine. Extraction vs 5% citric acid, drying over Na$_2$SO$_4$, and evaporation yielded 500 mg of desired mesylate. This mesylate was immediately reacted with 400 mg of benzene sulfinic acid in DMF 2 mL. the product was isolated by precipitation in water and filtration. The crude was dissolved in CHCl3 30 mL and 400 mg mCPBA (70%) was added. After 1 h stirring, the reaction was extracted using K$_2$CO$_3$ and the organic phase dried over CaCO$_3$ the evaporated. The residue was dissolved in 3 mL DCM and 3 mL trifluoroactetic anhydride was added. Stirring at reflux 45*C for 20 h affording the rearranged product, isolated through evaporation of solvent. The residue was then added to a solution of MnO2 2 g in CHCl3 (30 ml) and stirred at reflux 1 h. filtration and evaporation afforded the aldehyde (250 mg) This was placed in 10 mL meOH with 1.2 eq I2 and 3 eq KOTMS. Stirring at R.T. for 1 h gave the ester in quantitative conversion. The product was purified on Silica gel. 100 mg of the ester was reacted with excess (hydroxylamine 50% aq) in pyridine to give the hydroxamate. Dilution in EtOAc and extraction vs 5% citric acid gave the desired intermediate. The final product was obtained by adding 50 mg of the above acetonide to neat 70% formic acid. After 15 min the reaction is complete, the formic acid is evaporated off and the residue triturated with water to give 69 as a white powder. MS-ESI m/z 339 [MH]+.

Example 70

Preparation of 5-(4-Fluoro-phenylmethanesulfonyl-methyl)-2,2-dimethyl-4H-[1,3]dioxino[4,5-c]pyridine-8-carboxylic Acid Hydroxyamide (Product 70)

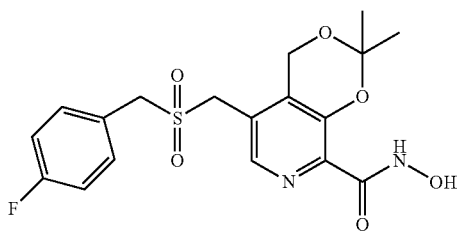 [SMILES: CC1(C)OCc2c(CS(=O)(=O)Cc3ccc(F)cc3)cnc(C(=O)NO)c2O1]

550 mg of Compound XI, of scheme 3, was dissolved in 30 mL DCM was reacted with 2.5 eq of methane sulfonyl chloride in the presence of 5 eq triethyl amine. Extraction vs 5% citric acid, drying over Na$_2$SO$_4$, and evaporation yielded 500 mg of desired mesylate. This was immediately reacted with 400 mg of 4 fluoro benzyl mercaptan in DMF 2 mL. the product was isolated by precipitation in water and filtration. The crude (0.5 g) was dissolved in CHCl$_3$ 30 mL and 1000 mg mCPBA (70%) was added. After 0.5 h stirring, the reaction was extracted using K2CO3 and the organic phase dried over CaCO3 the evaporated. The residue was dissolved in 3 mL DCM and 3 mL trifluoroactetic anhydride was added. Stirring at reflux 45*C for 20 h affording the rearranged product, isolated through evaporation of solvent. The residue was then added to a solution of MnO$_2$ 2 g in CHCl3 (30 ml) and stirred at reflux 1 h. filtration and evaporation afforded the aldehyde (300 mg). This was placed in 10 mL meOH with 1.2 eq NaCN and 0.5 g MnO$_2$. Stirring at R.T. for 1 h gave the ester in quantitative conversion. The product was purified on Silica gel. 98 mg of the ester was reacted with excess (hydroxylamine 50% aq) in pyridine to give the hydroxamate. Dilution in EtOAc and extraction vs 5% citric acid gave the desired compound 70. MS-ESI m/z 411 [MH]+.

Example 71

Preparation of 5-(4-Fluoro-phenylmethanesulfonyl-methyl)-3-hydroxy-4-hydroxymethyl-pyridine-2-carboxylic Acid Hydroxyamide (Product 71)

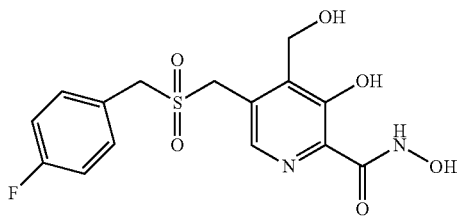 [SMILES: O=C(NO)c1ncc(CS(=O)(=O)Cc2ccc(F)cc2)c(CO)c1O]

Product 71 was obtained by adding 50 mg of compound from example 70 to neat 70% formic acid. After 15 min the

Example 72

Preparation of (4-Fluoro-benzyl)-(5-hydroxy-6-hydroxycarbamoyl-4-methyl-pyridin-3-ylmethyl)-carbamic Acid Benzyl Ester (Product 72)

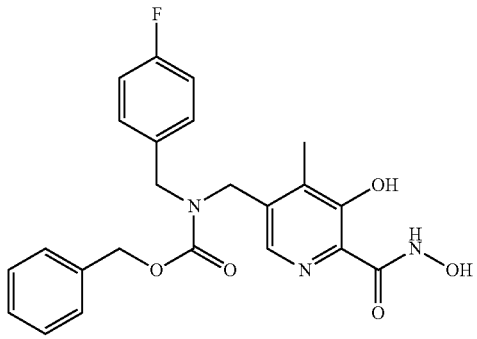 [SMILES: Cc1c(CN(Cc2ccc(F)cc2)C(=O)OCc2ccccc2)cnc(C(=O)NO)c1O]

Step 72a: Preparation of Compound 72a

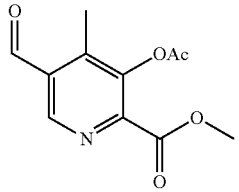 [SMILES: COC(=O)c1ncc(C=O)c(C)c1OC(C)=O]

The product from example 20e of methyl 5-((4-methoxybenzyloxy)methyl)-2,2-dimethyl-4H-[1,3]dioxino[4,5-c]pyridine-8-carboxylate (3.1 g, 8.3 mmol) was dissolved in 70% formic acid and left at RT 1 h. Evaporation of the acid gave a crude off-white powder (2.77 g, 100%). 1.95 g (5.9 mmol) was reacted in 30 ml DCM with 1.7 ml Acetic anhydride, 2.5 ml TEA and 36 mg DMAP for 3 h. Evaporation and Silica gel chromatography (EtOAc) of the crude gave 2.44 g (94%). 2.3 g was dissolved in 30 mL THF containing 450 mg 10% Pd/C and $H_2$ bubbled through for 3 h. Filtration and evaporation of the solvent yielded a residue used without further purification. This residue was dissolved in DCM (20 ml) and 5 mL of trifluoroacetic acid was added with a few drops of tripropylsilane. Evaporation yielded a crude product used without further purification. The crude product (1.31 g 5.5 mmol)was dissolved in 25 mL EtOAc and 1.85 g IBX added. The mixture was refluxed 3 h, cooled, filtered washed with EtOAc and the solvents removed. Purification by silica gel chromatography (EtOAc) gave 0.96 g (72%) of the desired product.

reaction is complete, the formic acid is evaporated off and the residue triturated with water to give 71 as a white powder. MS-ESI m/z 371 [MH]$^+$.

Step 72b: Preparation of 5-[(4-Fluoro-benzylamino)-methyl]-3-hydroxy-4-methyl-pyridine-2-carboxylic Acid Methyl Ester (Compound 72b)

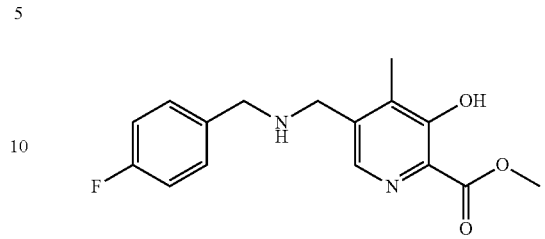

65 mg of the aldehyde 72a was dissolved in MeOH and 50 mg 4-Fluorobenzyl amine was added followed by 20 mg NaCNBH3. The mixture was stirred 2 h and concentrated. The residue was purified by silica gel (EtOAc) to give 87 mg product. This was reacted with 1.25 eq of benzylchloroformate, 2 eq TEA in DCM to yield the desired carbamate. Extraction vs 5% citric acid and evaporation of the organic phase yielded the crude product. The crude (17 mg) was the dissolved in 2 ml THF and 1 mL (50% hydroxylamine aq) was added, heated for 1 h at 60*C. The solvent was then evaporated and addition of 1 ml 10% citric acid gave a precipitate which was filtered and washed with water. Yield 11 mg 70%. MS-ESI m/z 440 [MH]$^+$.

Example 73

(4-Fluoro-benzyl)-(5-hydroxy-6-hydroxycarbamoyl-4-methyl-pyridin-3-ylmethyl)-carbamic Acid Tert-butyl Ester (Product 73)

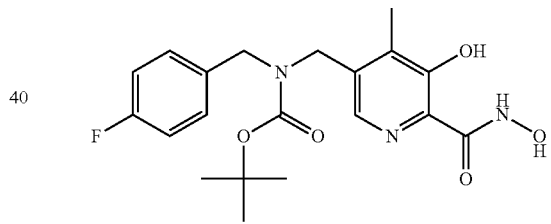

Product 73 was synthesized using a similar procedure as example 72 where di tert-butylpyrocarbonate replaces the benzylchloroformate. MS-ESI m/z 406 [MH]$^+$.

Example 74

Preparation of 3-Hydroxy-4-methyl-pyridine-2,5-dicarboxylic Acid 5-(3-chloro-4-fluoro-benzylamide) 2-hydroxyamide

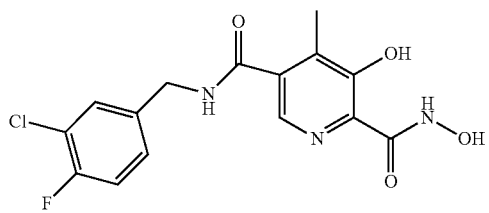 [SMILES: Cc1c(C(=O)NCc2ccc(F)c(Cl)c2)cnc(C(=O)NO)c1O]

Step 74a: Preparation of Compound 74a

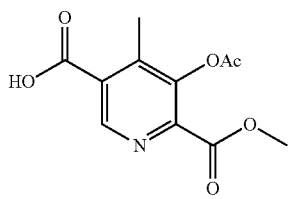 [SMILES: COC(=O)c1ncc(C(=O)O)c(C)c1OC(C)=O]

The compound from example 72 step a (608 mg, 2.6 mmol) was dissolved in acetone (15 ml). 2-methylbutene (2.0M in THF) 12 mL was added followed by a solution of 1.85 g Sodium Chlorite ($NaClO_2$) and 2.83 g $NaH_2PO_4$ in 15 mL $H_2O$. After 20 min at RT the solution was concentrated to remove the organic solvent and the pH adjusted to ~4 with Citric acid. The resulting white precipitate was filtered and washed with water. Drying gave 424 mg of desired product.

Step 74b: Preparation of Compound 74b 60 mg of the above acid was reacted with 30 mg (3-chloro-4-fluorobenzyl amine) 75 mg HBTU and 100 mg N-methylmorpholine in 2 mL DMF. After 1 h the solution was diluted in EtOAc and extracted vs 5% citric acid. The organic phase was evaporated to afford the crude product. This was dissolved in 1 mL pyridine and 0.5 mL 50% hydroxylamine in water was added. After 1 h at 45*C the pyridine/water azeotrope was removed under vacuum and the residue triturated with 10% citric acid. The precipitate was filtered and washed to give the desired product. MS-ESI m/z 354 $[MH]^+$.

Example 75

Preparation of 5-(4-Fluoro-benzyloxymethyl)-3-hydroxy-4-hydroxymethyl-pyridine-2-carboxylic Acid Methoxy-amide (Product 75)

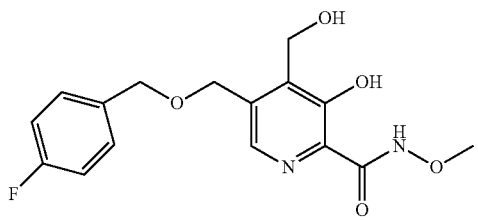 [SMILES: CONC(=O)c1ncc(COCc2ccc(F)cc2)c(CO)c1O]

Product 75 was prepared in a procedure analogous to that shown in example 20 with the exception of the use of 4-fluoro-benzyl chloride as alkylating agent, and the use of methoxyl amine instead of hydroxylamine.

LC-MS $(M+H)^+$ m/z 337.

TABLE 3

Listing of Compounds in Examples

| Example, step | Chemical Name |
|---|---|
| 1 | $N^2$,3-bis(benzyloxy)-$N^5$-(4-fluorobenzyl)-4-(hydroxymethyl)pyridine-2,5-dicarboxamide |
| 1, step 1a | N,9-bis(benzyloxy)-3,3-dimethyl-1,5-dihydro-[1,3]dioxepino[5,6-c]pyridine-8-carboxamide |
| 1, step 1b | N,3-bis(benzyloxy)-4,5-bis(hydroxymethyl) picolinamide |
| 1, step 1c | N,7-bis(benzyloxy)-3-oxo-1,3-dihydrofuro[3,4-c]pyridine-6-carboxamide |
| 1, step 1d | $N^2$,3-bis(benzyloxy)-$N^5$-(4-fluorobenzyl)-4-(hydroxymethyl)pyridine-2,5-dicarboxamide |
| 2 | $N^5$-(4-fluorobenzyl)-$N^2$,3-dihydroxy-4-(hydroxymethyl)pyridine-2,5-dicarboxamide |
| 3 | $N^5$-(benzo[d][1,3]dioxol-5-ylmethyl)-N2,3-bis(benzyloxy)-4-(hydroxymethyl)pyridine-2,5-dicarboxamide |
| 4 | $N^5$-(benzo[d][1,3]dioxol-5-ylmethyl)-N2,3-dihydroxy-4-(hydroxymethyl)pyridine-2,5-dicarboxamide |
| 5 | $N^2$,3-bis(benzyloxy)-4-(hydroxymethyl)-$N^5$-(4-methoxybenzyl)pyridine-2,5-dicarboxamide |
| 6 | $N^2$,3-dihydroxy-4-(hydroxymethyl)-$N^5$-(4-methoxybenzyl)pyridine-2,5-dicarboxamide |
| 7 | $N^2$,3-bis(benzyloxy)-$N^3$-(3,5-difluorobenzyl)-4-(hydroxymethyl)pyridine-2,5-dicarboxamide |
| 8 | $N^5$-(3,5-difluorobenzyl)-$N^2$,3-dihydroxy-4-(hydroxymethyl)pyridine-2,5-dicarboxamide |
| 9 | 5-((4-fluorobenzylamino)methyl)-N,3-dihydroxy-4-(methoxymethyl)picolinamide) |
| 9, step 9a | N,3-bis(benzyloxy)-5-((4-fluorobenzylamino)methyl)-4-(hydroxymethyl)picolinamide (compound 9a) |
| 10 | 5-((3,5-difluorobenzylamino)methyl)-N,3-dihydroxy-4-(hydroxymethyl)picolinamide |
| 10, step 10a | 5-((3,5-difluorobenzylamino)methyl)-N,3-dihydroxy-4-(hydroxymethyl) picolinamide |
| 11 | 5-((benzo[d][1,3]dioxol-5-ylmethylamino)methyl)-N,3-dihydroxy-4-(hydroxymethyl)picolinamide |
| 1, step 11a | 5-((benzo[d][1,3]dioxol-5-ylmethylamino)methyl)-N,3-bis(benzyloxy)-4-(hydroxymethyl)picolinamide |
| 12 | N5-(4-fluorobenzyl)-$N^2$,3-dihydroxy-4-(methoxymethyl)-$N^5$-methylpyridine-2,5-dicarboxamide |
| 12, step 12a | 5-(benzyloxy)-N-(4-fluorobenzyl)-4-(hydroxymethyl)-6-methylnicotinamide |
| 12, step 12b | 5-(benzyloxy)-N-(4-fluorobenzyl)-4-(methoxymethyl)-N,6-dimethylnicotinamide |
| 12, step 12c | 3-(benzyloxy)-5-((4-fluorobenzyl)(methyl)carbamoyl)-4-(methoxymethyl)-2-methylpyridine 1-oxide |
| 12, step 12d | 5-(benzyloxy)-N-(4-fluorobenzyl)-6-(hydroxymethyl)-4-(methoxymethyl)-N-methylnicotinamide |
| 12, step 12e | 5-(benzyloxy)-N-(4-fluorobenzyl)-6-formyl-4-(methoxymethyl)-N-methylnicotinamide |
| 12, step 12f | methyl 3-(benzyloxy)-5-((4-fluorobenzyl)(methyl) carbamoyl)-4-(methoxymethyl)picolinate |
| 12, step 12g | $N^2$,3-bis(benzyloxy)-$N^5$-(4-fluorobenzyl)-4-(methoxymethyl)-$N^5$-methylpyridine-2,5-dicarboxamide |
| 12, step 12h | $N^5$-(4-fluorobenzyl)-N2,3-dihydroxy-4-(methoxymethyl)-N5-methylpyridine-2,5-dicarboxamide |
| 13 | $N^2$,3-bis(benzyloxy)-$N^5$-(3-chloro-4-fluorobenzyl)-4-(hydroxymethyl)pyridine-2,5-dicarboxamide |
| 14 | $N^5$-(3-chloro-4-fluorobenzyl)-N2,3-dihydroxy-4-(hydroxymethyl)pyridine-2,5-dicarboxamide |
| 15 | $N^2$,3-bis(benzyloxy)-$N^5$-(3,4-dichlorobenzyl)-4-(hydroxymethyl)pyridine-2,5-dicarboxamide |
| 16 | $N^5$-(3,4-dichlorobenzyl)-$N^2$,3-dihydroxy-4-(hydroxymethyl)pyridine-2,5-dicarboxamide |
| 17 | N,3-Dihydroxy-4-(hydroxymethyl)-5-((4-methoxybenzyloxy)methyl)-picolinamide |
| 17, step 17a | 5-((4-Methoxybenzyloxy)methyl)-2,2,8-trimethyl-4H-[1,3]dioxino[4,5-c]pyridine |
| 17, step 17b | 5-((4-Methoxybenzyloxy)methyl)-2,2,8-trimethyl-4H-[1,3]dioxino[4,5-c]pyridine 7-oxide |
| 17, step 17c | (5-((4-Methoxybenzyloxy)methyl)-2,2-dimethyl-4H-[1,3]dioxino[4,5-c]pyridin-8-yl)methanol |
| 17, step 17d | 5-((4-Methoxybenzyloxy)methyl)-2,2-dimethyl-4H-[1,3]dioxino[4,5-c]pyridine-8-carbaldehyde |
| 17, step 17e | ethyl 5-((4-methoxybenzyloxy)methyl)-2,2-dimethyl-4H-[1,3]dioxino[4,5-c]pyridine-8-carboxylate |
| 17, step 17f | ethyl 3-hydroxy-4-(hydroxymethyl)-5-((4-methoxybenzyloxy)methyl)picolinate |
| 17, step 17g | N,3-Dihydroxy-4-(hydroxymethyl)-5-((4-methoxybenzyloxy)methyl)picolinamide |
| 18 | 5-(Benzyloxymethyl)-N,3-dihydroxy-4-(hydroxymethyl)picolinamide |

TABLE 3-continued

Listing of Compounds in Examples

| Example, step | Chemical Name |
|---|---|
| 19 | N-hydroxy-5-((4-methoxybenzyloxy)methyl)-2,2-dimethyl-4H-[1,3]dioxino[4,5-c]pyridine-8-carboxamide |
| 19, step 19a | 5-((4-Methoxybenzyloxy)methyl)-2,2-dimethyl-4H-[1,3]dioxino[4,5-c]pyridine-8-carboxylic acid |
| 19, step 19b | N-(Benzyloxy)-5-((4-methoxybenzyloxy)methyl)-2,2-dimethyl-4H-[1,3]dioxino[4,5-c]pyridine-8-carboxamide |
| 19, step 19c | N-(Benzyloxy)-3-hydroxy-4-(hydroxymethyl)-5-((4-methoxybenzyloxy)methyl) picolinamide |
| 19, step 19d | N-hydroxy-5-((4-methoxybenzyloxy)methyl)-2,2-dimethyl-4H-[1,3]dioxino[4,5-c]pyridine-8-carboxamide |
| 20 | $N^5$-(3,4-difluorobenzyl)-$N^2$,3-dihydroxy-4-(hydroxymethyl)pyridine-2,5-dicarboxamide |
| 21 | 5-[(4-Fluoro-phenylamino)-methyl]-3-hydroxy-4-hydroxymethyl-pyridine-2-carboxylic acid hydroxyamide |
| 21 step a | methyl 5-((4-fluorophenylamino)methyl)-2,2-dimethyl-4H-[1,3]dioxino[4,5-c]pyridine-8-carboxylate |
| 21 step b | 5-((4-fluorophenylamino)methyl)-3-hydroxy-4-(hydroxymethyl) picolinate |
| 22 | 5-{[2-(4-Fluoro-phenyl)-ethylamino]-methyl}-3-hydroxy-4-hydroxymethyl-pyridine-2-carboxylic acid hydroxyamide |
| 22 Step22b | Methyl 5-((4-fluorophenethylamino)methyl)-3-hydroxy-4-(hydroxymethyl)picolinate |
| 23 | 5-(4-Fluoro-benzoylamino)-3-hydroxy-4-hydroxymethyl-pyridine-2-carboxylic acid hydroxyamide |
| 23 Step 23a | 8-(methoxycarbonyl)-2,2-dimethyl-4H-[1,3]dioxino[4,5-c]pyridine-5-carboxylic acid |
| 23 Step 23b | Methyl 5-(benzyloxycarbonylamino)-2,2-dimethyl-4H-[1,3]dioxino[4,5-c]pyridine-8-carboxylate |
| 23 Step 23c | 5-Amino-2,2-dimethyl-4H-[1,3]dioxino[4,5-c]pyridine-8-carboxylic acid methyl ester |
| 23 Step 23d | Methyl 5-(4-fluorobenzamido)-2,2-dimethyl-4H-[1,3]dioxino[4,5-c]pyridine-8-carboxylate |
| 23 Step 23e | Methyl 5-(4-fluorobenzamido)-3-hydroxy-4-(hydroxymethyl)picolinate |
| 24 | (8-Hydroxycarbamoyl-2,2-dimethyl-4H-[1,3]dioxino[4,5-c]pyridin-5-yl)-carbamic acid benzyl ester |
| 25 | 5-{[Benzyl-(4-fluoro-phenyl)-amino]-methyl}-3-hydroxy-4-hydroxymethyl-pyridine-2-carboxylic acid hydroxyamide |
| 25 Step 25a | Methyl 5-((benzyl(4-fluorophenyl)amino)methyl)-2,2-dimethyl-4H-[1,3]dioxino[4,5-c]pyridine-8-carboxylate |
| 26 | 5-({2-Benzyloxy-ethyl)-[2-(4-fluoro-phenyl)-ethyl]-amino}-methyl)-3-hydroxy-4-hydroxymethyl-pyridine-2-carboxylic acid hydroxyamide |
| 26 Step 26b | Methyl 5-(((2-(benzyloxy)ethyl)(4-fluorophenethyl)amino)methyl)-3-hydroxy-4-(hydroxymethyl)picolinate |
| 26 Step 26c | 5-({2-Benzyloxy-ethyl)-[2-(4-fluoro-phenyl)-ethyl]-amino}-methyl)-3-hydroxy-4-hydroxymethyl-pyridine-2-carboxylic acid hydroxyamide |
| 27 | 5-[3-(4-Fluoro-phenyl)-ureido]-3-hydroxy-4-hydroxymethyl-pyridine-2-carboxylic acid hydroxyamide |
| 27 Step 27b | Methyl 5-(3-(4-fluorophenyl)ureido)-3-hydroxy-4-(hydroxymethyl)picolinate |
| 27 Step 27c | 5-[3-(4-Fluoro-phenyl)-ureido]-3-hydroxy-4-hydroxymethyl-pyridine-2-carboxylic acid hydroxyamide |
| 28 | 5-(4-Fluoro-phenoxymethyl)-3-hydroxy-4-hydroxymethyl-pyridine-2-carboxylic acid hydroxyamide |
| 28 Step 28 a | Methyl 5-((4-fluorophenoxy)methyl)-3-hydroxy-4-(hydroxymethyl)picolinate |
| 28 Step 28b | Methyl 5-((4-fluorophenoxy)methyl)-3-hydroxy-4-(hydroxymethyl)picolinate |
| 29 | 5-(3-Chloro-4-fluoro-phenoxymethyl)-3-hydroxy-4-hydroxymethyl-pyridine-2-carboxylic acid hydroxyamide |
| 29 Step 29a | Methyl 5-((3-chloro-4-fluorophenoxy)methyl)-2,2-dimethyl-4H-[1,3]dioxino[4,5-c]pyridine-8-carboxylate |
| 29 Step 29b | Methyl 5-((3-chloro-4-fluorophenoxy)methyl)-2,2-dimethyl-4H-[1,3]dioxino[4,5-c]pyridine-8-carboxylate |
| 30 | 5-(3-Chloro-4-fluoro-benzyloxymethyl)-3-hydroxy-4-hydroxymethyl-pyridine-2-carboxylic acid hydroxyamide |
| 31 | 5-[2-(4-Fluoro-phenyl)-ethoxymethyl]-3-hydroxy-4-hydroxymethyl-pyridine-2-carboxylic acid hydroxyamide |
| 32 | 5-(2,4-Difluoro-benzyloxymethyl)-3-hydroxy-4-hydroxymethyl-pyridine-2-carboxylic acid hydroxyamide |
| 33 | 5-(3,4-Difluoro-benzyloxymethyl)-3-hydroxy-4-hydroxymethyl-pyridine-2-carboxylic acid hydroxyamide |
| 34 | 5-(4-Fluoro-benzyloxymethyl)-3-hydroxy-4-hydroxymethyl-pyridine-2-carboxylic acid hydroxyamide |
| 35 | 5-(4-Fluoro-phenoxymethyl)-3-hydroxy-4-methyl-pyridine-2-carboxylic acid hydroxyamide |
| 35, Step 35a | Methyl 3-(benzyloxy)-5-((4-fluorophenoxy)methyl)-4-methylpicolinate |
| 35, Step 35b | Methyl 5-((4-fluorophenoxy)methyl)-3-hydroxy-4-methylpicolinate |
| 36 | 5-(3-Chloro-4-fluoro-phenoxymethyl)-3-hydroxy-4-methyl-pyridine-2-carboxylic acid hydroxyamide |
| 36, Step 36 a | Methyl 3-(benzyloxy)-5-((3-chloro-4-fluorophenoxy)methyl)-4-methylpicolinate |
| 36, Step 36b | Methyl 5-((3-chloro-4-fluorophenoxy)methyl)-3-hydroxy-4-methylpicolinate |
| 37 | 5-(2,4-Difluoro-benzyloxymethyl)-3-hydroxy-4-methyl-pyridine-2-carboxylic acid hydroxyamide |
| 38 | 5-(3,4-Difluoro-benzyloxymethyl)-3-hydroxy-4-methyl-pyridine-2-carboxylic acid hydroxyamide |
| 39 | 5-(4-Fluoro-benzyloxymethyl)-3-hydroxy-4-methyl-pyridine-2-carboxylic acid hydroxyamide |
| 40 | 5-Benzyloxymethyl-3-hydroxy-4-methyl-pyridine-2-carboxylic acid hydroxyamide |
| 41 | (S)-(−)-3-Hydroxy-4-hydroxymethyl-pyridine-2,5-dicarboxylic acid 2-hydroxyamide 5-[(1-phenyl-ethyl)-amide] |
| 42 | 3-Hydroxy-4-hydroxymethyl-pyridine-2,5-dicarboxylic acid 2-hydroxyamide 5-[(pyridin-2-ylmethyl)-amide] |
| 43 | 3-Hydroxy-4-hydroxymethyl-pyridine-2,5-dicarboxylic acid 5-benzylamide 2-hydroxyamide |
| 44 | (S)-(−)-3-Hydroxy-4-hydroxymethyl-pyridine-2,5-dicarboxylic acid 2-hydroxyamide 5-[(2-hydroxy-1-phenyl-ethyl)-amide] |
| 45 | Pyridine-2,5-dicarboxylic acid 5-(4-fluoro-benzylamide) 2-hydroxyamide |
| 46 | 2,2-Dimethyl-4H-[1,3]dioxino[4,5-c]pyridine-5,8-dicarboxylic acid 5-{[1-(4-fluoro-phenyl)-cyclopropyl]-amide} 8-hydroxyamide |
| 47 | 3-Hydroxy-4-hydroxymethyl-pyridine-2,5-dicarboxylic acid 5-{[1-(4-fluoro-phenyl)-cyclopropyl]-amide} 2-hydroxyamide |
| 48 | 2,2-Dimethyl-4H-[1,3]dioxino[4,5-c]pyridine-5,8-dicarboxylic acid 5-(4-fluoro-benzylamide) 8-(methoxy-amide) |
| 49 | 3-Hydroxy-4-hydroxymethyl-pyridine-2,5-dicarboxylic acid 5-(4-fluoro-benzylamide) 2-(methoxy-amide) |
| 50 | 2,2-Dimethyl-4H-[1,3]dioxino[4,5-c]pyridine-5,8-dicarboxylic acid 5-cyclohexylmethyl-amide 8-hydroxyamide |
| 51 | 3-Hydroxy-4-hydroxymethyl-pyridine-2,5-dicarboxylic acid 5-cyclohexylmethyl-amide 2-hydroxyamide |
| 52 | 3-Hydroxy-4-hydroxymethyl-pyridine-2,5-dicarboxylic acid 5-cyclohexylmethyl-amide 2-hydroxyamide |
| 53 | 4-Hydroxymethyl-3-methoxy-pyridine-2,5-dicarboxylic acid 5-(4-fluoro-benzylamide) 2-hydroxyamide |
| 54- | -3-Hydroxy-4-hydroxymethyl-pyridine-2,5-dicarboxylic acid 5-(4-fluoro-benzylamide) 2-(hydroxy-methyl-amide) |
| 55 | 3-Hydroxy-4-hydroxymethyl-pyridine-2,5-dicarboxylic acid 5-dibenzylamide 2-hydroxyamide |
| 56 | 5-{[1-(4-Fluoro-phenyl)-cyclopropylamino]-methyl}-3-hydroxy-4-hydroxymethyl-pyridine-2-carboxylic acid hydroxyamide |
| 57 | 5-{[1-(4-Fluoro-phenyl)-cyclopropylamino]-methyl}-2,2-dimethyl-4H-[1,3]dioxino[4,5-c]pyridine-8-carboxylic acid hydroxyamide |
| 58 | 5-(4-Fluoro-benzyloxymethyl)-3-hydroxy-4-hydroxymethyl-pyridine-2-carboxylic acid methoxy-amide |
| 59 | 2,2-Dimethyl-4H-[1,3]dioxino[4,5-c]pyridine-5,8-dicarboxylic acid 5-(4-fluoro-2-methylcarbamoyl-benzylamide) 8-hydroxyamide |
| 60 | 3-Hydroxy-4-hydroxymethyl-pyridine-2,5-dicarboxylic acid 2-hydroxyamide 5-(4-methyl-benzylamide) |
| 61 | 3-Hydroxy-4-hydroxymethyl-pyridine-2,5-dicarboxylic acid 5-{[2-(4-fluoro-phenyl)-ethyl]-amide} 2-hydroxyamide |
| 62 | 3-Hydroxy-4-hydroxymethyl-pyridine-2,5-dicarboxylic acid 5-(2,4-difluoro-benzylamide) 2-hydroxyamide |
| 63 | (rac)-{2-(4-Chloro-phenyl)-1-[(4-fluoro-benzyl)-(5-hydroxy-6-hydroxycarbamoyl-4-hydroxymethyl-pyridin-3-ylmethyl)-carbamoyl]-ethyl}-carbamic acid methyl ester |

TABLE 3-continued

Listing of Compounds in Examples

| Example, step | Chemical Name |
|---|---|
| 64 | (rac) 5-{[(4-Fluoro-benzyl)-(2-phenyl-cyclopropanecarbonyl)-amino]-methyl}-3-hydroxy-4-hydroxymethyl-pyridine-2-carboxylic acid hydroxyamide |
| 65 | (4-Fluoro-benzyl)-(5-hydroxy-6-hydroxycarbamoyl-4-hydroxymethyl-pyridin-3-ylmethyl)-carbamic acid methyl ester |
| 66 | (3-Chloro-4-fluoro-benzyl)-(5-hydroxy-6-hydroxycarbamoyl-4-hydroxymethyl-pyridin-3-ylmethyl)-carbamic acid benzyl ester |
| 67 | 5-[2-(4-Fluoro-phenyl)-ethyl]-3-hydroxy-4-hydroxymethyl-pyridine-2-carboxylic acid hydroxyamide |
| 68 | 3-Hydroxy-4-hydroxymethyl-5-(3-phenyl-propyl)-pyridine-2-carboxylic acid hydroxyamide |
| 69 | 5-Benzenesulfonylmethyl-3-hydroxy-4-hydroxymethyl-pyridine-2-carboxylic acid hydroxyamide |
| 70 | 5-(4-Fluoro-phenylmethanesulfonylmethyl)-2,2-dimethyl-4H-[1,3]dioxino[4,5-c]pyridine-8-carboxylic acid hydroxyamide |
| 71 | 5-(4-Fluoro-phenylmethanesulfonylmethyl)-3-hydroxy-4-hydroxymethyl-pyridine-2-carboxylic acid hydroxyamide |
| 72 | (4-Fluoro-benzyl)-(5-hydroxy-6-hydroxycarbamoyl-4-methyl-pyridin-3-ylmethyl)-carbamic acid benzyl ester |
| 72 Step 72b | 5-[[(4-Fluoro-benzylamino)-methyl]-3-hydroxy-4-methyl-pyridine-2-carboxylic acid methyl ester |
| 73 | (4-Fluoro-benzyl)-(5-hydroxy-6-hydroxycarbamoyl-4-methyl-pyridin-3-ylmethyl)-carbamic acid tert-butyl ester |
| 74 | 3-Hydroxy-4-methyl-pyridine-2,5-dicarboxylic acid 5-(3-chloro-4-fluoro-benzylamide) 2-hydroxyamide |
| 75 | 5-(4-Fluoro-benzyloxymethyl)-3-hydroxy-4-hydroxymethyl-pyridine-2-carboxylic acid methoxy-amide |

Example 76

Biological Evaluation, In Vitro Integrase Inhibition Assay

IC50 was determined for the compounds of the inventions based on data generated in strand transfer assays. The IC50 is a measure of the ability of the compounds tested to inhibit the integration of 3'-processed oligonucleotides by recombinant HIV-1 integrase.

Strand transfer assays were performed essentially as described in Hazuda, D. J.; Felock, P.; Hastings, J. C.; Pramanik, B.; Wolfe, A. J. Virol. 1997, 71, 7005-7011). Donor DNA (1.5 pmol/well), biotinylated on the 5' end of the strand processed by integrase, was immobilized onto streptavidin-coated microtiter plates. Recombinant integrase (250 ng/well) was assembled onto the immobilized donor oligonucleotide in reaction buffer (20 mM Hepes, pH 7.6, 5 mM B-mercaptoethanol, 50 ug/mL bovine serum albumin) containing 30 mM MnCl2. Excess enzyme was removed, and the complexes were washed extensively prior to the addition of the target DNA substrate. The target DNA (0.75 pmoles/well) substrate was labeled on each 3' end with FITC. After strand transfer, the FITC-labeled products were detected using an anti-FITC antibody conjugated with alkaline phosphatase (Roche) and a chemiluminescent substrate (Tropix CSPD with Sapphire II enhancer, Applied Biosystems). The assay was performed in a final concentration of 10% DMSO. To specifically evaluate inhibition of strand transfer, compounds were added after assembly, just prior to the addition of the target DNA.

The results of the integrase strand transfer assay are reported as $IC_{50}$ values. $IC_{50}$ values were determined using a sigmoidal dose-response equation. The formula used for calculating % inhibition was: % Inhibition=[1-(sample counts/average of positive control)]*100. The percent inhibition of HIV-1 integrase activity was graphed against the log of the compound concentration (M). Using GraphPad Prism or ActivityBase (IDBS) software $IC_{50}$ was determined using following sigmoidal dose-response equation:

$$Y=(A+((B-A)/(1+((C/X)\hat{}D))))$$

Where A is the lower plateau (~0%), B is the higher plateau (~100%), C is the $IC_{50}$, D is the slope, X is the compound concentration (M), and Y is the % inhibition.

Inhibition of strand transfer, as determined by their $IC_{50}$, demonstrates that the compounds of the present invention inhibit HIV integrase and have $IC_{50}$s similar to that of Raltegravir, a marketed HIV integrase inhibitor, and L-708906, an integrase inhibitor currently in clinical development.

| Compound | ST $IC_{50}$ |
|---|---|
| Raltegravir (MK-0518) | 0.065 |
| L-708906 (Merck) | 0.045 |
| Compound of Example 14 | 0.027 |
| Compound of Example 2 | 0.303 |
| Compound of Example 18 | 0.088 |

Example 77

Antiviral Efficacy

The antiviral efficacies of the integrase inhibitor compounds of the invention were evaluated based on $EC_{50}$ measures obtained from two different in vitro HIV infection assay using cultured MT-4 cells: (1) a multi-cycle infection where cells were infected with wild type NL-4.3) and (2) a single-cycle infection where the cells were infected with a luciferase-bearing, envelope defective (env-) NL-4.3 virus pseudotyped with HIV-1 env (HXBc2.

The incubation period for the multi-cycle infection assay was 6 days. Cell viability (cytoprotection) and $EC_{50}$ were determined using the colorimetric MTT assay (A. J. Japour et al, Antimicrobial Agents and Chemotherapy, 37, 1095-1101, 1993 and R. Pauwels et al. Journal of Virological Methods, 20, 309-321, 1988).

The incubation period for the single-cycle infection assay was 48 hours. $EC_{50}$ was determined, as described by Chen et al., Journal of Virology, February 1994, Vol. 68, No. 2, p. 654-660, based on measures of luciferase signal over a range of drug concentrations.

The results of these assays are shown in Table 3 and integrase inhibitors of the invention were prepared using the synthetic methods described in Schemes 1-15; and the examples described herein. The reference numbers of the compounds listed in Table 4 (Ex. No.) correspond to the example numbers of examples 1 to 75 described above. These data demonstrate the antiviral efficacy of the compounds of the invention as integrase inhibitors and for treatment of HIV infection and AIDS. The compounds tested display potent antiviral activity. Furthermore, similar antiviral activity was observed when the HIV-1 envelope was replaced with VSV-G, validating that the compounds of the invention are post-entry inhibitors.

TABLE 4

Results of Cytoprotection-Cytotoxicity Assay

| Ex. No. | Compound | $EC_{50}$ (nM) multi-cycle |
|---|---|---|
| — | L-708906 (a integrase inhibitor currently in development at Merck) | 5800 |
| — | MK-0518 (Raltegravir, a marketed integrase inhibitor, brand name Isentress ™) | 20 |
| 1 | $N^2$,3-bis(benzyloxy)-$N^5$-(4-fluorobenzyl)-4-(hydroxymethyl)pyridine-2,5-dicarboxamide | >10000 |
| 2 | $N^5$-(4-fluorobenzyl)-$N^2$,3-dihydroxy-4-(hydroxymethyl)pyridine-2,5-dicarboxamide | 358 |
| 3 | $N^5$-(benzo[d][1,3]dioxol-5-ylmethyl)-$N^2$,3-bis(benzyloxy)-4-(hydroxymethyl)pyridine-2,5-dicarboxamide | >10000 |
| 4 | $N^5$-(benzo[d][1,3]dioxol-5-ylmethyl)-$N^2$,3-dihydroxy-4-hydroxymethyl)pyridine-2,5-dicarboxamide | >10000 |
| 5 | $N^2$,3-bis(benzyloxy)-4-(hydroxymethyl)-$N^5$-(4-methoxybenzyl)pyridine-2,5-dicarboxamide | 900 |
| 6 | $N^2$,3-dihydroxy-4-(hydroxymethyl)-$N^5$-(4-methoxybenzyl)pyridine-2,5-dicarboxamide | 1000 |
| 7 | $N^2$,3-bis(benzyloxy)-$N^5$-(3,5-difluorobenzyl)-4-(hydroxymethyl)pyridine-2,5-dicarboxamide | 1500 |
| 8 | $N^5$-(3,5-difluorobenzyl)-$N^2$,3-dihydroxy-4-(hydroxymethyl)pyridine-2,5-dicarboxamide | >10000 |
| 9 | 5-((4-fluorobenzylamino)methyl)-N,3-dihydroxy-4-(methoxymethyl)picolinamide | 1000 |
| 10 | 5-((3,5-difluorobenzylamino)methyl)-N,3-dihydroxy-4-(hydroxymethyl)picolinamide | >10000 |
| 11 | 5-((benzo[d][1,3]dioxol-5-ylmethylamino)methyl)-N,3-dihydroxy-4-(hydroxymethyl)picolinamide | 300 |
| 12 | $N^5$-(4-fluorobenzyl)-$N^2$,3-dihydroxy-4-(methoxymethyl)-N5-methylpyridine-2,5-dicarboxamide | 14000 |
| 13 | $N^2$,3-bis(benzyloxy)-$N^5$-(3-chloro-4-fluorobenzyl)-4-(hydroxymethyl)pyridine-2,5-dicarboxamide | >10000 |
| 14 | $N^5$-(3-chloro-4-fluorobenzyl)-$N^2$,3-dihydroxy-4-(hydroxymethyl)pyridine-2,5-dicarboxamide | 123 |
| 15 | $N^2$,3-bis(benzyloxy)-$N^5$-(3,4-dichlorobenzyl)-4-(hydroxymethyl)pyridine-2,5-dicarboxamide | >10000 |
| 16 | $N^5$-(3,4-dichlorobenzyl)-$N^2$,3-dihydroxy-4-(hydroxymethyl)pyridine-2,5-dicarboxamide | 700 |
| 17 | N,3-Dihydroxy-4-(hydroxymethyl)-5-((4-methoxybenzyloxy)methyl)-picolinamide | 2000 |
| 18 | 5-(Benzyloxymethyl)-N,3-dihydroxy-4-(hydroxymethyl)picolinamide | 86 |
| 19 | N-hydroxy-5-((4-methoxybenzyloxy)methyl)-2,2-dimethyl-4H-[1,3]dioxino[4,5-c]pyridine-8-carboxamide | 5058 |
| 20 | $N^5$-(3,4-difluorobenzyl)-$N^2$,3-dihydroxy-4-(hydroxymethyl)pyridine-2,5-dicarboxamide | 30 |
| 21 | 5-[(4-Fluoro-phenylamino)-methyl]-3-hydroxy-4-hydroxymethyl-pyridine-2-carboxylic acid hydroxyamide | 4.3 |
| 23 | 5-(4-Fluoro-benzoylamino)-3-hydroxy-4-hydroxymethyl-pyridine-2-carboxylic acid hydroxyamide | 6300 |
| 25 | 5-{[Benzyl-(4-fluoro-phenyl)-amino]-methyl}-3-hydroxy-4-hydroxymethyl-pyridine-2-carboxylic acid hydroxyamide | 175 |
| 27 | 5-[3-(4-Fluoro-phenyl)-ureido]-3-hydroxy-4-hydroxymethyl-pyridine-2-carboxylic acid hydroxyamide | 1096 |
| 28 | 5-(4-Fluoro-phenoxymethyl)-3-hydroxy-4-hydroxymethyl-pyridine-2-carboxylic acid hydroxyamide | 186 |
| 65 | (4-Fluoro-benzyl)-(5-hydroxy-6-hydroxycarbamoyl-4-hydroxymethyl-pyridin-3-ylmethyl)-carbamic acid methyl ester | >10000 |
| 67 | 5-[2-(4-Fluoro-phenyl)-ethyl]-3-hydroxy-4-hydroxymethyl-pyridine-2-carboxylic acid hydroxyamide | 235 |
| 71 | 5-(4-Fluoro-phenylmethanesulfonylmethyl)-3-hydroxy-4-hydroxymethyl-pyridine-2-carboxylic acid hydroxyamide | 4.3 |
| 74 | 3-Hydroxy-4-methyl-pyridine-2,5-dicarboxylic acid 5-(3-chloro-4-fluoro-benzylamide) 2-hydroxyamide | 267 |

Example 78

Inhibition of HIV-1 Clinical Isolates in PBMCs

Acute infection assays using fresh human phytohemagglutinin (PHA)-stimulated peripheral blood mononuclear cells (PBMCs) were carried out. PBMCs were stimulated with IL-2 and infected with one of two wild-type drug-sensitive clinical HIV-1 isolates. The strains HIV-1 used for the infections, 91US005 (primary R5 strain of HIV-1) and 94US33931N, are both Group M, Subtype B viruses. Antiviral activity was determined as a reduction in supernatent reverse transcriptase (RT) activity after a 6 day incubation.

Compounds of the invention $N^5$-(4-fluorobenzyl)-$N^2$,3-dihydroxy-4-(hydroxymethyl)pyridine-2,5-dicarboxamide (product of example 2) and of $N^5$-(benzo[d][1,3]dioxol-5-ylmethyl)-N2,3-bis(benzyloxy)-4-(hydroxymethyl)pyridine-2,5-dicarboxamide (product of example 3) and Retrovir (AZT), a reverse transcriptase inhibitor, were tested at 9 concentrations and the $EC_{50}$ of each compound was determined. These data demonstrate that the compounds of the invention inhibit infection of PBMCs by HIV-1 isolates.

The results of these assays are provided in Table 5 below.

TABLE 5

Results of assays in PMBCs

| Compound | HIV-1 isolate | EC50 (uM) |
|---|---|---|
| Example 2 | 91US005 | 0.076 |
| Example 2 | 94US33931N | 0.123 |
| Example 3 | 91US005 | 0.093 |
| Example 3 | 94US33931N | 0.03 |
| Retrovir (AZT) | 91US005 | 0.006 |
| Retrovir (AZT) | 94US33931N | 0.003 |

Example 79

Effect of Protein Binding on Antiviral Activity

Protein binding was tested by Rapid Equilibrium Dialysis (RED) method (The RED (Rapid equilibrium Dialysis) Device inserts instruction manual. Pierce, Rockford Ill.). Compounds were spiked in human serum (HS) or 10% FBS-RPMI at a concentration of 1 uM. The red chamber was loaded with 0.3 mL of samples containing compounds. The white chamber contained 0.5 mL of D-PBS buffer only. The plate was incubated at 37° C. while shaking at 150 rpm for 5 hours. Aliquots from both chambers were analyzed by LC/MS/MS. The multi-cycle antiviral activity in the absence and presence of human serum was determined by p24 ELISA measurement after 6 days of NL4.3 virus infection. The results, showing a moderate effect of protein binding on antiviral activity, are provided in Table 6 below.

TABLE 6

Effect of Protein Binding on Antiviral Activity

| Compound | % Protein Binding | | $EC_{50}$ (uM) | | Fold-change with HS |
|---|---|---|---|---|---|
| Protein Spike | 10% FBS | 100% HS | 10% FBS | 10% FBS + 40% HS | |
| Raltegravir | 34.7 | 86.7 | 0.047 | 0.064 | 1.4 |
| Example 1 | 52.5 | 89 | 0.227 | 0.481 | 2.1 |
| Example 2 | 31.9 | 84.5 | na | na | na |

Example 80

Human CYP Inhibition

For the human CYP inhibition experiments, the incubation medium contained 0.3 mg/mL human liver microsomes, 100 mM phosphate buffer pH 7.4, 5 mM MgCl2, 1 mM EDTA. The respective substrates for CYP3A4, CYP2C9 and CYP2D6 were added at various concentrations in the presence or absence of the compounds tested. After pre-incubation, the reaction was initiated by the addition of NADPH at final concentration 1 mM. Incubation times were 10, 60 and 15 minutes for CYP3A4, CYP2C9 and CYP2D6, respectively (Walsky R L and Obach R S., Drug Metabolism and Disposition, 2004, 32, 647-660). GraphPad Prism software was used for data analysis. The results of these assays, showing the metabolic stability of the compounds of the invention are provided in Table 7 below.

TABLE 7

Results of CYP Inhibition Assays

| Compound | Vmax (pmol/min/mg) | Km (µM) | Ki (µM) |
|---|---|---|---|
| CYP34A | | | |
| Example 1 | 3652 | 11.24 | 5.10 |
| Example 2 | 1252 | 7.76 | 1.11E+16 |
| Example 3 | 1247 | 8.30 | 586.80 |
| CYP2C9 | | | |
| Example 1 | 78.72 | 293.20 | 63.60 |
| Example 2 | NA | NA | NA |
| Example 3 | NA | NA | NA |
| CYP2D5 | | | |
| Example 1 | NA | NA | NA |
| Example 2 | 32.16 | 5.24 | 1.84E+13 |
| Example 3 | 36.02 | 5.79 | 4.87E+20 |

Example 81

Human Liver Microsome Stability

Human liver microsome stability was assayed by incubation of liver microsomes (0.6 mg/mL), in medium containing 100 mM phosphate buffer pH 7.4, 10 mM MgCl2, 1 mM EDTA, 25 µg Alamethicin/mg protein, and 1 mM NADPH, 1 mM UDPGA, or 1 mM NADPH and 1 mM UDPGA. After pre-incubation, the assay was started by the addition of 1 µM of compound. Samples were taken after 0, 15, 30, 60, 90 and 120 minutes of incubation (Fisher M B, Drug Metabolism and Disposition, 2000, 28, 560-566). GraphPad Prism software was used for data analysis. The results, showing that the compounds of the invention are metabolically stable in Human liver microsomes, are provided in Table 7 below.

TABLE 7

Stability of Compounds in Human Liver Microsomes

| | Half-life in HLM (hrs) | | |
|---|---|---|---|
| Compound | NADPH | UDPGA | NADPH/UDPGA |
| Raltegravir | 19.7 | 7.03 | 11 |
| Compound 1 | 7.4 | 19.7 | 3.9 |
| Compound 2 | 5 | 16 | 5.9 |
| Compound 3 | 6.18 | 3.8 | 1.95 |

Example 82

Pharmacokinetic (PK) Profile in Rats

Female Sprague-Dawley rats were randomly selected and assigned to two groups. A group of 13 rats were administered 5 mg/kg of compound 2 intravenously. A second group of 8 rats were administered 50 mg/kg of compound 2 orally. Following the dosing, blood was collected at 7 different time points. Plasma samples obtained from the blood samples were analyzed by LC/MS/MS and the bioavailability of compound 2 was determined. FIG. 1 shows the results of this experiment demonstrating the high adsorption and generally favourable profile of the compounds of the invention.

Other Embodiments

The examples, synthetic schemes and procedures provided herein are for the purpose of illustration only. They are not intended to be exhaustive or to limit the scope of the invention to the specific examples, synthetic schemes, and procedures described herein. Although the invention has been described with reference to several embodiments, it will be understood by one of ordinary skill in the art that various modifications can be made without departing from the spirit and the scope of the invention, as set forth in the claims. Other embodiments are in the claims.

All patents, patent applications, and publications referenced herein, including U.S. provisional application No. 61/130,874, filed Jun. 4, 2008, are hereby incorporated by reference.

What is claimed is:
1. A compound of formula I,

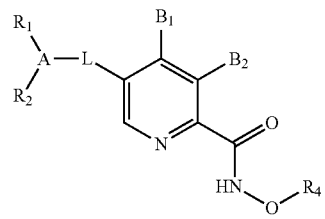

wherein:
A is a six membered carbocyclic or heterocyclic ring system;
$R_1$ is H, $C_{1-6}$ alkyl, $C_{1-6}$ branched alkyl, $C_{2-6}$ alkenyl, halogen (F, Cl, Br, I), OH, O—($C_{1-6}$ alkyl), (O—$C_{1-6}$ branched alkyl), CO($R_9$), COO($R_9$), CON($R_9$)($R_{9a}$), or SO$_2$N($R_9$)($R_{9a}$), wherein said $R_9$ and $R_{9a}$ are selected independently from the group consisting of H, $C_{1-6}$ alkyl, $C_{1-6}$ fluoro-alkyl, benzyl, phenyl, and heterocycle;
$R_2$ is H, $C_{1-6}$ alkyl, $C_{1-6}$ branched alkyl, $C_{2-6}$ alkenyl, halogen (F, Cl, Br, I), OH, O—($C_{1-6}$ alkyl), (O—$C_{1-6}$ branched alkyl), CO($R_{10}$), COO($R_{10}$), or CON($R_{10}$)($R_{10a}$), wherein said $R_{10}$ and $R_{10a}$ are selected independently from the group consisting of H, $C_{1-6}$ alkyl, $C_{1-6}$ fluoro-alkyl, benzyl, phenyl, and heterocycle; or $R_1$ and $R_2$ are ortho substituents that together form a carbocyclic or heterocyclic ring system;
L is —N(R')C(O)—; —C(O)N(R')—; —OC(O)—; —C(O)O—; —OC(O)N(R')—; —N(R')C(O)O—; —N(R')C(O)N(R')—; —C($R_{a1}$)($R_{a2}$)C($R_{b1}$)($R_{b2}$)C($R_{c1}$)($R_{c2}$)—; —C($R_{a1}$)($R_{a2}$)C($R_{b1}$)($R_{b2}$)—; —C($R_{a1}$)($R_{a2}$)C($R_{b1}$)($R_{b2}$)C($R_{c1}$)($R_{c2}$)—Z—C($R_{a1}$)($R_{a2}$)C($R_{b1}$)($R_{b2}$)C($R_{c1}$)($R_{c2}$)—; —C($R_{a1}$)($R_{a2}$)C($R_{b1}$)($R_{b2}$)C($R_{c1}$)($R_{c2}$)—Z—C($R_{a1}$)($R_{a2}$)C($R_{b1}$)($R_{b2}$)—; —C($R_{a1}$)($R_{a2}$)C($R_{b1}$)($R_{b2}$)C($R_{c1}$)($R_{c2}$)—Z—C($R_{a1}$)($R_{a2}$)—; —C($R_{a1}$)($R_{a2}$)C($R_{b1}$)($R_{b2}$)C($R_{c1}$)($R_{c2}$)—Z—; —C($R_{a1}$)($R_{a2}$)C($R_{b1}$)($R_{b2}$)—Z—C($R_{a1}$)($R_{a2}$)C($R_{b1}$)

$(R_{b2})C(R_{c1})(R_{c2})$—; —$C(R_{a1})(R_{a2})$—Z—$C(R_{a1})(R_{a2})$ $C(R_{b1})(R_{b2})C(R_{c1})(R_{c2})$—; —Z—$C(R_{a1})(R_{a2})C(R_{b1})$ $(R_{b2})C(R_{c1})(R_{c2})$—; —$C(R_{a1})(R_{a2})C(R_{b1})(R_{b2})$—Z— $C(R_{a1})(R_{a2})C(R_{b1})(R_{b2})$—; —$C(R_{a1})(R_{a2})C(R_{b1})$ $(R_{b2})$—Z—$C(R_{a1})(R_{a2})$—; —$C(R_{a1})(R_{a2})C(R_{b1})$ $(R_{b2})$—; —Z—$C(R_{a1})(R_{a2})$—Z—$C(R_{a1})(R_{a2})C(R_{b1})$ $(R_{b2})$—; —Z—$C(R_{a1})(R_{a2})C(R_{b1})(R_{b2})$—; —$C(R_{a1})$ $(R_{a2})$—Z—$C(R_{a1})(R_{a2})$—; —$C(R_{a1})(R_{a2})$—Z—; —Z—$C(R_{a1})(R_{a2})$—; —$SO_2CH_2$—; or —$CH_2SO_2CH_2$—;

wherein each $R_{a1}$, $R_{a2}$, $R_{b1}$, $R_{b2}$, $R_{c1}$, and $R_{c2}$ is, independently, selected from the group consisting of H, $C_{1-6}$ alkyl, $C_{1-6}$ fluoro-alkyl, hydroxy-alkyl, benzyl, phenyl, and heterocycle, or, alternatively, one or more of $R_{a1}$ and $R_{a2}$; $R_{b1}$ and $R_{b2}$; and $R_{c1}$ and $R_{c2}$ combine to form a carbocyclic ring, and wherein Z is selected from the group consisting of —N(R')C(O)—; —C(O)N(R')—; —OC(O)—; —C(O)O—; —OC(O)N(R')—; —N(R')C(O)O—; —N(R')C(O)N(R')—; —N(R')—; and —O—; wherein R' is selected from the group consisting of H, $C_{1-6}$ alkyl, benzyl, $SO_2R''$, $C(O)R''$, and $C(O)OR''$, and R'' is selected from the group consisting of $C_{1-6}$ alkyl, $C_{1-6}$ fluoro-alkyl, heteroalkyl, carbocyclic group, benzyl, phenyl, and heterocycle;

$B_1$ is —$R_3$, $CH_2OR_3$, $CH_2N(R_8)(R_{8a})$, $C(O)OR_3$, or $C(O)N(R_8)(R_{8a})$, wherein each of $R_8$ and $R_{8a}$ is, independently, selected from the group consisting of H, $C_{1-6}$ alkyl, $C_{1-6}$ fluoro-alkyl, benzyl, phenyl, and heterocycle;

$B_2$ is H or $OR_5$;

$R_3$ is H, $C_{1-6}$ alkyl, $C_{1-6}$ fluoroalkyl, benzyl, phenyl, or heterocycle; and $R_5$ is H, $C_{1-6}$ alkyl, $C_{1-6}$ fluoroalkyl, benzyl, phenyl, or heterocycle; or, alternatively, $R_3$ and $R_5$ combine to form a heterocyclic ring system; and $R_4$ is H, $C_{1-6}$ alkyl, $C_{1-6}$ fluoroalkyl, benzyl, phenyl, or heterocycle;

or a pharmaceutically acceptable salt thereof.

2. A compound according to claim 1, wherein A is a phenyl ring, a pyridine ring, or a cyclohexyl ring.

3. A compound according to claim 1, wherein L is —$CH_2OCH_2$—, —$CH_2CH_2OCH_2$—, —$OCH_2$—, —$CH_2NHCH_2$—, —$C(cyclo-C_2H_4)NHCH_2$—, —$NHCH_2$—, —$CH_2CH_2NHCH_2$—, —$CH_2NHC(O)$—, —$CH_2N(CH_3)C(O)$—, —$CH(CH_2OH)NHC(O)$—, —$C(cyclo-C_2H_4)NHC(O)$—, —$CH_2CH_2NHC(O)$—, —$C(O)NH$—, —$CH_2OC(O)NH$—, —$NHC(O)NH$—, —$CH_2CH_2$—, —$CH_2CH_2$—, —$SO_2CH_2$—, or —$CH_2SO_2CH_2$—.

4. A compound according to claim 1, wherein $B_1$ is H, $CH_3$, $CH_2OH$, or $CH_2OCH_3$.

5. A compound according to claim 1, wherein $B_2$ is H or —$OR_5$ and $R_5$ is H or benzyl.

6. A compound according to claim 1, wherein L is —$CH_2NHCH_2$— or —$CH_2NHC(O)$—.

7. A compound according to claim 6, wherein each of $R_1$ and $R_2$ is, independently, halogen, —$OCH_3$, —OH, or $R_1$ and $R_2$ combine to form a cyclic acetal or cyclic ketal.

8. A compound according to claim 7 wherein, $R_4$ is —H or benzyl.

9. A compound according to claim 1, wherein L is —$CH_2OCH_2$—.

10. A compound according to claim 9, wherein each of $R_1$ and $R_2$ is, independently, halogen, —$OCH_3$, —OH, or $R_1$ and $R_2$ combine to form a cyclic acetal or cyclic ketal.

11. A compound according to claim 9, wherein $R_4$ is —H or benzyl.

12. A compound according to claim 3, wherein L is —$SO_2CH_2$— or —$CH_2SO_2CH_2$—.

13. A compound according to claim 12, wherein each of $R_1$ and $R_2$ is, independently, halogen, —$OCH_3$, —OH, or $R_1$ and $R_2$ combine to form a cyclic acetal or cyclic ketal.

14. A compound according to claim 13, wherein $R_4$ is —H or benzyl.

15. A compound according to claim 3, wherein A is a phenyl ring.

16. A compound selected from the group consisting of:
$N^2$, 3-bis(benzyloxy)-$N^5$-(4-fluorobenzyl)-4-(hydroxymethyl)pyridine-2,5-dicarboxamide;
$N^5$-(4-fluorobenzyl)-$N^2$,3-dihydroxy-4-(hydroxymethyl)pyridine-2,5-dicarboxamide;
$N^5$-(benzo[d][1,3]dioxol-5-ylmethyl)-N2,3-bis(benzyloxy)-4-(hydroxymethyl)pyridine-2,5-dicarboxamide;
$N^5$-(benzo[d][1,3]dioxol-5-ylmethyl)-N2,3-dihydroxy-4-(hydroxymethyl)pyridine-2,5-dicarboxamide;
$N^2$, 3-bis(benzyloxy)-4-(hydroxymethyl)-$N^5$-(4-methoxybenzyl)pyridine-2,5-dicarboxamide;
$N^2$, 3-dihydroxy-4-(hydroxymethyl)-$N^5$-(4-methoxybenzyppyridine-2,5-dicarboxamide;
$N^2$, 3-bis(benzyloxy)-$N^5$-(3,5-difluorobenzyl)-4-(hydroxymethyl)pyridine-2,5-dicarboxamide;
$N^5$-(3,5-difluorobenzyl)-$N^2$,3-dihydroxy-4-(hydroxymethyl)pyridine-2,5-dicarboxamide;
5-((4-fluorobenzylamino)methyl)-N,3-dihydroxy-4-(methoxymethyl)picolinamide);
5-((3,5-difluorobenzylamino)methyl)-N,3-dihydroxy-4-(hydroxymethyl)picolinamide;
5-((benzo[d][1,3]dioxol-5-ylmethylamino)methyl)-N,3-dihydroxy-4-(hydroxymethyl)picolinamide;
$N^5$-(4-fluorobenzyl)-$N^2$, 3-dihydroxy-4-(methoxymethyl)-$N^5$-methylpyridine-2,5-dicarboxamide;
$N^2$, 3-bis(benzyloxy)-$N^5$-(3-chloro-4-fluorobenzyl)-4-(hydroxymethyl)pyridine-2,5-dicarboxamide;
$N^5$-(3-chloro-4-fluorobenzyl)-N2,3-dihydroxy-4-(hydroxymethyl)pyridine-2,5-dicarboxamide;
$N^2$, 3-bis(benzyloxy)-$N^5$-(3,4-dichlorobenzyl)-4-(hydroxymethyl)pyridine-2,5-dicarboxamide;
$N^5$-(3,4-dichlorobenzyl)-$N^2$,3-dihydroxy-4-(hydroxymethyl)pyridine-2,5-dicarboxamide;
N,3-dihydroxy-4-(hydroxymethyl)-5-((4-methoxybenzyloxy)methyl)-picolinamide;
5-(benzyloxymethyl)-N,3-dihydroxy-4-(hydroxymethyl) picolinamide;
N-hydroxy-5-((4-methoxybenzyloxy)methyl)-2,2-dimethyl-4H-[1,3]dioxino[4,5-c]pyridine-8-carboxamide;
$N^5$-(3,4-difluorobenzyl)-$N^2$,3-dihydroxy-4-(hydroxymethyl)pyridine-2,5-dicarboxamide;
5-[(4-fluoro-phenylamino)-methyl]-3-hydroxy-4-hydroxymethyl-pyridine-2-carboxylic acid hydroxyamide;
5-{([2-(4-fluoro-phenyl)-ethylamino]-methyl}-3-hydroxy-4-hydroxymethyl-pyridine-2-carboxylic acid hydroxyamide;
5-(4-fluoro-benzoylamino)-3-hydroxy-4-hydroxymethyl-pyridine-2-carboxylic acid hydroxyamide;
(8-hydroxycarbamoyl-2,2-dimethyl-4H-[1,3]dioxino[4,5-c]pyridin-5-yl)-carbamic acid benzyl ester;
5-{[benzyl-(4-fluoro-phenyl)-amino]-methyl}-3-hydroxy-4-hydroxymethyl-pyridine-2-carboxylic acid hydroxyamide;
5-({(2-benzyloxy-ethyl)-[2-(4-fluoro-phenyl)-ethyl]-amino}-methyl)-3-hydroxy-4-hydroxymethyl-pyridine-2-carboxylic acid hydroxyamide;
5-[3-(4-fluoro-phenyl)-ureido]-3-hydroxy-4-hydroxymethyl-pyridine-2-carboxylic acid hydroxyamide;

5-(4-fluoro-phenoxymethyl)-3-hydroxy-4-hydroxymethyl-pyridine-2-carboxylic acid hydroxyamide;
5-(3-chloro-4-fluoro-phenoxymethyl)-3-hydroxy-4-hydroxymethyl-pyridine-2-carboxylic acid hydroxyamide;
methyl 5-((3-chloro-4-fluorophenoxy)methyl)-2,2-dimethyl-4H-[1,3]dioxino[4,5-c]pyridine-8-carboxylate;
5-(3-chloro-4-fluoro-benzyloxymethyl)-3-hydroxy-4-hydroxymethyl-pyridine-2-carboxylic acid hydroxyamide;
5-[2-(4-fluoro-phenyl)-ethoxymethyl]-3-hydroxy-4-hydroxymethyl-pyridine-2-carboxylic acid hydroxyamide;
5-(2,4-difluoro-benzyloxymethyl)-3-hydroxy-4-hydroxymethyl-pyridine-2-carboxylic acid hydroxyamide;
5-(3,4-difluoro-benzyloxymethyl)-3-hydroxy-4-hydroxymethyl-pyridine-2-carboxylic acid hydroxyamide;
5-(4-fluoro-benzyloxymethyl)-3-hydroxy-4-hydroxymethyl-pyridine-2-carboxylic acid hydroxyamide;
5-(4-fluoro-phenoxymethyl)-3-hydroxy-4-methyl-pyridine-2-carboxylic acid hydroxyamide;
5-(3-chloro-4-fluoro-phenoxymethyl)-3-hydroxy-4-methyl-pyridine-2-carboxylic acid hydroxyamide;
5-(2,4-difluoro-benzyloxymethyl)-3-hydroxy-4-methyl-pyridine-2-carboxylic acid hydroxyamide;
5-(3,4-difluoro-benzyloxymethyl)-3-hydroxy-4-methyl-pyridine-2-carboxylic acid hydroxyamide;
5-(4-fluoro-benzyloxymethyl)-3-hydroxy-4-methyl-pyridine-2-carboxylic acid hydroxyamide;
5-benzyloxymethyl-3-hydroxy-4-methyl-pyridine-2-carboxylic acid hydroxyamide;
(S)-(−)-3-hydroxy-4-hydroxymethyl-pyridine-2,5-dicarboxylic acid 2-hydroxyamide 5-[(1-phenyl-ethyl)-amide];
3-hydroxy-4-hydroxymethyl-pyridine-2,5-dicarboxylic acid 2-hydroxyamide 5-[(pyridin-2-ylmethyl)-amide];
3-hydroxy-4-hydroxymethyl-pyridine-2,5-dicarboxylic acid 5-benzylamide 2-hydroxyamide;
(S)-(−)-3-hydroxy-4-hydroxymethyl-pyridine-2,5-dicarboxylic acid 2-hydroxyamide 5-[(2-hydroxy-1-phenyl-ethyl)-amide];
pyridine-2,5-dicarboxylic acid 5-(4-fluoro-benzylamide) 2-hydroxyamide;
2,2-dimethyl-4H-[1,3]dioxino[4,5-c]pyridine-5,8-dicarboxylic acid 5-{([1-(4-fluoro-phenyl)-cyclopropyl]-amide}8-hydroxyamide;
3-hydroxy-4-hydroxymethyl-pyridine-2,5-dicarboxylic acid 5-{([1-(4-fluoro-phenyl)-cyclopropyl]-amide}2-hydroxyamide;
2,2-dimethyl-4H-[1,3]dioxino[4,5-c]pyridine-5,8-dicarboxylic acid 5-(4-fluoro-benzylamide) 8-(methoxy-amide);
3-hydroxy-4-hydroxymethyl-pyridine-2,5-dicarboxylic acid 5-(4-fluoro-benzylamide) 2-(methoxy-amide);
2,2-dimethyl-4H-[1,3]dioxino[4,5-c]pyridine-5,8-dicarboxylic acid 5-cyclohexylmethyl-amide 8-hydroxyamide;
3-hydroxy-4-hydroxymethyl-pyridine-2,5-dicarboxylic acid 5-cyclohexylmethyl-amide 2-hydroxyamide;
3-hydroxy-4-hydroxymethyl-pyridine-2,5-dicarboxylic acid 5-cyclohexylmethyl-amide 2-hydroxyamide;
4-hydroxymethyl-3-methoxy-pyridine-2,5-dicarboxylic acid 5-(4-fluoro-benzylamide) 2-hydroxyamide;
3-hydroxy-4-hydroxymethyl-pyridine-2,5-dicarboxylic acid 5-(4-fluoro-benzylamide) 2-(hydroxy-methyl-amide);
3-hydroxy-4-hydroxymethyl-pyridine-2,5-dicarboxylic acid 5-dibenzylamide 2-hydroxyamide;
5-{([1-(4-fluoro-phenyl)-cyclopropylamino]-methyl}-3-hydroxy-4-hydroxymethyl-pyridine-2-carboxylic acid hydroxyamide;
5-{([1-(4-fluoro-phenyl)-cyclopropylamino]-methyl}-2,2-dimethyl-4H-[1,3]dioxino[4,5-c]pyridine-8-carboxylic acid hydroxyamide;
5-(4-fluoro-benzyloxymethyl)-3-hydroxy-4-hydroxymethyl-pyridine-2-carboxylic acid methoxy-amide;
2,2-dimethyl-4H-[1,3]dioxino[4,5-c]pyridine-5,8-dicarboxylic acid 5-(4-fluoro-2-methylcarbamoyl-benzylamide) 8-hydroxyamide;
3-hydroxy-4-hydroxymethyl-pyridine-2,5-dicarboxylic acid 2-hydroxyamide 5-(4-methyl-benzylamide);
3-hydroxy-4-hydroxymethyl-pyridine-2,5-dicarboxylic acid 5-{[2-(4-fluoro-phenyl)-ethyl]-amide}2-hydroxyamide;
3-hydroxy-4-hydroxymethyl-pyridine-2,5-dicarboxylic acid 5-(2,4-difluoro-benzylamide) 2-hydroxyamide;
(rac)-(2-(4-Chloro-phenyl)-1-[(4-fluoro-benzyl)-(5-hydroxy-6-hydroxycarbamoyl-4-hydroxymethyl-pyridin-3-ylmethyl)-carbamoyl]-ethyl}-carbamic acid methyl ester;
(rac) 5-{[(4-Fluoro-benzyl)-(2-phenyl-cyclopropanecarbonyl)-amino]-methyl}-3-hydroxy-4-hydroxymethyl-pyridine-2-carboxylic acid hydroxyamide;
(4-fluoro-benzyl)-(5-hydroxy-6-hydroxycarbamoyl-4-hydroxymethyl-pyridin-3-ylmethyl)-carbamic acid methyl ester;
(3-chloro-4-fluoro-benzyl)-(5-hydroxy-6-hydroxycarbamoyl-4-hydroxymethyl-pyridin-3-ylmethyl)-carbamic acid benzyl ester;
5-[2-(4-Fluoro-phenyl)-ethyl]-3-hydroxy-4-hydroxymethyl-pyridine-2-carboxylic acid hydroxyamide;
3-hydroxy-4-hydroxymethyl-5-(3-phenyl-propyl)-pyridine-2-carboxylic acid hydroxyamide;
5-benzenesulfonylmethyl-3-hydroxy-4-hydroxymethyl-pyridine-2-carboxylic acid hydroxyamide;
5-(4-fluoro-phenylmethanesulfonylmethyl)-2,2-dimethyl-4H-[1,3]dioxino[4,5-c]pyridine-8-carboxylic acid hydroxyamide;
5-(4-fluoro-phenylmethanesulfonylmethyl)-3-hydroxy-4-hydroxymethyl-pyridine-2-carboxylic acid hydroxyamide;
(4-fluoro-benzyl)-(5-hydroxy-6-hydroxycarbamoyl-4-methyl-pyridin-3-ylmethyl)-carbamic acid benzyl ester;
(4-fluoro-benzyl)-(5-hydroxy-6-hydroxycarbamoyl-4-methyl-pyridin-3-ylmethyl)-carbamic acid tert-butyl ester;
3-hydroxy-4-methyl-pyridine-2,5-dicarboxylic acid 5-(3-chloro-4-fluoro-benzylamide) 2-hydroxyamide;
and
5-(4-fluoro-benzyloxymethyl)-3-hydroxy-4-hydroxymethyl-pyridine-2-carboxylic acid methoxy-amide;
or a pharmaceutically acceptable salt thereof.

17. A compound according to claim 1 selected from the group consisting of:
N,9-bis(benzyloxy)-3,3-dimethyl-1,5-dihydro-[1,3]dioxepino[5,6-c]pyridine-8-carboxamide;
N,3-bis(benzyloxy)-4,5-bis(hydroxymethyl) picolinamide;
N,7-bis(benzyloxy)-3-oxo-1,3-dihydrofuro[3,4-c]pyridine-6-carboxamide;

N², 3-bis(benzyloxy)-N⁵-(4-fluorobenzyl)-4-(hydroxymethyl)pyridine-2,5-dicarboxamide;
N,3-bis(benzyloxy)-5-((4-fluorobenzylamino)methyl)-4-(hydroxymethyl)picolinamide;
5-((3,5-difluorobenzylamino)methyl)-N,3-dihydroxy-4-(hydroxymethyl)picolinamide;
5-((benzo[d][1,3]dioxol-5-ylmethylamino)methyl)-N,3-bis(benzyloxy)-4-(hydroxymethyl)picolinamide;
5-(benzyloxy)-N-(4-fluorobenzyl)-4-(hydroxymethyl)-6-methylnicotinamide;
5-(benzyloxy)-N-(4-fluorobenzyl)-4-(methoxymethyl)-N,6-dimethylnicotinamide;
3-(benzyloxy)-5-((4-fluorobenzyl)(methyl)carbamoyl)-4-(methoxymethyl)-2-methylpyridine 1-oxide;
5-(benzyloxy)-N-(4-fluorobenzyl)-6-(hydroxymethyl)-4-(methoxymethyl)-N-methylnicotinamide;
5-(benzyloxy)-N-(4-fluorobenzyl)-6-formyl-4-(methoxymethyl)-N-methylnicotinamide;
methyl 3-(benzyloxy)-5-((4-fluorobenzyl)(methyl) carbamoyl)-4-(methoxymethyl)picolinate;
N², 3-bis(benzyloxy)-N⁵-(4-fluorobenzyl)-4-(methoxymethyl)-N⁵-methylpyridine-2,5-dicarboxamide;
N⁵-(4-fluorobenzyl)-N2,3-dihydroxy-4-(methoxymethyl)-N⁵-methylpyridine-2,5-dicarboxamide;
5-((4-methoxybenzyloxy)methyl)-2,2,8-trimethyl-4H-[1,3]dioxino[4,5-c]pyridine;
5-((4-methoxybenzyloxy)methyl)-2,2,8-trimethyl-4H-[1,3]dioxino[4,5-c]pyridine 7-oxide;
(5-((4-methoxybenzyloxy)methyl)-2,2-dimethyl-4H-[1,3]dioxino[4,5-c]pyridin-8-yl)methanol;
5-((4-methoxybenzyloxy)methyl)-2,2-dimethyl-4H-[1,3]dioxino[4,5-c]pyridine-8-carbaldehyde;
ethyl 5-((4-methoxybenzyloxy)methyl)-2,2-dimethyl-4H-[1,3]dioxino[4,5-c]pyridine-8-carboxylate;
ethyl 3-hydroxy-4-(hydroxymethyl)-5-((4-methoxybenzyloxy)methyl)picolinate;
N, 3-dihydroxy-4-(hydroxymethyl)-5-((4-methoxybenzyloxy)methyl)picolinamide;
5-((4-methoxybenzyloxy)methyl)-2,2-dimethyl-4H-[1,3]dioxino[4,5-c]pyridine-8-carboxylic acid;
N-(benzyloxy)-5-((4-methoxybenzyloxy)methyl)-2,2-dimethyl-4H-[1,3]dioxino[4,5-c]pyridine-8-carboxamide;
N-(benzyloxy)-3-hydroxy-4-(hydroxymethyl)-5-((4-methoxybenzyloxy)methyl)picolinamide;
N-hydroxy-5-((4-methoxybenzyloxy)methyl)-2,2-dimethyl-4H-[1,3]dioxino[4,5-c]pyridine-8-carboxamide;
5-((4-fluorophenylamino)methyl)-3-hydroxy-4-(hydroxymethyl) picolinate;
8-(methoxycarbonyl)-2,2-dimethyl-4H-[1,3]dioxino[4,5-c]pyridine-5-carboxylic acid;
methyl 5-(benzyloxycarbonylamino)-2,2-dimethyl-4H-[1,3]dioxino[4,5-c]pyridine-8-carboxylate;
5-amino-2,2-dimethyl-4H-[1,3]dioxino[4,5-c]pyridine-8-carboxylic acid methyl ester;
methyl 5-(4-fluorobenzamido)-2,2-dimethyl-4H-[1,3]dioxino[4,5-c]pyridine-8-carboxylate;
methyl 5-(4-fluorobenzamido)-3-hydroxy-4-(hydroxymethyl)picolinate;
methyl 5-((benzyl(4-fluorophenyl)amino)methyl)-2,2-dimethyl-4H-[1,3]dioxino[4,5-c]pyridine-8-carboxylate;
methyl 5-(((2-(benzyloxy)ethyl)(4-fluorophenethyl)amino)methyl)-3-hydroxy-4-(hydroxymethyl)picolinate;
5-({(2-Benzyloxy-ethyl)-[2-(4-fluoro-phenyl)-ethyl]-amino}-methyl)-3-hydroxy-4-hydroxymethyl-pyridine-2-carboxylic acid hydroxyamide;
methyl 5-(3-(4-fluorophenyl)ureido)-3-hydroxy-4-(hydroxymethyl)picolinate;
5-[3-(4-Fluoro-phenyl)-ureido]-3-hydroxy-4-hydroxymethyl-pyridine-2-carboxylic acid hydroxyamide;
methyl 5-((4-fluorophenoxy)methyl)-3-hydroxy-4-(hydroxymethyl)picolinate;
methyl 5-((4-fluorophenoxy)methyl)-3-hydroxy-4-(hydroxymethyl)picolinate;
methyl 5-((3-chloro-4-fluorophenoxy)methyl)-2,2-dimethyl-4H-[1,3]dioxino[4,5-c]pyridine-8-carboxylate;
methyl 3-(benzyloxy)-5-((4-fluorophenoxy)methyl)-4-methylpicolinate;
methyl 5-((4-fluorophenoxy)methyl)-3-hydroxy-4-methylpicolinate;
methyl 3-(benzyloxy)-5-((3-chloro-4-fluorophenoxy)methyl)-4-methylpicolinate;
methyl 5-((3-chloro-4-fluorophenoxy)methyl)-3-hydroxy-4-methylpicolinate;
5-[(4-Fluoro-benzylamino)-methyl]-3-hydroxy-4-methyl-pyridine-2-carboxylic acid methyl ester;
methyl 5-((4-fluorophenylamino)methyl)-2,2-dimethyl-4H-[1,3]dioxino[4,5-c]pyridine-8-carboxylate; and
Methyl 5-((4-fluorophenethylamino)methyl)-3-hydroxy-4-(hydroxymethyl)picolinate;
or a pharmaceutically acceptable salt thereof.

18. A compound selected from the group consisting of:
N⁵-(4-fluorobenzyl)-N²,3-dihydroxy-4-(hydroxymethyl)pyridine-2,5-dicarboxamide;
N⁵-(3-chloro-4-fluorobenzyl)-N²,3-dihydroxy-4-(hydroxymethyl)pyridine-2,5-dicarboxamide;
N⁵-(3,4-dichlorobenzyl)-N²,3-dihydroxy-4-(hydroxymethyl)pyridine-2,5-dicarboxamide; and
5-(benzyloxymethyl)-N,3-dihydroxy-4-(hydroxymethyl)picolinamide;
or a pharmaceutically acceptable salt thereof.

19. A pharmaceutical composition comprising a compound according to claim 1 and a pharmaceutically acceptable carrier of diluent.

20. A pharmaceutical composition comprising a compound according to claim 1, at least one additional HIV-inhibiting agent, and a pharmaceutically acceptable carrier of diluent.

21. A method of treating an HIV infection in a mammal, said method comprising administering to said mammal a compound according to claim 1 in an amount effective for the treatment of said HIV infection, wherein, in the compound of claim 1, L is —N(R')C(O)—; —C(O)N(R')—; —OC(O)—; —C(O)O—; —OC(O)N(R')—; —N(R')C(O)O—; —N(R')C(O)N(R')—; —C($R_{a1}$)($R_{a2}$)—Z—C($R_{a1}$)($R_{a2}$)—; —C($R_{a1}$)($R_{a2}$)—Z—; —Z—C($R_{a1}$)($R_{a2}$)—; —SO₂CH₂—; or —CH₂SO₂CH₂—;

wherein each $R_{a1}$ and $R_{a2}$ is, independently, selected from the group consisting of H and $C_{1-6}$ alkyl, and wherein Z is selected from the group consisting of —N(R')C(O)—; —C(O)N(R')—; —OC(O)—; —C(O)O—; —OC(O)N(R')—; —N(R')C(O)O—; —N(R')C(O)N(R')—; —N(R')—; and —O—; wherein R' is selected from the group consisting of H, $C_{1-6}$ alkyl, SO₂R", C(O)R", and C(O)OR", and R" is selected from the group consisting of $C_{1-6}$ alkyl, $C_{1-6}$ fluoro-alkyl, carbocyclic group, and phenyl.

22. A method of treating AIDS or AIDS-related complex in a mammal, said method comprising administering to said mammal a compound according to claim 1 in an amount effective for the treatment of said AIDS or AIDS-related complex, wherein, in the compound of claim 1, L is —N(R')C(O)—; —C(O)N(R')—; —OC(O)—; —C(O)O—; —OC(O)N(R')—; —N(R')C(O)O—; —N(R')C(O)N(R')—; —C(R$_{a1}$)(R$_{a2}$)—Z—C(R$_{a1}$)(R$_{a2}$)—; —C(R$_{a1}$)(R$_{a2}$)—Z—; —Z—C(R$_{a1}$)(R$_{a2}$)—; —SO$_2$CH$_2$—; or —CH$_2$SO$_2$CH$_2$—;

wherein each R$_{a1}$ and R$_{a2}$ is, independently, selected from the group consisting of H and C$_{1-6}$ alkyl, and wherein Z is selected from the group consisting of —N(R')C(O)—; —C(O)N(R')—; —OC(O)—; —C(O)O—; —OC(O)N(R')—; —N(R')C(O)O—; —N(R')C(O)N(R')—; —N(R')—; and —O—; wherein R' is selected from the group consisting of H, C$_{1-6}$ alkyl, SO$_2$R", C(O)R", and C(O)OR", and R" is selected from the group consisting of C$_{1-6}$ alkyl, C$_{1-6}$ fluoro-alkyl, carbocyclic group, and phenyl.

23. A method of inhibiting HIV replication in a mammal, said method comprising administering to said mammal a compound according to claim 1 in an amount effective to inhibit HIV replication in a mammal, wherein, in the compound of claim 1, L is —N(R')C(O)—; —C(O)N(R')—; —OC(O)—; —C(O)O—; —OC(O)N(R')—; —N(R')C(O)O—; —N(R')C(O)N(R')—;

—C(R$_{a1}$)(R$_{a2}$)—Z—C(R$_{a1}$)(R$_{a2}$)—; —C(R$_{a1}$)(R$_{a2}$)—Z—; —Z—C(R$_{a1}$)(R$_{a2}$)—; —SO$_2$CH$_2$—; or —CH$_2$SO$_2$CH$_2$—;

wherein each R$_{a1}$ is, independently, selected from the group consisting of H and C$_{1-6}$ alkyl, and wherein Z is selected from the group consisting of —N(R')C(O)—; —C(O)N(R')—; —OC(O)—; —C(O)O—; —OC(O)N(R')—; —N(R')C(O)O—; —N(R')C(O)N(R')—; —N(R')—; and —O—; wherein R' is selected from the group consisting of H, C$_{1-6}$ alkyl, SO$_2$R", C(O)R", and C(O)OR", and R" is selected from the group consisting of C$_{1-6}$ alkyl, C$_{1-6}$ fluoro-alkyl, carbocyclic group, and phenyl.

24. A method of inhibiting HIV replication in a cell, said method comprising contacting said cell with a compound according to claim 1 in an amount sufficient to inhibit HIV replication, wherein, in the compound of claim 1, L is —N(R')C(O)—; —C(O)N(R')—; —OC(O)—; —C(O)O—; —OC(O)N(R')—; —N(R')C(O)O—; —N(R')C(O)N(R')—; —C(R$_{a1}$)(R$_{a2}$)—Z—C(R$_{a1}$)(R$_{a2}$)—; —C(R$_{a1}$)(R$_{a2}$)—Z—; —Z—C(R$_{a1}$)(R$_{a2}$)—; —SO$_2$CH$_2$—; or —CH$_2$SO$_2$CH$_2$—;

wherein each R$_{a1}$ is, independently, selected from the group consisting of H and C$_{1-6}$ alkyl, and wherein Z is selected from the group consisting of —N(R')C(O)—; —C(O)N(R')—; —OC(O)—; —C(O)O—; —OC(O)N(R')—;

—N(R')C(O)O—; —N(R')C(O)N(R')—; —N(R')—; and —O—; wherein R' is selected from the group consisting of H, C$_{1-6}$ alkyl, SO$_2$R", C(O)R", and C(O)OR", and R" is selected from the group consisting of C$_{1-6}$ alkyl, C$_{1-6}$ fluoro-alkyl, carbocyclic group, and phenyl.

25. The method of claim 21, said method further comprising administering to said mammal or contacting said cell with at least one additional HIV inhibiting agent.

26. The method of claim 25, wherein said HIV inhibiting agent is selected from the group consisting of an entry inhibitor, a protease inhibitor, a reverse transcriptase inhibitor, a fusion inhibitor, and an integrase inhibitor.

27. The method of claim 21, wherein said HIV is resistant to at least one HIV inhibiting agent.

28. A compound of formula I,

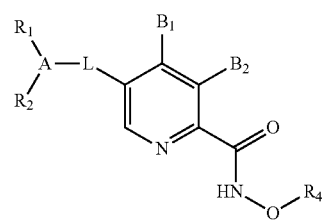

wherein:

A is a six membered carbocyclic or heterocyclic ring system;

R$_1$ is H, C$_{1-8}$ alkyl, C$_{1-8}$ branched alkyl, C$_{2-8}$ alkenyl, halogen (F, Cl, Br, I), OH, O—(C$_{1-8}$ alkyl), (O—C$_{1-8}$ branched alkyl), CO(R$_9$), COO(R$_9$), CON(R$_9$)(R$_{9a}$), or SO$_2$N(R$_9$)(R$_{9a}$), wherein said R$_9$ and R$_{9a}$ are selected independently from the group consisting of H, C$_{1-8}$ alkyl, C$_{1-8}$ fluoro-alkyl, benzyl, phenyl, and heterocycle;

R$_2$ is H, C$_{1-8}$ alkyl, C$_{1-8}$ branched alkyl, C$_{2-8}$ alkenyl, halogen (F, Cl, Br, I), OH, O—(C$_{1-8}$ alkyl), (O—C$_{1-6}$ branched alkyl), CO(R$_{10}$), COO(R$_{10}$), or CON(R$_{10}$)(R$_{10a}$), wherein said R$_{10}$ and R$_{10a}$ are selected independently from the group consisting of H, C$_{1-9}$ alkyl, C$_{1-6}$ fluoro-alkyl, benzyl, phenyl, and heterocycle; or R$_1$ and R$_2$ are ortho substituents that together form a carbocyclic or heterocyclic ring system;

L is —N(R')C(O)—; —C(O)N(R')—; —OC(O)—; —C(O)O—; —OC(O)N(R')—; —N(R')C(O)O—; —N(R')C(O)N(R')—;

—C(R$_{a1}$)(R$_{a2}$)C(R$_{b1}$)(R$_{b2}$)C(R$_{c1}$)(R$_{c2}$)—; —C(R$_{a1}$)(R$_{a2}$)C(R$_{b1}$)(R$_{b2}$)—; —C(R$_{a1}$)(R$_{a2}$)C(R$_{b1}$)(R$_{b2}$)C(R$_{c1}$)(R$_{c2}$)—Z—C(R$_{a1}$)(R$_{a2}$)C(R$_{b1}$)(R$_{b2}$)C(R$_{c1}$)(R$_{c2}$)—; —C(R$_{a1}$)(R$_{a2}$)C(R$_{b1}$)(R$_{b2}$)C(R$_{c1}$)(R$_{c2}$)—Z—C(R$_{a1}$)(R$_{a2}$)C(R$_{b1}$)(R$_{b2}$)—; —C(R$_{a1}$)(R$_{a2}$)C(R$_{b1}$)(R$_{b2}$)C(R$_{c1}$)(R$_{c2}$)—Z—C(R$_{a1}$)(R$_{a2}$)—; —C(R$_{a1}$)(R$_{a2}$)C(R$_{b1}$)(R$_{b2}$)C(R$_{c1}$)(R$_{c2}$)—Z—; —C(R$_{a1}$)(R$_{a2}$)C(R$_{b1}$)(R$_{b2}$)—Z—C(R$_{a1}$)(R$_{a2}$)C(R$_{b1}$)(R$_{b1}$)C(R$_{c1}$)(R$_{c2}$)—; —C(R$_{a1}$)(R$_{a2}$)—Z—C(R$_{a1}$)(R$_{a2}$)C(R$_{b1}$)(R$_{b2}$)C(R$_{c1}$)(R$_{c2}$)—; —Z—C(R$_{a1}$)(R$_{a2}$)C(R$_{b1}$)(R$_{b2}$)C(R$_{c1}$)(R$_{c2}$)—; —C(R$_{a1}$)(R$_{a2}$)C(R$_{b1}$)(R$_{b2}$)—Z—C(R$_{a1}$)(R$_{a2}$)C(R$_{b1}$)(R$_{b2}$)—; —C(R$_{a1}$)(R$_{a2}$)C(R$_{b1}$)(R$_{b2}$)—Z—C(R$_{a1}$)(R$_{a2}$)—; —C(R$_{a1}$)(R$_{a2}$)C(R$_{b1}$)(R$_{b2}$)—Z—; —C(R$_{a1}$)(R$_{a2}$)—Z—C(R$_{a1}$)(R$_{a2}$)C(R$_{b1}$)(R$_{b2}$)—; —Z—C(R$_{a1}$)(R$_{a2}$)C(R$_{b1}$)(R$_{b2}$)—;

—C(R$_{a1}$)(R$_{a2}$)—Z—C(R$_{a1}$)(R$_{a2}$)—; —C(R$_{a1}$)(R$_{a2}$)—Z—; or —Z—C(R$^{a1}$)(R$^{a2}$)—; wherein each R$_{a1}$, R$_{a2}$, R$_{b1}$, R$_{b2}$, R$_{b1}$, and R$_{c2}$ is, independently, selected from the group consisting of H, C$_{1-6}$ alkyl, C$_{1-6}$ fluoro-alkyl, hydroxy-alkyl, benzyl, phenyl, and heterocycle, or, alternatively, one or more of R$_{a1}$ and R$_{a2}$; R$_{b1}$ and R$_{b2}$; and R$_{c1}$ and R$_{c2}$ combine to form a carbocyclic ring, and wherein Z is selected from the group consisting of —N(R')C(O)—; —C(O)N(R')—; —OC(O)—; —C(O)O—; —OC(O)N(R')—; —N(R')C(O)O—; —N(R')C(O)N(R')—; —N(R')—; —SO$_2$—; and —O—; wherein R' is selected from the group consisting of H, C$_{1-6}$ alkyl, benzyl, SO$_2$R", C(O)R", and C(O)OR", and R" is selected from the group consisting of C$_{1-6}$ alkyl, C$_{1-6}$ fluoro-alkyl, heteroalkyl, carbocyclic group, benzyl, phenyl, and heterocycle;

B$_1$ is —R$_3$, CH$_2$OR$_3$, CH$_2$N(R$_8$)(R$_{8a}$), C(O)OR$_3$, or C(O)N(R$_8$)(R$_{8a}$), wherein each of R$_8$ and R$_{8a}$ is, independently, selected from the group consisting of H, $C_{1-8}$ alkyl, $C_{1-8}$ fluoro-alkyl, benzyl, phenyl, and heterocycle;

$B_2$ is $OR_5$;

$R_3$ is H, $C_{1-6}$ alkyl, $C_{1-6}$ fluoroalkyl, benzyl, phenyl, or heterocycle; and $R_5$ is H, $C_{1-6}$ alkyl, $C_{1-6}$ fluoroalkyl, benzyl, phenyl, or heterocycle; or, alternatively, $R_3$ and $R_5$ combine to form a heterocyclic ring system; and $R_4$ is H, $C_{1-8}$ alkyl, $C_{1-8}$ fluoroalkyl, benzyl, phenyl, or heterocycle;

or a pharmaceutically acceptable salt thereof.

\* \* \* \* \*